United States Patent
Ling et al.

(10) Patent No.: US 12,005,080 B2
(45) Date of Patent: Jun. 11, 2024

(54) METHOD FOR PROMOTING PROLIFERATION OF IMMUNE CELLS

(71) Applicant: Oricell Therapeutics Co., Ltd., Shanghai (CN)

(72) Inventors: Youguo Ling, Shanghai (CN); Hao Guo, Shanghai (CN); Xiaowen He, Shanghai (CN); Haili Ma, Shanghai (CN); Huijiao Li, Shanghai (CN); Huajing Wang, Shanghai (CN); Bi Ying, Shanghai (CN); Huanfeng Yang, Shanghai (CN)

(73) Assignee: Oricell Therapeutics Co., Ltd., Shanghai (CN)

( * ) Notice: Subject to any disclaimer, the term of this patent is extended or adjusted under 35 U.S.C. 154(b) by 315 days.

(21) Appl. No.: 17/040,865

(22) PCT Filed: Mar. 25, 2019

(86) PCT No.: PCT/CN2019/079576
§ 371 (c)(1),
(2) Date: Sep. 23, 2020

(87) PCT Pub. No.: WO2019/184886
PCT Pub. Date: Oct. 3, 2019

(65) Prior Publication Data
US 2021/0106620 A1    Apr. 15, 2021

(30) Foreign Application Priority Data
Mar. 26, 2018 (CN) .......................... 201810251875.7

(51) Int. Cl.
| | | |
|---|---|---|
| A61K 35/17 | (2015.01) | |
| A61P 35/00 | (2006.01) | |
| C07K 14/705 | (2006.01) | |
| C12N 5/0783 | (2010.01) | |
| C12N 15/86 | (2006.01) | |

(52) U.S. Cl.
CPC .............. *A61K 35/17* (2013.01); *A61P 35/00* (2018.01); *C07K 14/705* (2013.01); *C12N 5/0636* (2013.01); *C12N 15/86* (2013.01); *C12N 2740/15043* (2013.01)

(58) Field of Classification Search
None
See application file for complete search history.

(56) References Cited

U.S. PATENT DOCUMENTS

2018/0216185 A1    8/2018 Olek

FOREIGN PATENT DOCUMENTS

WO    WO 2017/050916 A1    3/2017
WO    WO-2017040287 A1 *  3/2017 .............. A61K 38/55

OTHER PUBLICATIONS

Nilsson et al. Biochemical and Biophysical Research Communications, 417 (2012) 1304-1309. (Year: 2012).*
Zhang et al. Wnt signaling activation and mammary gland hyperplasia in MMTV-LRP6 transgenic mice: implication for breast cancer tumorigenesis. Oncogene (2010) 29:539-549. Electronically published Nov. 2, 2009. (Year: 2009).*
He et al. Co-expressing LRP6 With Anti-CD19 CAR-T Cells for Improved Therapeutic Effect Against B-ALL. Front. Oncol. (2020) 10:1-9. (Year: 2020).*
International Search Report dated Jul. 29, 2019 in PCT/CN2019/079576 (submitting English translation only), 4 total pages.
Hong, Y. et al, "Deletion of LRP5 and LRP6 in dendritic cells enhances antitumor immunity", OncoImmunology, vol. 5, No. 4, pp. e1115941-1 to e1115941-10, 2016, DOI: 10.1080/2162402X.2015.1115941, 11 total pages.
Semba, K. et al., A v-erbB-related protooncogene, c-erbB-2, is distinct from the c-erbB-1/epidermal growth factor-receptor gene and is amplified in a human salivary gland adenocarcinoma, Proceedings of the National Academy of Sciences, vol. 82, pp. 6497-6501, 1985, 5 total pages.
Yamamoto, T. et al., "Similarity of protein encoded by the human c-erb-B-2 gene to epidermal growth factor receptor", Letters to Nature, Nature vol. 319, pp. 230-234, 1986, 5 total pages.
GenBank: XP_024306409, "receptor tyrosine-protein kinase erbB-2 isoform X1 [*Homo sapiens*]", Protein—NCBI, BioProject: PRJNA168, https.://www.ncbi.nih.gov/protein/XP_024306409.1, 2020, 2 total pages.
Pearson, W. R. et al., "Improved tools for biological sequence comparison", Proceedings of the National Academy of Sciences, vol. 85, pp. 2444-2448, 1988, 5 total pages.
Lipman, D. J., "Rapid and Sensitive Protein Similarity Searches", Science, vol. 227, pp. 1435-1441, 1985, 7 total pages.
Altschul, S. F. et al., "Basic Local Alignment Search Tool", Journal of Molecular Biology, vol. 215, pp. 403-410, 1990, 8 total pages.
Extended European Search Report dated Dec. 10, 2021 in European Patent Application No. 19776983.9, 7 pages.
Ravi K. Kancha, et al., "Up-Regulation of the Low Density Lipoprotein Receptor-Related Protein by Dexamethasone in HepG2 Cells" Biochimica et Biophysica Acta—Lipids and Lipid Metabolism, XP055867128, vol. 1301, No. 3, Jun. 1, 1996, pp. 213-220.
Toomas Talme, et al., "Regulation of T-lymphocyte Motility, Adhesion and De-Adhesion by a Cell Surface Mechanism Directed by Low Density Lipoprotein Receptor-Related Protein 1 and Endogenous Thrombospondin-1" Immunology, XP055867126, vol. 142, No. 2, Apr. 24, 2014, pp. 176-192.

(Continued)

*Primary Examiner* — Allison M Fox
*Assistant Examiner* — Alyssa G Weston
(74) *Attorney, Agent, or Firm* — Oblon, McClelland, Maier & Neustadt, L.L.P.

(57) ABSTRACT

Disclosed is a method for promoting immune cell proliferation. The method comprises the following step: upregulating the expression of low-density lipoprotein receptor-related proteins or fragments thereof in immune cells.

9 Claims, 6 Drawing Sheets
Specification includes a Sequence Listing.

(56) References Cited

OTHER PUBLICATIONS

Ping He, et al., "Co-Expressing LRP6 with Anti-CD19 CAR-T Cells for Improved Therapeutic Effect Against B-ALL" Frontiers in Oncology, XP055867017, vol. 10, Sep. 15, 2020, pp. 1-9.

* cited by examiner

| Name of Construct | Schematic Structure |
|---|---|
| GPC3-41BB | GPC3 scFv-CD8-41BB-CD3z |
| GPC3-41BB-L6 | GPC3 scFv-CD8-41BB-CD3z-2A-L6 |
| GPC3-41BB-TL6 | GPC3 scFv-CD8-41BB-CD3z-2A-TL6 |
| GPC3-CD28 | GPC3 scFv-CD8-CD28-CD3z |
| GPC3-CD28-L6 | GPC3 scFv-CD8-CD28-CD3z-2A-L6 |
| GPC3-CD28-TL6 | GPC3 scFv-CD8-CD28-CD3z-2A-TL6 |
| GPC3-41BB-L5 | GPC3 scFv-CD8-41BB-CD3z-2A-L5 |
| GPC3-41BB-TL5 | GPC3 scFv-CD8-41BB-CD3z-2A-TL5 |
| CD19-41BB | CD19 scFv-CD8-41BB-CD3z |
| CD19-41BB-L6 | CD19 scFv-CD8-41BB-CD3z-2A-L6 |
| CD19-41BB-TL6 | CD19 scFv-CD8-41BB-CD3z-2A-TL6 |
| BCMA-41BB | BCMA scFv-CD8-41BB-CD3z |
| BCMA-41BB-L6 | BCMA scFv-CD8-41BB-CD3z-2A-L6 |
| BCMA-41BB-TL6 | BCMA scFv-CD8-41BB-CD3z-2A-TL6 |
| MSLN-41BB | MSLN scFv-CD8-41BB-CD3z |
| MSLN-41BB-L6 | MSLN scFv-CD8-41BB-CD3z-2A-L6 |
| MSLN-41BB-TL6 | MSLN scFv-CD8-41BB-CD3z-2A-TL6 |
| HER2-41BB | HER2 scFv-CD8-41BB-CD3z |
| HER2-41BB-L6 | HER2 scFv-CD8-41BB-CD3z-2A-L6 |
| HER2-41BB-TL6 | HER2 scFv-CD8-41BB-CD3z-2A-TL6 |

Fig 1

METHOD FOR PROMOTING PROLIFERATION OF IMMUNE CELLS

CROSS-REFERENCE TO RELATED APPLICATIONS

This application is a National Stage Application and claims priority under 35 U.S.C. § 371 to Patent Cooperation Treaty application PCT/CN2019/079576, filed Mar. 25, 2019, which claims the benefit of Chinese application 201810251875.7, filed Mar. 26, 2018. Priority is claimed to these applications and the disclosures of these prior applications are considered part of the disclosure of this application and to the extent allowed the entire contents of the aforementioned applications are incorporated herein.

FIELD

The present application relates to a method for promoting the proliferation of an immune cell. In particular, the method of the present application can up-regulate the expression of a low density lipoprotein receptor-associated protein or fragment thereof in the immune cell.

BACKGROUND

Chimeric Antigen Receptor T-Cell Immunotherapy (CAR-T) involves modifying a T cell by means of genetic engineering to allow it to express a Chimeric antigen receptor (CAR) and recognize an antibody of a tumor cell surface antigen, thereby enhancing a specific killing of tumor by the T cell. CAR generally comprises specially recognizing a Single chain variable fragment (scFv), a hinge region, a transmembrane region, and an intracellular signal transduction region of a Tumor associated antigen (TAA).

Recently, CAR-T immunotherapy has significant effects in the treatment of acute leukemias and non-Hodgkin's lymphomas, but the CAR-expressing immune cells have an extremely limited proliferation ability.

Summary

The present application provides a genetically modified immune cell, and a method for promoting the proliferation of immune cells. The method provided in the present application can up-regulate the expression of the low density lipoprotein receptor-associated protein or fragment thereof in the immune cell. The method provided in the present application can further promote the production of a memory immune cell. The method provided in the present application can further inhibit the differentiation of immune cells. The method provided in the present application can further enhance the release of a cytokine from immune cell. The method provided in the present application can further enhance the ability of the immune cells to kill a tumor. Moreover, the method provided in the present application can be used to prevent the recurrence of tumors in a subject. The present application further provides a method for treating tumors in a subject in need thereof. The present application further provides a composition including the genetically modified immune cell, as well as use of the genetically modified immune cell and the composition in the manufacture of a drug. The present application further provides a method for producing the genetically modified immune cells.

In one aspect, the present application provides a method for promoting the proliferation of immune cells, including a following step: upregulating the expression of the low density lipoprotein receptor-associated protein or fragment thereof in the immune cell.

In one aspect, the present application provides a method for promoting the production of memory immune cells, including a following step: upregulating the expression of the low density lipoprotein receptor-associated protein or fragment thereof in the immune cells, thereby promoting the differentiation of the immune cells to the memory immune cells.

In one aspect, the present application provides a method for inhibiting the differentiation of immune cells, including a following step of upregulating the expression of the low density lipoprotein receptor-associated protein or fragment thereof in the immune cells, thereby inhibiting the differentiation of the immune cells to the differentiated immune cells.

In one aspect, the present application provides a method for enhancing the release of cytokines from immune cells, including a following step: upregulating the expression of the low density lipoprotein receptor-associated protein or fragment thereof in the immune cell.

In certain embodiments, the cytokines comprise interleukin, interferon and/or tumor necrosis factor. In certain embodiments, the cytokines comprise IL-2, IL4, IL6, IL7, IL10, IL12, TNF-$\alpha$ and/or IFN$\gamma$.

In one aspect, the present application provides a method for enhancing the ability of immune cells to kill tumors, including a following step: upregulating the expression of the low density lipoprotein receptor-associated protein or fragment thereof in the immune cells.

In one aspect, the present application provides a method for preventing the tumor recurrence in a subject, including administering immune cells to a subject susceptible to a tumor, wherein the expression of the low density lipoprotein receptor-associated protein or fragment thereof is upregulated in the immune cells.

In one aspect, the present application provides a method for treating tumors in a subject in need thereof, including a following step: administering immune cells to the subject, wherein the expression of the low density lipoprotein receptor-associated protein or fragment thereof is upregulated in the immune cell.

In certain embodiments, the tumor is selected from the group consisting of liver cancer, lung cancer, leukemia, and mesothelioma.

In certain embodiments, the method comprises an in vivo method and an in vitro method.

In certain embodiments, the immune cell comprises a lymphocyte. In certain embodiments, the immune cell comprises a T cell. In certain embodiments, the T cell comprises a memory stem cell-like T cells (TSCM) and/or a central memory T cells (TCM). In certain embodiments, the TSCM is CCR7$^+$ and/or CD62L$^+$. In certain embodiments, the TSCM further has one or more properties selected from the group consisting of CD45RA$^+$ $^{or}$ $^{CD}$45RA$^-$, CD45RO$^+$ $^{or}$ $^{CD}$45RO$^-$, CD28$^+$, CD127$^+$, CD122$^+$, CD4$^+$, and CD8$^+$.

In certain embodiments, the immune cell comprises genetically modified immune cells, and the genetically modified immune cells express chimeric antigen receptor (CAR) or a T cell receptor (TCR). In certain embodiments, the genetically modified immune cell comprises a genetically modified T cell.

In certain embodiments, the CAR comprises an intracellular domain, and the intracellular domain comprises a signal transduction domain and/or a costimulatory domain.

In certain embodiments, the signal transduction domain comprises a moiety selected from the group consisting of a signal transduction domain of CD3ζ, a signal transduction domain of CD3δ, and a signal transduction domain of CD3ε. In certain embodiments, the signal transduction domain comprises an amino acid sequence as set forth in SEQ ID NO: 18 or an amino acid sequence having at least 80% homology thereof. In certain embodiments, a nucleic acid molecule encoding the signal transduction domain comprises a nucleic acid sequence as set forth in SEQ ID NO:17 or a nucleic acid sequence having at least 80% homology thereof.

In certain embodiments, the costimulatory domain comprises a moiety selected from the group consisting of a costimulatory domain of CD27, a costimulatory domain of CD28, and a costimulatory domain of 4-1BB. In certain embodiments, the costimulatory domain comprises an amino acid sequence as set forth in any one of SEQ ID NO:14, and SEQ ID NO:16 or an amino acid sequence having at least 80% homology thereof. In certain embodiments, a nucleic acid molecule encoding the costimulatory domain comprises a nucleic acid sequence as set forth in any one of SEQ ID NO:13, and SEQ ID NO:15 or a nucleic acid sequence having at least 80% homology thereof.

In certain embodiments, the CAR comprises a hinge region. In certain embodiments, the hinge region comprises a moiety selected from the group consisting of a hinge region of IgG4, a hinge region of IgG1, and a hinge region of CD8. In certain embodiments, the hinge region comprises an amino acid sequence as set forth in SEQ ID NO: 31. In certain embodiments, a nucleic acid molecule encoding the hinge region comprises a nucleotide sequence as set forth in SEQ ID NO: 32.

In certain embodiments, the CAR comprises a transmembrane region. In certain embodiments, the transmembrane region comprises a moiety selected from the group consisting of a transmembrane region of CD8, a transmembrane region of CD28, and a transmembrane region of CD24. In certain embodiments, the transmembrane region comprises an amino acid sequence as set forth in SEQ ID NO: 33. In certain embodiments, a nucleic acid molecule encoding the transmembrane region comprises a nucleotide sequence as set forth in SEQ ID NO: 34.

In certain embodiments, the CAR comprises a targeting moiety. In certain embodiments, the targeting moiety comprises ScFv.

In certain embodiments, the targeting moiety specially binds to and/or recognizes tumor antigen. In certain embodiments, the targeting moiety specially binds to and/or recognizes a target selected from the group consisting of B lymphocyte surface antigens, TNF family members, HER family members, and GPC family members. In certain embodiments, the targeting moiety specially binds to and/or recognizes a target selected from the group consisting of CD19, BCMA, HER2, Mesothelin, and GPC3.

In certain embodiments, the targeting moiety is an antibody or antigen-binding fragment thereof that specially binds to and/or recognizes CD19, and the antibody or antigen-binding fragment thereof comprises a light chain variable region including LCDR1-LCDR3, wherein the LCDR1 comprises an amino acid sequence as set forth in SEQ ID NO: 46 or an amino acid sequence having at least 80% homology thereof; the LCDR2 comprises an amino acid sequence as set forth in SEQ ID NO: 47 or an amino acid sequence having at least 80% homology thereof; and the LCDR3 comprises an amino acid sequence as set forth in SEQ ID NO: 48 or an amino acid sequence having at least 80% homology thereof. In certain embodiments, the light chain variable region comprises an amino acid sequence as set forth in SEQ ID NO: 50 or an amino acid sequence having at least 80% homology thereof. In certain embodiments, the antibody or antigen-binding fragment thereof comprises a heavy chain variable region including HCDR1-HCDR3, wherein the HCDR1 comprises an amino acid sequence as set forth in SEQ ID NO: 43 or an amino acid sequence having at least 80% homology thereof; the HCDR2 comprises an amino acid sequence as set forth in SEQ ID NO: 44 or an amino acid sequence having at least 80% homology thereof; and the HCDR3 comprises an amino acid sequence as set forth in SEQ ID NO: 45 or an amino acid sequence having at least 80% homology thereof. In certain embodiments, the heavy chain variable region comprises an amino acid sequence as set forth in SEQ ID NO: 49 or an amino acid sequence having at least 80% homology thereof.

In certain embodiments, the targeting moiety is an antibody or antigen-binding fragment thereof that specially binds to and/or recognizes BCMA, and the antibody or antigen-binding fragment thereof comprises a light chain variable region including LCDR1-LCDR3, wherein the LCDR1 comprises an amino acid sequence as set forth in SEQ ID NO: 54 or an amino acid sequence having at least 80% homology thereof; the LCDR2 comprises an amino acid sequence as set forth in SEQ ID NO: 55 or an amino acid sequence having at least 80% homology thereof; and the LCDR3 comprises an amino acid sequence as set forth in SEQ ID NO: 56 or an amino acid sequence having at least 80% homology thereof. In certain embodiments, the light chain variable region comprises an amino acid sequence as set forth in SEQ ID NO: 58 or an amino acid sequence having at least 80% homology thereof. In certain embodiments, the antibody or antigen-binding fragment thereof comprises a heavy chain variable region including HCDR1-HCDR3, wherein the HCDR1 comprises an amino acid sequence as set forth in SEQ ID NO: 51 or an amino acid sequence having at least 80% homology thereof; the HCDR2 comprises an amino acid sequence as set forth in SEQ ID NO: 52 or an amino acid sequence having at least 80% homology thereof; and the HCDR3 comprises an amino acid sequence as set forth in SEQ ID NO: 53 or an amino acid sequence having at least 80% homology thereof. In certain embodiments, the heavy chain variable region comprises an amino acid sequence as set forth in SEQ ID NO: 57 or an amino acid sequence having at least 80% homology thereof.

In certain embodiments, the targeting moiety is an antibody or antigen-binding fragment thereof that specially binds to and/or recognizes HER2, and the antibody or antigen-binding fragment thereof comprises a light chain variable region including LCDR1-LCDR3, wherein the LCDR1 comprises an amino acid sequence as set forth in SEQ ID NO: 70 or an amino acid sequence having at least 80% homology thereof; the LCDR2 comprises an amino acid sequence as set forth in SEQ ID NO: 71 or an amino acid sequence having at least 80% homology thereof; and the LCDR3 comprises an amino acid sequence as set forth in SEQ ID NO: 72 or an amino acid sequence having at least 80% homology thereof. In certain embodiments, the light chain variable region comprises an amino acid sequence as set forth in SEQ ID NO: 74 or an amino acid sequence having at least 80% homology thereof. In certain embodiments, the antibody or antigen-binding fragment thereof comprises a heavy chain variable region including HCDR1-HCDR3, wherein the HCDR1 comprises an amino acid sequence as set forth in SEQ ID NO: 67 or an amino acid sequence having at least 80% homology thereof; the HCDR2 comprises an amino acid sequence as set forth in SEQ ID NO: 68 or an amino acid sequence having at least 80% homology thereof; and the HCDR3 comprises an amino acid sequence as set forth in SEQ ID NO: 69 or an amino acid sequence having at least 80% homology thereof. In certain embodiments, the heavy chain variable region comprises an amino acid sequence as set forth in SEQ ID NO: 73 or an amino acid sequence having at least 80% homology thereof.

In certain embodiments, the targeting moiety is an antibody or a fragment for antigen-binding thereof that specially binds to and/or recognizes Mesothelin, and the antibody or antigen-binding fragment thereof comprises a light chain variable region including LCDR1-LCDR3, wherein the LCDR1 comprises an amino acid sequence as set forth in SEQ ID NO: 62 or an amino acid sequence having at least 80% homology thereof; the LCDR2 comprises an amino acid sequence as set forth in SEQ ID NO: 62 or an amino acid sequence having at least 80% homology thereof; and the LCDR3 comprises an amino acid sequence as set forth in SEQ ID NO: 64 or an amino acid sequence having at least 80% homology thereof. In certain embodiments, the light chain variable region comprises an amino acid sequence as set forth in SEQ ID NO: 66 or an amino acid sequence having at least 80% homology thereof. In certain embodiments, the antibody or antigen-binding fragment thereof comprises a heavy chain variable region including HCDR1-HCDR3, wherein the HCDR1 comprises an amino acid sequence as set forth in SEQ ID NO: 59 or an amino acid sequence having at least 80% homology thereof; the HCDR2 comprises an amino acid sequence as set forth in SEQ ID NO: 60 or an amino acid sequence having at least 80% homology thereof; and the HCDR3 comprises an amino acid sequence as set forth in SEQ ID NO: 61 or an amino acid sequence having at least 80% homology thereof. In certain embodiments, the heavy chain variable region comprises an amino acid sequence as set forth in SEQ ID NO: 65 or an amino acid sequence having at least 80% homology thereof.

In certain embodiments, the targeting moiety is an antibody or antigen-binding fragment thereof that specially binds to and/or recognizes GPC3, and the antibody or antigen-binding fragment thereof comprises a light chain variable region including LCDR1-LCDR3, wherein the LCDR1 comprises an amino acid sequence as set forth in SEQ ID NO:38 or an amino acid sequence having at least 80% homology thereof; the LCDR2 comprises an amino acid sequence as set forth in SEQ ID NO: 39 or an amino acid sequence having at least 80% homology thereof; and the LCDR3 comprises an amino acid sequence as set forth in SEQ ID NO: 40 or an amino acid sequence having at least 80% homology thereof. In certain embodiments, the light chain variable region comprises an amino acid sequence as set forth in SEQ ID NO: 42 or an amino acid sequence having at least 80% homology thereof. In certain embodiments, the antibody or antigen-binding fragment thereof comprises a heavy chain variable region including HCDR1-HCDR3, wherein the HCDR1 comprises an amino acid sequence as set forth in SEQ ID NO: 35 or an amino acid sequence having at least 80% homology thereof the HCDR2 comprises an amino acid sequence as set forth in SEQ ID NO: 36 or an amino acid sequence having at least 80% homology thereof; and the HCDR3 comprises an amino acid sequence as set forth in SEQ ID NO: 37 or an amino acid sequence having at least 80% homology thereof. In certain embodiments, the heavy chain variable region comprises an amino acid sequence as set forth in SEQ ID NO: 41 or an amino acid sequence having at least 80% homology thereof.

In certain embodiments, the targeting moiety comprises an amino acid sequence as set forth in any one of SEQ ID NO: 2, 4, 6, 8, and 10 or an amino acid sequence having at least 80% homology thereof. In certain embodiments, a nucleic acid molecule encoding the targeting moiety comprises a nucleic acid sequence as set forth in any one of SEQ ID NO: 1, 3, 5, 7, and 9 or an amino acid sequence having at least 80% homology thereof.

In certain embodiments, the method further comprises the step of isolating and obtaining peripheral blood mononuclear cells PBMC, $CD3^+$T lymphocyte, $CD8^+$T lymphocyte, $CD4^+$T lymphocyte or regulatory T cells.

In certain embodiments, the method further comprises adding one or more T cell stimulatory factors into the isolated PBMC. In certain embodiments, the T cell stimulatory factors are selected from the group consisting of B lymphocyte surface antigens antibody, TNF antibody, intracellular polyester, and antibiotics. In certain embodiments, the T cell stimulatory factors are selected from the group consisting of CD3 antibody, CD28 antibody, 4-1BB antibody, CD80 antibody, CD86 antibody, PHA, PMA, and ionomycin.

In certain embodiments, the T cell stimulatory factors comprise CD3 antibody at a concentration of 1-10000 ng/mL. In certain embodiments, the T cell stimulatory factor comprise CD28 antibody at a concentration of 1-10000 ng/mL.

In certain embodiments, the method further comprises adding one or more cytokines into the isolated PBMC.

In certain embodiments, the cytokines comprise interleukins.

In certain embodiments, the interleukins comprise one or more selected from the group consisting of IL2, TL21, IL7, and TL15. In certain embodiments, the interleukins comprise IL2 at a concentration of 0.1-10000 U/mL. In certain embodiments, the interleukins comprise IL21 at a concentration of 0.01-1000 ng/mL. In certain embodiments, the interleukins comprise IL7 at a concentration of 0.01-1000 ng/mL. In certain embodiments, the interleukins comprise IL15 at a concentration of 0.01-1000 ng/mL.

In certain embodiments, the low density lipoprotein receptor-associated protein comprises one or more selected from the group consisting of the low density lipoprotein receptor-associated protein 1-12, and a functional fragment thereof. In certain embodiments, the low density lipoprotein receptor-associated protein or fragment thereof is derived from human.

In certain embodiments, the functional fragment comprises a fragment or Truncated protein of the low density lipoprotein receptor-associated protein with an activity of the low density lipoprotein receptor-associated protein. In certain embodiments, the low density lipoprotein receptor-associated protein comprises the low density lipoprotein receptor-associated protein 6 and its truncated protein, and/or the low density lipoprotein receptor-associated protein 5 and its truncated protein. In certain embodiments, the Truncated protein of the low density lipoprotein receptor-associated protein 6 comprises an intracellular region of the low density lipoprotein receptor-associated protein 6; and/or the Truncated protein of the low density lipoprotein receptor-associated protein 5 comprises an intracellular region of the low density lipoprotein receptor-associated protein 5. In certain embodiments, the Truncated protein of the low density lipoprotein receptor-associated protein 6 comprises a transmembrane region of the low density lipoprotein receptor-associated protein 6 and an LDLR region of the low density lipoprotein receptor-associated protein 6; and/or the Truncated protein of the low density lipoprotein receptor-associated protein 5 comprises a transmembrane region of the low density lipoprotein receptor-associated protein 5 and an LDLR region of the low density lipoprotein receptor-associated protein 5. In certain embodiments, the low density lipoprotein receptor-associated protein or fragment thereof comprises an amino acid sequence as set forth in any one of SEQ ID NO: 22, 24, 26, and 28 or an amino acid sequence having at least 80% homology thereof. In certain embodiments, a nucleic acid molecule encoding the low density lipoprotein receptor-associated protein or fragment thereof comprises a nucleic acid sequence as set forth in any one of SEQ ID NO: 21, 23, 25, and 27 or an amino acid sequence having at least 80% homology thereof.

In another aspect, the present application provides a genetically modified immune cell, wherein the genetic modification up-regulates an expression of the low density lipoprotein receptor-associated protein or fragment thereof in the immune cells.

In certain embodiments, the genetically modified immune cell comprises lymphocyte. In certain embodiments, the genetically modified immune cell comprises genetically modified T cells. In certain embodiments, the genetically modified immune cell comprises genetically modified memory stem cell-like T cells (TSCM) and/or genetically modified central memory T cells (TCM). In certain embodiments, the TSCM is CCR7$^+$ and/or CD62L$^+$. In certain embodiments, the TSCM further has one or more properties selected from the group consisting of CD45RA$^+$or CD45RA$^-$, CD45RO$^+$or CD45RO$^-$, CD27$^+$, CD28$^+$, CD127$^+$, CD122$^+$, CD3$^+$, CD4$^+$, and CD8$^+$.

In certain embodiments, the immune cell comprises genetically modified immune cells, and the genetically modified immune cells express a chimeric antigen receptor (CAR) or a T cell receptor (TCR).

In certain embodiments, the CAR comprises an intracellular domain, the intracellular domain comprises a signal transduction domain and/or a costimulatory domain. In certain embodiments, the signal transduction domain comprises a moiety selected from the group consisting of a signal transduction domain of CD3ζ, a signal transduction domain of CD3δ, and a signal transduction domain of CD3ε. In certain embodiments, the signal transduction domain comprises an amino acid sequence as set forth in SEQ ID NO: 18. In certain embodiments, a nucleic acid molecule encoding the signal transduction domain comprises a nucleic acid sequence as set forth in SEQ ID NO:17 or a nucleic acid sequence having at least 80% homology thereof.

In certain embodiments, the costimulatory domain comprises a moiety selected from the group consisting of a costimulatory domain of CD27, a costimulatory domain of CD28, and a costimulatory domain of 4-1BB. In certain embodiments, the costimulatory domain comprises an amino acid sequence as set forth in any one of SEQ ID NO:14, and SEQ ID NO:16 or an amino acid sequence having at least 80% homology thereof. In certain embodiments, a nucleic acid molecule encoding the costimulatory domain comprises a nucleic acid sequence as set forth in any one of SEQ ID NO:13, and SEQ ID NO:15 or a nucleic acid sequence having at least 80% homology thereof.

In certain embodiments, the CAR comprises a hinge region. In certain embodiments, the hinge region comprises a moiety selected from the group consisting of a hinge region of IgG4, a hinge region of IgG1, and a hinge region of CD8. In certain embodiments, the hinge region comprises an amino acid sequence as set forth in SEQ ID NO: 31 or an amino acid sequence having at least 80% homology thereof. In certain embodiments, a nucleic acid molecule encoding the hinge region comprises a nucleic acid sequence as set forth in SEQ ID NO: 32 or an amino acid sequence having at least 80% homology thereof.

In certain embodiments, the CAR comprises a transmembrane region. In certain embodiments, the transmembrane region comprises a moiety selected from the group consisting of a transmembrane region of CD8, a transmembrane region of CD28, and a transmembrane region of CD24. In certain embodiments, the transmembrane region comprises an amino acid sequence as set forth in SEQ ID NO: 33 or an amino acid sequence having at least 80% homology thereof. In certain embodiments, a nucleic acid molecule encoding the transmembrane region comprises a nucleic acid sequence as set forth in SEQ ID NO: 34 or a nucleic acid sequence having at least 80% homology thereof.

In certain embodiments, the CAR comprises a targeting moiety. In certain embodiments, the targeting moiety comprises ScFv. In certain embodiments, the targeting moiety specially binds to and/or recognizes tumor antigen. In certain embodiments, the targeting moiety specially binds to and/or recognizes a target selected from the group consisting of B lymphocyte surface antigens, TNF family members, HER family members, and GPC family members. In certain embodiments, the targeting moiety specially binds to and/or recognizes a target selected from the group consisting of CD19, BCMA, HER2, Mesothelin, and GPC3.

In certain embodiments, the targeting moiety is an antibody or antigen-binding fragment thereof that specially binds to and/or recognizes CD19, and the antibody or antigen-binding fragment thereof comprises a light chain variable region including LCDR1-LCDR3, wherein the LCDR1 comprises an amino acid sequence as set forth in SEQ ID NO: 46 or an amino acid sequence having at least 80% homology thereof; the LCDR2 comprises an amino acid sequence as set forth in SEQ ID NO: 47 or an amino acid sequence having at least 80% homology thereof; and the LCDR3 comprises an amino acid sequence as set forth in SEQ ID NO: 48 or an amino acid sequence having at least 80% homology thereof. In certain embodiments, the light chain variable region comprises an amino acid sequence as set forth in SEQ ID NO: 50 or an amino acid sequence having at least 80% homology thereof. In certain embodiments, the antibody or antigen-binding fragment thereof comprises a heavy chain variable region including HCDR1-HCDR3, wherein the HCDR1 comprises an amino acid sequence as set forth in SEQ ID NO: 43 or an amino acid sequence having at least 80% homology thereof; the HCDR2 comprises an amino acid sequence as set forth in SEQ ID NO: 44 or an amino acid sequence having at least 80% homology thereof; and the HCDR3 comprises an amino acid sequence as set forth in SEQ ID NO: 45 or an amino acid sequence having at least 80% homology thereof. In certain embodiments, the heavy chain variable region comprises an amino acid sequence as set forth in SEQ ID NO: 49 or an amino acid sequence having at least 80% homology thereof.

In certain embodiments, the targeting moiety is an antibody or antigen-binding fragment thereof that specially binds to and/or recognizes BCMA, and the antibody or antigen-binding fragment thereof comprises a light chain variable region including LCDR1-LCDR3, wherein the LCDR1 comprises an amino acid sequence as set forth in SEQ ID NO: 54 or an amino acid sequence having at least 80% homology thereof; the LCDR2 comprises an amino acid sequence as set forth in SEQ ID NO: 55 or an amino acid sequence having at least 80% homology thereof; and the LCDR3 comprises an amino acid sequence as set forth in SEQ ID NO: 56 or an amino acid sequence having at least 80% homology thereof. In certain embodiments, the light chain variable region comprises an amino acid sequence as set forth in SEQ ID NO: 58 or an amino acid sequence having at least 80% homology thereof. In certain embodiments, the antibody or antigen-binding fragment thereof comprises a heavy chain variable region including HCDR1-HCDR3, wherein the HCDR1 comprises an amino acid sequence as set forth in SEQ ID NO: 51 or an amino acid sequence having at least 80% homology thereof; the HCDR2 comprises an amino acid sequence as set forth in SEQ ID NO: 52 or an amino acid sequence having at least 80% homology thereof; and the HCDR3 comprises an amino acid sequence as set forth in SEQ ID NO: 53 or an amino acid sequence having at least 80% homology thereof. In certain embodiments, the heavy chain variable region comprises an amino acid sequence as set forth in SEQ ID NO: 57 or an amino acid sequence having at least 80% homology thereof.

In certain embodiments, the targeting moiety is an antibody or antigen-binding fragment thereof that specially binds to and/or recognizes HER2, and the antibody or antigen-binding fragment thereof comprises a light chain variable region including LCDR1-LCDR3, wherein the LCDR1 comprises an amino acid sequence as set forth in SEQ ID NO: 70 or an amino acid sequence having at least 80% homology thereof; the LCDR2 comprises an amino acid sequence as set forth in SEQ ID NO: 71 or an amino acid sequence having at least 80% homology thereof; and the LCDR3 comprises an amino acid sequence as set forth in SEQ ID NO: 72 or an amino acid sequence having at least 80% homology thereof. In certain embodiments, the light chain variable region comprises an amino acid sequence as set forth in SEQ ID NO: 74 or an amino acid sequence having at least 80% homology thereof. In certain embodiments, the antibody or antigen-binding fragment thereof comprises a heavy chain variable region including HCDR1-HCDR3, wherein the HCDR1 comprises an amino acid sequence as set forth in SEQ ID NO: 67 or an amino acid sequence having at least 80% homology thereof; the HCDR2 comprises an amino acid sequence as set forth in SEQ ID NO: 68 or an amino acid sequence having at least 80% homology thereof; and the HCDR3 comprises an amino acid sequence as set forth in SEQ ID NO: 69 or an amino acid sequence having at least 80% homology thereof. In certain embodiments, the heavy chain variable region comprises an amino acid sequence as set forth in SEQ ID NO: 73 or an amino acid sequence having at least 80% homology thereof.

In certain embodiments, the targeting moiety is an antibody or a fragment for antigen-binding thereof that specially binds to and/or recognizes Mesothelin, and the antibody or antigen-binding fragment thereof comprises a light chain variable region including LCDR1-LCDR3, wherein the LCDR1 comprises an amino acid sequence as set forth in SEQ ID NO: 62 or an amino acid sequence having at least 80% homology thereof; the LCDR2 comprises an amino acid sequence as set forth in SEQ ID NO: 63 or an amino acid sequence having at least 80% homology thereof; and the LCDR3 comprises an amino acid sequence as set forth in SEQ ID NO: 64 or an amino acid sequence having at least 80% homology thereof. In certain embodiments, the light chain variable region comprises an amino acid sequence as set forth in SEQ ID NO: 66 or an amino acid sequence having at least 80% homology thereof. In certain embodiments, the antibody or antigen-binding fragment thereof comprises a heavy chain variable region including HCDR1-HCDR3, wherein the HCDR1 comprises an amino acid sequence as set forth in SEQ ID NO: 59 or an amino acid sequence having at least 80% homology thereof; the HCDR2 comprises an amino acid sequence as set forth in SEQ ID NO: 60 or an amino acid sequence having at least 80% homology thereof; and the HCDR3 comprises an amino acid sequence as set forth in SEQ ID NO: 61 or an amino acid sequence having at least 80% homology thereof. In certain embodiments, the heavy chain variable region comprises an amino acid sequence as set forth in SEQ ID NO: 65 or an amino acid sequence having at least 80% homology thereof.

In certain embodiments, the targeting moiety is an antibody or antigen-binding fragment thereof that specially binds to and/or recognizes GPC3, and the antibody or antigen-binding fragment thereof comprises a light chain variable region including LCDR1-LCDR3, wherein the LCDR1 comprises an amino acid sequence as set forth in SEQ ID NO: 38 or an amino acid sequence having at least 80% homology thereof; the LCDR2 comprises an amino acid sequence as set forth in SEQ ID NO: 39 or an amino acid sequence having at least 80% homology thereof; and the LCDR3 comprises an amino acid sequence as set forth in SEQ ID NO:40 or an amino acid sequence having at least 80% homology thereof. In certain embodiments, the light chain variable region comprises an amino acid sequence as set forth in SEQ ID NO: 42 or an amino acid sequence having at least 80% homology thereof. In certain embodiments, the antibody or antigen-binding fragment thereof comprises a heavy chain variable region including HCDR1-HCDR3, wherein the HCDR1 comprises an amino acid sequence as set forth in SEQ ID NO: 35 or an amino acid sequence having at least 80% homology thereof; the HCDR2 comprises an amino acid sequence as set forth in SEQ ID NO: 36 or an amino acid sequence having at least 80% homology thereof; and the HCDR3 comprises an amino acid sequence as set forth in SEQ ID NO: 37 or an amino acid sequence having at least 80% homology thereof. In certain embodiments, the heavy chain variable region comprises an amino acid sequence as set forth in SEQ ID NO: 41 or an amino acid sequence having at least 80% homology thereof.

In certain embodiments, the targeting moiety comprises an amino acid sequence as set forth in any one of SEQ ID NO: 2, 4, 6, 8, and 10 or an amino acid sequence having at least 80% homology thereof. In certain embodiments, a nucleic acid molecule encoding the targeting moiety comprises a nucleic acid sequence as set forth in any one of SEQ ID NO: 1, 3, 5, 7, and 9 or a nucleic acid sequence having at least 80% homology thereof.

In certain embodiments, the low density lipoprotein receptor-associated protein comprises one or more selected from the group consisting of the low density lipoprotein receptor-associated protein 1-12, and a functional fragment thereof. In certain embodiments, the low density lipoprotein receptor-associated protein or fragment thereof is derived from human.

In certain embodiments, the functional fragment comprises a fragment or Truncated protein of the low density lipoprotein receptor-associated protein with an activity of the low density lipoprotein receptor-associated protein. In certain embodiments, the low density lipoprotein receptor-associated protein comprises the low density lipoprotein receptor-associated protein 6 and truncated protein thereof, and/or the low density lipoprotein receptor-associated protein 5 and truncated protein thereof. In certain embodiments, the Truncated protein of the low density lipoprotein receptor-associated protein 6 comprises an intracellular region of the low density lipoprotein receptor-associated protein 6; and/or the Truncated protein of the low density lipoprotein receptor-associated protein 5 comprises an intracellular region of the low density lipoprotein receptor-associated protein 5. In certain embodiments, the Truncated protein of the low density lipoprotein receptor-associated protein 6 comprises a transmembrane region of the low density lipoprotein receptor-associated protein 6 and an LDLR region of the low density lipoprotein receptor-associated protein 6; and/or the Truncated protein of the low density lipoprotein receptor-associated protein 5 comprises a transmembrane region of the low density lipoprotein receptor-associated protein 5 and an LDLR region of the low density lipoprotein receptor-associated protein 5. In certain embodiments, the low density lipoprotein receptor-associated protein or fragment thereof comprises an amino acid sequence as set forth in any one of SEQ ID NO: 22, 24, 26, and 28 or an amino acid sequence having at least 80% homology thereof. In certain embodiments, a nucleic acid molecule encoding the low density lipoprotein receptor-associated protein or fragment thereof comprises a nucleic acid sequence as set forth in any one of SEQ ID NO: 21, 23, 25, and 27 or a nucleic acid sequence having at least 80% homology thereof.

In another aspect, the present application provides a composition including the genetically modified immune cell.

In certain embodiments, the composition further optionally comprises a pharmaceutically acceptable carrier.

In another aspect, the present application provides use of the genetically modified cell and/or the composition in manufacture of a drug for treating and/or preventing tumors.

In certain embodiments, the tumor is selected from the group consisting of liver cancer, lung cancer, leukemia, and mesothelioma.

In another aspect, the present application provides a method for preparing the composition including a following step: up-regulating an expression of the low density lipoprotein receptor-associated protein or fragment thereof in the genetically modified immune cell.

In certain embodiments, the method comprises a following step: introducing a vector up-regulating an expression of the low density lipoprotein receptor-associated protein or fragment thereof into the genetically modified immune cell. In certain embodiments, the vector is selected from the group consisting of retroviral vector, lentiviral vector, and transposon plasmid.

In certain embodiments, the low density lipoprotein receptor-associated protein or fragment thereof comprises an amino acid sequence as set forth in any one of SEQ ID NO: 22, 24, 26, and 28 or an amino acid sequence having at least 80% homology thereof.

In certain embodiments, the genetically modified immune cell comprises lymphocyte. In certain embodiments, the genetically modified immune cell expresses a chimeric antigen receptor (CAR). In certain embodiments, the method comprises a following step: isolating and activating the genetically modified immune cell, wherein the activating comprises an application of a T cell medium to the isolated genetically modified immune cell.

In certain embodiments, the T cell medium is one or more selected from the group consisting of DMEM medium, 1640 medium, MEM medium, and X-VIVO medium.

In certain embodiments, the method further comprises the application of T cell stimulatory factors to the genetically modified immune cell.

Persons skilled in the art can readily recognize other aspects and advantages of the present disclosure from the detailed description as below. The detailed description below only shows and describes exemplary embodiments of the present application. As persons skilled in the art will appreciate, the content of the present disclosure enables persons skilled in the art to modify the disclosed embodiments without departing from the spirit and scope of the invention involved in the present application. Correspondingly, the accompanying drawings and the description in the specification of the present application are only exemplary, rather than limited.

BRIEF DESCRIPTION OF THE DRAWINGS

The particular features of the invention involved in the present application are as shown in the accompanying claims. With reference to the exemplary embodiments as detailedly described below and the accompanying drawings, the features and advantages of the invention involved in the present application can be better understood. The accompanying drawings are briefly described as follows:

FIG. 1 shows a schematic structural view of the CAR in the lentivirus according to the present application.

DETAILED DESCRIPTION OF THE EMBODIMENTS

Figure 2:
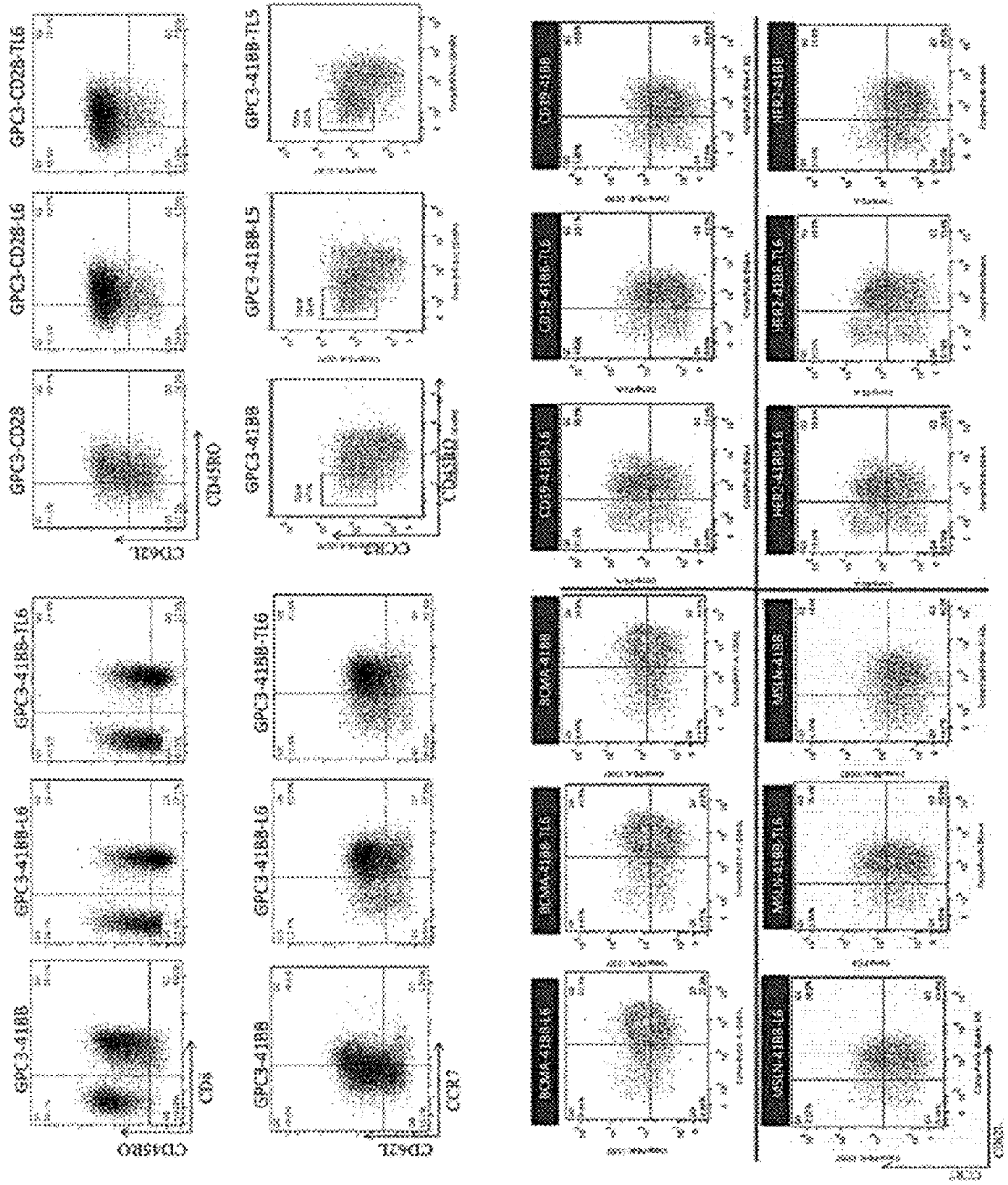
FIG. 2 shows a result of the genetically modified immune cell according to the present application for promoting the production of memory immune cells.

Hereinafter the embodiments of the present application are described by means of particular examples, and persons skilled in the art can readily understand other advantages and effects of the inventions as claimed in the present application based on the disclosure of the specification.

In the present application, the term "immune cell" generally refers to a cell involved in or associated with an immune response. The immune cell can comprise lymphocytes and a variety of phagocytes. The immune cells can further comprise naturally-occurring and genetically modified immune cells. In the present application, the genetically modified immune cell can express a chimeric antigen receptor (CAR). Of those, the lymphocyte can comprise T lymphocytes and B lymphocytes. In the present application, the immune cells can comprise T cells.

In the present application, the term "memory immune cells" generally refers to cells with immune memory. The immune memory can mean that a cell can produce a rapid and strong immune response when encountering a specific antigen to which it had produced a specific recognition and response. In the present application, the memory immune cells can comprise memory T cells. The memory T cells can be divided into memory stem cell-like T cells (TSCM) and central memory T cells (TCM).

In the present application, the term "differentiated immune cells" generally refers to immune cells with a certain degree of differentiation. For example, the differentiated immune cells can be T cells with a certain degree of differentiation. In the present application, the differentiated immune cells can be obtained by culturing the immune cells to a certain degree of differentiation. For example, the differentiated immune cells can comprise regulatory T cells (Treg).

In the present application, the term "regulatory T cells (Treg)" generally refers to a population of lymphocytes that negatively regulate the body's immune response. The molecular marker of the regulatory T cells can be a transcription factor, Foxp3$^+$ or CD127$^-$. In the present application, the regulatory T cells can be divided into two types, i.e., naturally-occurring or induced. Of those, the naturally-occurring species are CD4$^+$CD25$^+$ cells, and the induced species are $T_R1$ cells and $T_H3$ cells In the present application, the term "subject susceptible to a tumor" generally refers to a subject with an increased probability of developing a tumor as compared with an ordinary subject. For example, the subject susceptible to a tumor can be a subject that has been cured with tumor, but has the risk of metastasis and recurrence. The subject susceptible to a tumor can also be a subject that has been diagnosed with tumor risk factors. For example, the risk factors can comprise some gene mutations (including deletions, additions or substitutions) that have been proven to be associated with tumors. In the present application, the subject susceptible to a tumor can also be a subject of prolonged exposure to the carcinogenic environment. For example, the carcinogenic environment can comprise strong radiation, high concentration of carcinogen.

In the present application, the term "genetic modification" generally refers to a alteration or modification occurring at the level of genetic structure. For example, the genetic modification can be a modification at the level of gene, transcription and/or translation. Alternatively, the genetic modification can comprise a change of any genetic property in an organism (including its tissues, cells, DNAs, mRNAs or proteins and fragments thereof, etc.). The genetic modification can comprise enabling the organism to express a particular protein or fragments thereof. For example, the genetic modification can comprise enabling the organism to express a vector of a particular protein or fragment thereof.

In the present application, the term "T cells" are also known as T lymphocytes, which are a subtype of leukocytes and plays a central role in cell-mediated immune. T cells can be distinguished from other lymphocytes (e.g., B cells and natural killer cells) by the T cell receptor present in the surface of cells. In the present application, the T cells can comprise memory stem cell-like T cells (TSCM) and central memory T cells (TCM).

In the present application, the term "memory stem cell-like T cells (TSCM)" generally refers to those that are in the early stage of differentiation of memory T cells, have the characteristics of stem cells, and have relatively strong multi-directional differentiation potential. After responding to antigen stimulation, TSCM cells can differentiate into central memory T cells (TCM), effector memory T cells (TEM), and effector T cells (TEF).

In the present application, the term "central memory T cells (TCM)" generally refers to T cells with long-term memory generated by the antigen activation of Native T cells. The biomarkers of TCM can comprise CD62L$^+$ and CD45RO$^+$. The central memory T cells can pass through the lymphatic shield, return to the lymph nodes, and exist in a state of being activated by the antigen.

In the present application, the term "T cells receptor" is also generally known as "TCR", which generally refers to the molecular structure of T cells for specially recognizing and binding to the antigen peptide-MHC molecule. The T cell receptor can exist on the surface of T cells in the form of a complex with CD3 molecules. The TCR can be a heterodimer fixed on the cell membrane, most of them are composed of highly variable α subunits and β subunits linked by disulfide bonds, and a few of them are composed of γ and δ peptide chains. The TCR can comprise a variable region and a constant region, wherein the constant region can be close to the cell membrane, linking the transmembrane region and the end of the cell, while the variable region is responsible for recognizing the polypeptide/MHC complex.

In the present application, the term "chimeric antigen receptor" is also generally known as "CAR", and" generally refers to a fusion protein including an extracellular domain capable of binding to an antigen and at least one intracellular domain. In the present application, the CAR can comprise an intracellular domain, and the intracellular domain comprises a signal transduction domain and/or a costimulatory domain. In the present application, a set of polypeptides of the CAR can be located in the same polypeptide chain (for example, including a chimeric fusion protein), or they can be discontinuous with each other, e.g., they can be located in different polypeptide chains. In the present application, the signals involved in induction can be transduced into the cytoplasm of T cells via CD3 and chains. In the present application, the intracellular domain can comprise a primary signal transduction binding domain (for example, the main signal domain of CD3-zeta (ζ)). In one aspect, the cytoplasmic signal domain can further comprise one or more costimulatory domains derived from at least one costimulatory molecule. For example, the costimulatory domain can be 4-1BB (i.e., CD137), CD27, ICOS and/or CD28. In the present application, the CAR can comprise a chimeric fusion protein, e.g., an optional leader sequence on the amino terminal (N-ter). Of those, the leader sequence optionally cleaves the antigen binding domain (e.g., ScFv), and localizes the CAR on the cell membrane during cell processing.

In the present application, the term "signal transduction domain" generally refers to a domain located inside a cell and capable of transducing signals. In the present application, the intracellular signal transduction domain can transduce signals into the cell. For example, the intracellular signal transduction domain is an intracellular signaling domain of the chimeric antigen receptor. In the present application, the signal transduction domain can comprise a moiety selected from the group consisting of CD3ζ, CD3δ, and a signal transduction domain of CD3ε.

In the present application, the term "costimulatory domain" generally refers to a domain in the CAR that passes through the cell membrane, and is linked to the intracellular signal transduction domain and serves to transmitting signals. In the present application, the costimulatory domain can comprise a moiety selected from the group consisting of CD27, CD28, and a costimulatory domain of 4-1BB.

In the present application, the term "hinge region" generally refers to a junction region between an antigen binding region and an immune cell Fc receptor (FcR) binding region. For example, the hinge region can be a region between the heavy chain CH1 and CH2 of an immunoglobulin. In the present application, the hinge region can be a region located between scFv and T cell membrane. The hinge region can be derived from IgG1 or IgG4, and can also be derived from IgD or CD8. In the present application, a hinge region can comprise a moiety selected from the group consisting of a hinge region of IgG4, a hinge region of IgG1, and a hinge region of CD8.

In the present application, the term "transmembrane region" generally refers to a transmembrane region linking the extracellular antigen binding domain and the intracellular signal domain, which is generally composed of dimeric membrane proteins, comprises primarily CD3ζ, CD4, CD8, CD28, and the like, and can anchor the CAR structure on a T cell membrane. Different designs of the transmembrane region can affect the expression of the introduced CAR gene. In the present application, the transmembrane region can comprise a moiety selected from the group consisting of a transmembrane region of CD8, a transmembrane region of CD28, and a transmembrane region of CD24.

In the present application, the term "single chain antibody" (ScFv)" generally refers to an antibody formed by linking the heavy chain variable region and the light chain variable region via a linker. In the present application, the linker can be a linker peptide.

In the present application, the term "tumor antigen" generally refers to an antigenic substance present in or generated by a tumor cell that can have an ability of triggering an immune response in a host. For example, the tumor antigen can be protein, polypeptide, peptide, or fragment thereof that constitutes a part of the tumor cell and can induce tumor-specific cytotoxic T lymphocytes. In some embodiments, the term "tumor antigen" can also refer to cancer cell-associated biomolecules (e.g., proteins, carbohydrates, glycoproteins, etc.) that are specifically or preferentially or differentially expressed on tumor cells so as to provide cancer preferential or specific targets. For example, as compared with any other cells in the organism, the preferential expression can be a conventional preferential expression, or a preferential expression in a specific area of the organism (e.g., in particular organs or tissues). In the present application, the tumor antigen can comprise B lymphocyte surface antigens, TNF family members, HER family members, and GPC family members.

In the present application, the term "B lymphocyte surface antigen" generally refers to an antigen generated by a B lymphocyte during different phases and located on the surface of the B lymphocyte. For example, the B lymphocyte surface antigen can comprise CD10, CD19, CD20, CD21, CD22, CD23, CD24, CD37, CD38, CD39, and CD40. In the present application, B lymphocyte surface antigens can comprise CD19.

In the present application, the term "CD19" generally refers to the differentiation group 19 protein, which is an antigen determinant that can be detected on leukemia precursor cells. The accession number of human CD19 in UniProt/Swiss-Prot is P15391, and the accession number of the nucleotide sequence encoding human CD19 in GenBank is NM_001178098. In the present application, CD19 can also comprise a mutant protein or a functional fragment thereof, e.g., the point mutant, fragments, insertions, deletions, and splice variants of full-length wild-type CD19.

In the present application, the term "TNF family members" generally refers to a member belonging to the TNF (Tumor Necrosis Factor) family. TNF family members can comprise CD40LG (TNFSF5), CD70 (TNFSF7), EDA, FASLG (TNFSF6), LTA (TNFSF1), LTB (TNFSF3), TNFSF4 (OX40L), TNFSF8 (CD153), TNFSF9 (4-1BB), TNFSF10 (TRAIL), TNFSF11 (RANKL), TNF SF12 (TWEAK), TNFSF13, TNFSF13B, TNFSF14, TNF SF15, TNFSF17 (BCMA), and TNFSF18. In the present application, the TNF family members can comprise BCMA and 4-1BB.

In the present application, the term "BCMA" generally refers to B Cell Maturation Antigen (BCMA, CD269). BCMA is a member of the tumor necrosis factor receptor (TNF) superfamily, and can bind to B cell activating factor (BAFF) and proliferation-inducing ligand (APRIL). BCMA is commonly found on the surface of plasma cells in patients with multiple myeloma. The accession number of human BCMA in GenBank is BAB60895.1.

The term "CD137 protein", also known as 4-1BB or TNFRS9, generally refers to a transmembrane protein of the tumor necrosis factor receptor superfamily (TNFRS). It is an activation-induced costimulatory molecule and an important modulator of immune response.

Studies have shown that CD137 agonistic monoclonal antibodies increase the expression of costimulatory molecules in many models, and significantly enhance cytolytic T lymphocyte responses and exert anti-tumor effects (see Vinay, Dass S., and Byoung S. Kwon. "4-1BB (CD137), an inducible costimulatory receptor, as a specific target for cancer therapy." BMB reports 47.3 (2014): 122). The accession number of human CD137 in GenBank is NP_001552.2.

In the present application, the term "HER family member" generally refers to a member belonging to the HER (human epidermal growth factor receptor) family. HER family members can comprise EGFR (ErbB-1), HER2/c-neu (ErbB-2), Her3 (ErbB-3), and Her4 (ErbB-4). In the present application, the HER family member can comprise HER2.

In the present application, the term "HER2" generally refers to a human HER2 protein, which belongs to a member of the HER family. For example, see Semba et al., PNAS (USA) 82: 6497-6501 (1985) and Yamamoto et al., Nature 319: 230-234 (1986). The GenBank accession number of human HER2 can comprise XP_024306409.1.

In the present application, the term "GPC family member" generally refers to glypican. There are six types of glypicans identified in mammals, which are referred to as GPC1 to GPC6, respectively. Glypicans are abnormally expressed in cancers, including human hepatocellular carcinoma, ovarian cancer, mesothelioma, pancreatic cancer, glioma and breast cancer. In the present application, the GPC family member can comprise GPC3.

In the present application, the term "GPC3" generally refers to a protein encoded by glypican 3 (NCBI database gene ID: 2719), which is an early marker of liver cancer. GPC3 is highly expressed in hepatocellular carcinoma, and can be detected in tissues of patients with early hepatocellular carcinoma. The GenBank accession number of human GPC3 can be AAB87062.1.

In the present application, the term "Mesothelin (or briefly MSLN)" generally refers to a tumor differentiation antigen, which is generally present on the mesothelial cells lining the pleura, peritoneum, and pericardium. It is highly expressed in cancers, including malignant mesothelioma, pancreatic cancer, ovarian cancer, and lung adenocarcinoma. The GenBank accession number of human Mesothelin can be AAH09272.1.

In the present application, the term "peripheral blood mononuclear cell (PBMC)" generally refers to cells with mononuclear nudei in peripheral blood. The peripheral blood mononuclear cells can comprise lymphocytes and monocytes. In the present application, the peripheral blood mononuclear cells can be separated using Ficoll-hypaque (dextran-meglumine diatrizoate) density gradient centrifugation method according to the specific gravity difference of various components in the blood.

In the present application, the term "T cell activating factor" generally refers to a substance that promotes the activation and proliferation of T cells. In the present application, the T cell activating factor can comprise B lymphocyte surface antigen antibodies, TNF antibodies, intracellular polyesters and/or antibiotics. In the present application, the T cell stimulating factor can be selected from the following group: CD3 antibody, CD28 antibody, 4-1BB antibody, CD80 antibody, CD86 antibody, PHA, PMA, and ionomycin.

In the present application, the term "B lymphocyte surface antigen antibody" generally refers to an antibody that specifically binds to the surface antigen of B lymphocyte. In the present application, B lymphocyte surface antigen antibodies can comprise CD3 antibodies, CD28 antibodies, CD80 antibodies, and CD86 antibodies.

In the present application, the term "TNF antibody" generally refers to an antibody that specifically binds to a member of the TNF family. In the present application, the TNF antibody can comprise 4-1BB antibody.

In the present application, the term "intracellular polyester" generally refers to a naturally occurring polymeric biomaterial synthesized by microorganisms and present in the form of inclusion bodies in cells. Intracellular polyester has good biological properties. In the present application, the intracellular polyester can comprise polyhydroxyalkanoate (PHA).

In the present application, the term "antibiotic" generally refers to a metabolite produced by microorganisms, animals or plants that has anti-pathogenic or other activities and can interfere with the development and functionization of other living cells. In the present application, the antibiotics can comprise β-lactams, aminoglycosides, amido alcohols, macrolides, polypeptides, nitroimidazoles and tetracyclines. For example, the antibiotic can comprise ionomycin.

In the present application, the term "PHA" generally refers to polyhydroxy fatty acid esters, which belong to intracellular polyesters synthesized by various bacteria, and can exist in the form of discontinuous inclusion bodies in the cytoplasm in vivo. PHA can have physical and chemical properties similar to synthetic plastics, as well as biodegradability, biocompatibility, optical activity, piezoelectricity, and gas barrier properties.

In the present application, the term "PMA" generally refers to propylene glycol methyl ether acetate (Phorbol-12-myristate-13-acetate).

In the present application, the term "CD3 antibody" generally refers to an antibody or antigen-binding fragment thereof that specifically binds to CD3. CD3 can be an important differentiation antigen on the T cell membrane and can transmit the signal of T cell activation. The CD3 antibody can be huOKT3g1 or HuM291.

In the present application, the term "CD28 antibody" generally refers to an antibody or antigen-binding fragment thereof that specifically binds to CD28. Human CD28 is located at 2q33 and has similar exons and introns to CTLA4. The ligands of the two are the B7 family, including B7-1 (CD80) and B7-2 (CD86).

In the present application, the term "cytokine" generally refers to a class of small molecular proteins that are synthesized and secreted by immune cells (e.g., monocytes, macrophages, T cells, B cells, NK cells, etc.) and some non-immune cells (endothelial cells, epidermal cells, fibroblasts, etc.) under stimulus and have broadly biological activities. The cytokines can have various functions such as regulating innate immunity and adaptive immunity, hematogenesis, cell growth, APSC pluripotent cells, and repairing damaged tissues. In the present application, the cytokines can comprise interleukins, interferons, tumor necrosis factor superfamily, colony stimulating factors, chemokines, and growth factors. For example, the cytokine can be an interleukin.

In the present application, the term "interleukin" generally refers to secreted proteins or signal molecules that can promote the development and differentiation of T and/or B lymphocytes and/or hematopoietic cells. Interleukins can be synthesized by helper CD4T lymphocytes, as well as by monocytes, macrophages and endothelial cells. In the present application, the term "interleukin" can comprise full-length interleukins or fragments (for example, Truncated proteins) or variants thereof, which substantially retain the biological activity of the corresponding wild-type interleukin (e.g., having a biological activity of at least 80%, at least 90%, at least 95%, at least 98%, at least 99%, or even at least 100% of the biological activity of the corresponding wild-type interleukin). The interleukin as used herein can be from any mammalian species. In certain embodiments, the interleukin is from a species selected from humans, horses, cattle, mice, pigs, rabbits, cats, dogs, rats, goats, sheep, and non-human primates. In certain embodiments, the interleukin can be a mutant form. For example, in the present application, the cytokine comprises one or more selected from the group consisting of IL2, IL21, IL7 and IL15.

In the present application, the term "IL2" generally refers to the T cell growth factor, TCGF. It is produced by T cells and exerts benefits in an autocrine and paracrine manner. It can activate T cells and promote the production of cytokines, stimulate the proliferation of NK cells and induce the production of LAK cells, promote the proliferation of B cells and secrete antibodies, and can also activate macrophages.

In the present application, the term "IL21" is homologous in spatial structure with IL-2, IL-4, and IL-15, and can generally promote the proliferation and differentiation of bone marrow NK cells, and synergistically stimulate the proliferation of B cells with anti-CD40 antibodies, and synergistically stimulate the proliferation of T cells with anti-CD3 antibody.

In the present application, the term "IL7" generally refers to a glycoprotein secreted by bone marrow stromal cells, and its gene is located on chromosome 8. The target cells of IL7 are lymphocytes, especially capable of promoting the growth of B progenitor cells, thymocytes and peripheral mature T cells from human or mouse bone marrow. At higher concentrations, IL-7 can also enhance the cytotoxic activity of macrophages and induce monocytes to secrete cytokines.

In the present application, the term "lL15" generally refers to the production of a variety of cells, such as activated monocytes-macrophages, epidermal cells and fibroblasts, and has many similarities with IL2. IL15 is a member of the IL2 family. It regulates the activation and proliferation of T and NK cells by changing the expression of Bcl-1 family members (such as Bcl-2 and Bcl-XL), and can also induce B cell proliferation.

In the present application, the term "low density lipoprotein receptor-related protein" (LRP) generally refers to an intrinsic protein containing 839 amino acids (by removing 21 amino acid signal peptides). It is embedded in the outer phospholipid layer of LDL (Low density lipoprotein) particles, and belongs to an endocytic receptor that can mediate the endocytosis of cholesterol-rich LDL. It is a member of the low density lipoprotein receptor (LDLR) gene family. The LRP is most prominently expressed in bronchial epithelial cells and adrenal and cortical tissues. In the present application, the low-density lipoprotein receptor-related protein can comprise one or more selections from the group consisting of low-density lipoprotein receptor-related proteins 1-12 or a Truncated protein thereof.

In the present application, the terms "low density lipoprotein receptor-related protein 6" (LRP-6) and "low density protein receptor-related protein 5" (LRP-5) generally refer to unique subgroups of the low density lipoprotein receptor (LDLR) family. The accession number of human LRP-6 in UniProt is O75581. The accession number of human LRP-5 in UniProt is 075197.

In the present application, the term "truncated protein" generally refers to a truncated protein. The truncated protein can be obtained by proteolysis or by manipulating the structural gene to eliminate the N- or C-terminal of a protein. Alternatively, the truncated protein can be obtained by prematurely terminating translation due to the presence of a stop codon in the structural gene caused by a nonsense mutation.

In the present application, the term "intracellular region" generally refers to a domain of protein located inside the cell membrane. In the present application, the intracellular domain can refer to a domain of the low density lipoprotein receptor-associated protein in the cell membrane. In the present application, the intracellular region can comprise the sequence from site 24 to site 243 in SEQ NO. 24 or an amino acid sequence having at least 80% homology thereof, or comprise the sequence from site 24 to site 231 in SEQ NO. 28 or an amino acid sequence having at least 80% homology thereof.

In the present application, the term "transmembrane region" generally refers to a domain of protein located across the cell membrane. In the present application, the transmembrane region can refer to a domain of the low density lipoprotein receptor-associated protein located across the cell membrane. The transmembrane region can consist of 23 hydrophobic amino acids. This domain primarily provides an anchoring function for the binding of LDLR on the cell membrane. In the present application, the transmembrane region can comprise the sequence from site 1 to site 23 in SEQ NO. 24 or an amino acid sequence having at least 80% homology thereof, or the sequence from site 1 to site 23 in SEQ NO. 28 or an amino acid sequence having at least 80% homology thereof.

In the present application, the term "LDLR region" generally refers to a domain of the low-density lipoprotein receptor-related protein close to the N segment outside the transmembrane region. This domain can have a function of enhancing Wnt signal. In the present application, the LDLR region can comprise the sequence from site 5 to site 119 in SEQ NO. 22 or an amino acid sequence having at least 80% homology thereof, or the sequence from site 4 to site 119 in SEQ NO. 26 or an amino acid sequence having at least 80% homology thereof.

In the present application, the term "ribosome skip site" is also called internal ribosome entry site (IRES), and generally refers to a nucleotide sequence located in the middle of the mRNA sequence for translation initiation. The ribosome skip site can allow initiation of translation in a cap-independent manner. IRES is generally located in the 5′UTR. In the present application, the ribosome skip site can comprise the sequence from site 1 to site 578 in SEQ NO. 29.

In the present application, the term "2A sequence" generally refers to a self-cleaving amino acid sequence that does not rely on protease. The 2A sequence can facilitate transcription to produce two proteins. In the present application, the 2A sequence can comprise the sequence from site 1 to site 54 in SEQ NO. 75.

In the present application, the term "pharmaceutically acceptable carrier" can comprise buffers, antioxidants, preservatives, low molecular weight polypeptides, proteins, hydrophilic polymers, amino acids, sugars, chelating agents, counter ions, metal complexes and/or non-ionic surfactants, etc.

In the present application, the term "retroviral vector" generally refers to an RNA virus that can be subject to reverse transcription in infected cells to produce a complementary DNA strand, and use the single DNA strand as a template to synthesize a second DNA strand which is then incorporated into the cell genomic DNA. The retroviral vector can use enzymes in the host cell to transcribe and replicate RNA to synthesize protein by itself, and then package the viruses which are released from the cell and become infectious viruses. The retrovirus has high transduction efficiency and can effectively increase the gene transfection rate.

In the present application, the term "lentiviral vector" refers to a gene therapeutic vector developed on the basis of HIV-1 (Human Immunodeficiency Type I Virus). The lentiviral vector can infect both dividing cells and non-dividing cells. It can effectively infect almost all mammalian cells including neuronal cells and hepatocytes with high infection efficiency. Lentivirus can effectively integrate foreign genes into the host chromosome to achieve persistent expression.

In the present application, the term "transposon plasmid" generally refers to a basic unit that exists on chromosomal DNA and can autonomously replicate and shift. The transposon plasmid can "jump" from one site to another in the genome through a series of processes such as cutting and reintegration.

In the present application, the term "tumor" generally refers to a neogrowth formed by a certain cell in a local tissue of an organism which loses the normal regulation for its growth at the level of gene under various carcinogenic factors, thereby resulting in its clonal abnormal proliferation. Such neogrowth is also called neoplasm because it is mostly presented as a space-occupying massive protrusion. In the present application, the tumor can comprise solid tumors and non-solid tumors. In the present application, the tumor can comprise liver cancer, lung cancer, leukemia and mesothelioma.

In the present application, the term "significant(ly) increase" generally refers to an increase in levels (e.g., protein expression, cell number), $P<0.05$, $P<0.04$, $P<0.03$, $P<0.02$, $P<0.01$, $P<0.005$ or $P<0.001$. Alternatively, the significant increase can refer to an increase of 5% or more, 10% or more, 20% or more, 30% or more, 40% or more, 50% or more, 60% or more, 70% or more, 80% or more, 90% or more, 100% or more.

In the present application, the term "substantial(ly) no increase" generally means that the level (e.g., protein expression, cell number) is the same as the original, or increased by 3% or less, increased by 2% or less, increased by 1% or less, increased by 0.5% or less, increased by 0.4% or less, increased by 0.3% or less, increased by 0.2% or less, increased by 0.1% or less.

In the present application, the term "about" generally refers to variations within a range of the specified value ±0.5-10%, e.g., a variation within a range of the specified value ±0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10%.

Low Density Lipoprotein Receptor-Associated Protein or Fragment Thereof

In the present application, the low density lipoprotein receptor-associated protein can comprise one or more selections from the group consisting of the low density lipoprotein receptor-associated protein 1-12, and a functional fragment thereof.

In the present application, the low density lipoprotein receptor-associated protein or fragment thereof can be derived from mammals, for example, can be derived from human, macaque, rat, and mouse.

In the present application, the functional fragment can comprise a fragment or Truncated protein of the low density lipoprotein receptor-associated protein with an activity of the low density lipoprotein receptor-associated protein. For example, the low density lipoprotein receptor-associated protein can comprise the low density lipoprotein receptor-associated protein 6 and truncated protein thereof, and/or the low density lipoprotein receptor-associated protein 5 and truncated protein thereof.

In the present application, the Truncated protein of the low density lipoprotein receptor-associated protein 6 can comprise an intracellular region of the low density lipoprotein receptor-associated protein 6; and/or the truncated protein of the low density lipoprotein receptor-associated protein 5 can comprise the intracellular region of the low density lipoprotein receptor-associated protein 5. Alternatively, the Truncated protein of the low density lipoprotein receptor-associated protein 6 can comprise a transmembrane region of the low density lipoprotein receptor-associated protein 6 and an LDLR region of the low density lipoprotein receptor-associated protein 6; and/or the truncated protein of the low density lipoprotein receptor-associated protein 5 can comprise a transmembrane region of the low density lipoprotein receptor-associated protein 5 and an LDLR region of the low density lipoprotein receptor-associated protein 5.

In the present application, the low density lipoprotein receptor-associated protein or fragment thereof comprises an amino acid sequence as set forth in any one of SEQ ID NO: 22, 24, 26, and 28 or an amino acid sequence having at least 80% homology thereof.

In the present application, a nucleic acid molecule encoding the low density lipoprotein receptor-associated protein or fragment thereof comprises a nucleic acid sequence as set forth in any one of SEQ ID NO: 21, 23, 25, and 27 or a nucleic acid sequence having at least 80% homology thereof.

Genetically Modified Immune Cells

The present application provides a genetically modified immune cell, wherein the expression of the low density lipoprotein receptor-associated protein or fragment thereof is upregulated in the immune cell.

In the present application, the genetically modified immune cell can comprise lymphocyte. In the present application, the genetically modified immune cell comprises genetically modified T cells. In the present application, the genetically modified immune cell comprises genetically modified memory stem cell-like T cells (TSCM) and/or genetically modified central memory T cells (TCM). In the present application, the TSCM comprises CCR7' and/or CD62L$^+$. In the present application, the TSCM can further have one or more properties selected from the group consisting of CD45RA$^+$ or CD45RA$^-$, CD45RO$^+$ or CD45RO$^-$, CD27$^+$, CD28$^+$, CD127$^+$, CD122$^+$, CD3$^+$, CD4$^{+,\ and\ CD}$8$^+$.

In the present application, the immune cells can comprise genetically modified immune cells, and the genetically modified immune cells express chimeric antigen receptor (CAR).

In the present application, the CAR can comprise an intracellular domain, and the intracellular domain can comprise a signal transduction domain and/or a costimulatory domain.

For example, the signal transduction domain can comprise a moiety selected from the group consisting of a signal transduction domain of CD3ζ, a signal transduction domain of CD3δ, and a signal transduction domain of CD3ε. For example, the signal transduction domain can comprise an amino acid sequence as set forth in SEQ ID NO: 18 or an amino acid sequence having at least 80% homology thereof, a nucleic acid molecule encoding the signal transduction domain can comprise a nucleic acid sequence as set forth in SEQ ID NO:17 or a nucleic acid sequence having at least 80% homology thereof.

For example, the costimulatory domain can comprise a moiety selected from the group consisting of a costimulatory domain of CD27, a costimulatory domain of CD28, and a costimulatory domain of 4-1BB. For example, the costimulatory domain can comprise an amino acid sequence as set forth in any one of SEQ ID NO:14, and SEQ ID NO:16 or an amino acid sequence having at least 80% homology thereof, a nucleic acid molecule encoding the costimulatory domain can comprise a nucleic acid sequence as set forth in any one of SEQ ID NO:13, and SEQ ID NO:15 or a nucleic acid sequence having at least 80% homology thereof.

In the present application, the CAR can comprise a hinge region. For example, the hinge region can comprise a moiety selected from the group consisting of a hinge region of IgG4, a hinge region of IgG1, and a hinge region of CD8. For example, the hinge region can comprise an amino acid sequence as set forth in SEQ ID NO: 31 or an amino acid sequence having at least 80% homology thereof, a nucleic acid molecule encoding the hinge region can comprise a nucleic acid sequence as set forth in SEQ ID NO: 32 or a nucleic acid sequence having at least 80% homology thereof.

In the present application, the CAR can comprise a transmembrane region. For example, the transmembrane region can comprise a moiety selected from the group consisting of a transmembrane region of CD8, a transmembrane region of CD28, and a transmembrane region of CD24. For example, the transmembrane region can comprise an amino acid sequence as set forth in SEQ ID NO: 33 or an amino acid sequence having at least 80% homology thereof, a nucleic acid molecule encoding the transmembrane region can comprise a nucleic acid sequence as set forth in SEQ ID NO: 34 or a nucleic acid sequence having at least 80% homology thereof.

In the present application, the CAR can comprise a targeting moiety. In the present application, the targeting moiety can comprise antibody or antigen binding fragment. The antigen binding fragment can be selected from the group consisting of Fab, Fab', F(ab)2, F(ab')2, Fv, and ScFv fragments. For example, the targeting moiety can be ScFv.

In the present application, the targeting moiety can specially bind to and/or recognize tumor antigen. For example, the targeting moiety can specially bind to and/or recognize a target selected from the group consisting of B lymphocyte surface antigens, TNF family members, HER family members, and GPC family members. Alternatively, the targeting moiety can specially bind to and/or recognize a target selected from the group consisting of CD19, BCMA, HER2, Mesothelin, and GPC3.

In the present application, the targeting moiety can be an antibody or antigen-binding fragment thereof that specially binds to and/or recognizes CD19. The antibody or antigen-binding fragment thereof can comprise a light chain variable region, the light chain variable region can comprise LCDR1-LCDR3, wherein the LCDR1 can comprise an amino acid sequence as set forth in SEQ ID NO: 46 or an amino acid sequence having at least 80% homology thereof; the LCDR2 can comprise an amino acid sequence as set forth in SEQ ID NO: 47 or an amino acid sequence having at least 80% homology thereof; and the LCDR3 can comprise an amino acid sequence as set forth in SEQ ID NO: 48 or an amino acid sequence having at least 80% homology thereof. The light chain variable region can comprise an amino acid sequence as set forth in SEQ ID NO: 50 or an amino acid sequence having at least 80% homology thereof. In the present application, the antibody or antigen-binding fragment thereof can comprise a heavy chain variable region, the heavy chain variable region can comprise HCDR1-HCDR3, wherein the HCDR1 can comprise an amino acid sequence as set forth in SEQ ID NO: 43 or an amino acid sequence having at least 80% homology thereof; the HCDR2 can comprise an amino acid sequence as set forth in SEQ ID NO: 44 or an amino acid sequence having at least 80% homology thereof; and the HCDR3 can comprise an amino acid sequence as set forth in SEQ ID NO: 45 or an amino acid sequence having at least 80% homology thereof. The heavy chain variable region can comprise an amino acid sequence as set forth in SEQ ID NO: 49 or an amino acid sequence having at least 80% homology thereof.

In the present application, the targeting moiety is an antibody or antigen-binding fragment thereof that specially binds to and/or recognizes BCMA, the antibody or antigen-binding fragment thereof can comprise a light chain variable region, the light chain variable region can comprise LCDR1-LCDR3, wherein the LCDR1 can comprise an amino acid sequence as set forth in SEQ ID NO: 54 or an amino acid sequence having at least 80% homology thereof; the LCDR2 can comprise an amino acid sequence as set forth in SEQ ID NO: 55 or an amino acid sequence having at least 80% homology thereof; and the LCDR3 can comprise an amino acid sequence as set forth in SEQ ID NO: 56 or an amino acid sequence having at least 80% homology thereof. The light chain variable region can comprise an amino acid sequence as set forth in SEQ ID NO: 58 or an amino acid sequence having at least 80% homology thereof. In the present application, the antibody or antigen-binding fragment thereof can comprise a heavy chain variable region, the heavy chain variable region can comprise HCDR1-HCDR3, wherein the HCDR1 can comprise an amino acid sequence as set forth in SEQ ID NO: 51 or an amino acid sequence having at least 80% homology thereof; the HCDR2 can comprise an amino acid sequence as set forth in SEQ ID NO: 52 or an amino acid sequence having at least 80% homology thereof; and the HCDR3 can comprise an amino acid sequence as set forth in SEQ ID NO: 53 or an amino acid sequence having at least 80% homology thereof. The heavy chain variable region can comprise an amino acid sequence as set forth in SEQ ID NO: 57 or an amino acid sequence having at least 80% homology thereof.

In the present application, the targeting moiety is an antibody or antigen-binding fragment thereof that specially binds to and/or recognizes HER2, the antibody or antigen-binding fragment thereof can comprise a light chain variable region, the light chain variable region can comprise LCDR1-LCDR3, wherein the LCDR1 can comprise an amino acid sequence as set forth in SEQ ID NO: 70 or an amino acid sequence having at least 80% homology thereof; the LCDR2 can comprise an amino acid sequence as set forth in SEQ ID NO: 71 or an amino acid sequence having at least 80% homology thereof; and the LCDR3 can comprise an amino acid sequence as set forth in SEQ ID NO: 72 or an amino acid sequence having at least 80% homology thereof. The light chain variable region can comprise an amino acid sequence as set forth in SEQ ID NO: 74 or an amino acid sequence having at least 80% homology thereof. In the present application, the antibody or antigen-binding fragment thereof can comprise a heavy chain variable region, the heavy chain variable region can comprise HCDR1-HCDR3, wherein the HCDR1 can comprise an amino acid sequence as set forth in SEQ ID NO: 67 or an amino acid sequence having at least 80% homology thereof; the HCDR2 can comprise an amino acid sequence as set forth in SEQ ID NO: 68 or an amino acid sequence having at least 80% homology thereof", and the HCDR3 can comprise an amino acid sequence as set forth in SEQ ID NO: 69 or an amino acid sequence having at least 80% homology thereof. The heavy chain variable region can comprise an amino acid sequence as set forth in SEQ ID NO: 73 or an amino acid sequence having at least 80% homology thereof.

In the present application, the targeting moiety is an antibody or a fragment for antigen-binding thereof that specially binds to and/or recognizes Mesothelin, the antibody or antigen-binding fragment thereof can comprise a light chain variable region, the light chain variable region can comprise LCDR1-LCDR3, wherein the LCDR1 can comprise an amino acid sequence as set forth in SEQ ID NO: 62 or an amino acid sequence having at least 80% homology thereof; the LCDR2 can comprise an amino acid sequence as set forth in SEQ ID NO: 63 or an amino acid sequence having at least 80% homology thereof; and the LCDR3 can comprise an amino acid sequence as set forth in SEQ ID NO:64 or an amino acid sequence having at least 80% homology thereof. The light chain variable region can comprise an amino acid sequence as set forth in SEQ ID NO: 66 or an amino acid sequence having at least 80% homology thereof. The antibody or antigen-binding fragment thereof can comprise a heavy chain variable region, the heavy chain variable region can comprise HCDR1-HCDR3, wherein the HCDR1 can comprise an amino acid sequence as set forth in SEQ ID NO: 59 or an amino acid sequence having at least 80% homology thereof; the HCDR2 can comprise an amino acid sequence as set forth in SEQ ID NO: 60 or an amino acid sequence having at least 80% homology thereof; and the HCDR3 can comprise an amino acid sequence as set forth in SEQ ID NO: 61 or an amino acid sequence having at least 80% homology thereof. The heavy chain variable region can comprise an amino acid sequence as set forth in SEQ ID NO: 65 or an amino acid sequence having at least 80% homology thereof.

In the present application, the targeting moiety is an antibody or antigen-binding fragment thereof that specially binds to and/or recognizes GPC3, the antibody or antigen-binding fragment thereof can comprise a light chain variable region, the light chain variable region can comprise LCDR1-LCDR3, wherein the LCDR1 can comprise an amino acid sequence as set forth in SEQ ID NO: 38 or an amino acid sequence having at least 80% homology thereof; the LCDR2 can comprise an amino acid sequence as set forth in SEQ ID NO:39 or an amino acid sequence having at least 80% homology thereof, and the LCDR3 can comprise an amino acid sequence as set forth in SEQ ID NO: 40 or an amino acid sequence having at least 80% homology thereof. The light chain variable region can comprise an amino acid sequence as set forth in SEQ ID NO: 42 or an amino acid sequence having at least 80% homology thereof. In the present application, the antibody or antigen-binding fragment thereof can comprise a heavy chain variable region, the heavy chain variable region can comprise HCDR1-HCDR3, wherein the HCDR1 can comprise an amino acid sequence as set forth in SEQ ID NO: 35 or an amino acid sequence having at least 80% homology thereof; the HCDR2 can comprise an amino acid sequence as set forth in SEQ ID NO: 36 or an amino acid sequence having at least 80% homology thereof; and the HCDR3 can comprise an amino acid sequence as set forth in SEQ ID NO: 37 or an amino acid sequence having at least 80% homology thereof. The heavy chain variable region can comprise an amino acid sequence as set forth in SEQ ID NO: 41 or an amino acid sequence having at least 80% homology thereof.

In the present application, the targeting moiety can comprise an amino acid sequence as set forth in any one of SEQ ID NO: 2, 4, 6, 8, and 10 or an amino acid sequence having at least 80% homology thereof. In the present application, a nucleic acid molecule encoding the targeting moiety can comprise a nucleic acid sequence as set forth in any one of SEQ ID NO: 1, 3, 5, 7, and 9 or a nucleic acid sequence having at least 80% homology thereof.

In the present application, the start and end of the amino acid sites of the CDR are calculated in Kabat's way.

It is to be understood that the proteins, polypeptides, amino acid sequences and/or nucleic acid sequences involved in the present application also encompasses at least the followings: a variant or a homologue that has the same or similar functions as the proteins or polypeptides, and/or a nucleic acid sequence encoding the variant or homologue that has the same or similar functions as the proteins or polypeptides.

In the present application, the variant can be proteins or polypeptides obtained by substitution, deletion, or addition of one or more amino acids of the proteins and/or polypeptides (e.g., antibodies or fragments thereof that specifically bind to the GPC3 protein, or the low-density lipoprotein receptor-related protein or fragment thereof). For example, the functional variant can comprise a protein or polypeptide with amino acid changes caused by substitution, deletion and/or addition of at least 1 (e.g., 1-30, 1-20, or 1-10, alternatively, e.g., 1, 2, 3, 4, or 5) amino. The functional variant can substantially maintain the biological properties of the protein or polypeptide without change (e.g., substitution, deletion, or addition). For example, the functional variant can maintain at least 60%, 70%, 80%, 90%, or 100% of the biological activities of the protein or the polypeptide (e.g., antigen binding ability, or the biological functions of low-density lipoprotein receptor-related proteins or fragments thereof). For example, the substitution can be a conservative substitution.

In the present application, the homologue can be a protein or polypeptide that has at least 85% (e.g., at least about 85%, about 90%, about 91%, about 92%, about 93%, about 94%, about 95%, about 96%, about 97%, about 98%, about 99% or higher) sequence homology with the amino acid sequence of an antibody or fragment thereof (e.g., an antibody or fragment thereof that specifically binds to the GPC3 protein, or the low-density lipoprotein receptor-related protein or fragment thereof).

In the present application, the homology generally refers to the similarity, analogy or association between two or more sequences. The "percentage of sequence homology" can be calculated by means of comparing the two sequences to be aligned in a comparison window, and determining the number of sites at which the same nucleic acid bases (e.g., A, T, C, G, I) or the same amino acid residues (e.g., Ala, Pro, Ser, Thr, Gly, Val, Leu, Ile, Phe, Tyr, Trp, Lys, Arg, His, Asp, Glu, Asn, Gln, Cys and Met) are present so as to obtain the number of the matching sites; dividing the number of the matching sites by the total number of sites in the comparison window (i.e., the window size), and multiplying the result by 100 to give the percentage of sequence homology. The alignment to determine the percentage of sequence homology can be achieved in a variety of ways known in the art, e.g., by using a publicly available computer software such as BLAST, BLAST-2, ALIGN, or Megalign (DNASTAR) software. Those skilled in the art can determine the appropriate parameters for sequence alignment, including any algorithm required to achieve maximum alignment within the full-length sequence being compared or within the target sequence region. The homology can also be determined by the following methods: FASTA and BLAST. The description of FASTA algorithm can be found in W. R. Pearson and D. J. Lipman's "Improved Tool for Biological Sequence Comparison", Proc. Natl. Acad. Sci., 85: 2444-2448, 1988; and D. J. Lipman and W. R. Pearson's "Fast and Sensitive Protein Similarity Search", Science, 227:1435-1441, 1989. For the description of BLAST algorithm, please refer to S. Altschul, W. Gish, W. Miller, E. W. Myers and D. Lipman's "A Basic Local Alignment Search Tool", Journal of Molecular Biology, 215: 403-410, 1990.

In the present application, the CAR can comprise a targeting moiety, a hinge region, a transmembrane region, a costimulatory domain, and a signal transduction domain in order from N-terminal to C-terminal.

In the present application, the polynucleotide molecule encoding the CAR can comprise a nucleotide sequence encoding the targeting moiety, a nucleotide sequence encoding the hinge region, a nucleotide sequence encoding the transmembrane region, a nucleotide sequence encoding the transmembrane region, a nucleotide sequence encoding the costimulatory domain, and a nucleotide sequence encoding the signaling domain in order from 5'end to 3'end.

In the present application, the polynucleotide molecule encoding the CAR can further comprise a leader sequence. For example, the nucleic acid molecule encoding the leader sequence can comprise the nucleic acid sequence as set forth in SEQ ID NO: 30 or a nucleic acid sequence having at least 80% homology thereof. The nucleic acid molecule encoding the leader sequence can be located at the 5'end of the nucleotide sequence encoding the targeting moiety.

In the present application, the genetically modified immune cells can express the low-density lipoprotein receptor-related protein or fragments thereof. For example, the genetically modified immune cell can comprise a vector capable of expressing the low-density lipoprotein receptor-related protein or a fragment thereof. The vector can comprise nucleotide molecules encoding the low-density lipoprotein receptor-related protein or fragments thereof. For example, the polynucleotide molecule can comprise a nucleic acid sequence set forth in any one of the following: SEQ ID NO: 21, 23, 25, and 27 or a nucleic acid sequence having at least 80% homology thereof. Alternatively, the vector can be selected from the group consisting of retroviral vectors, lentiviral vectors and/or transposon plasmids.

In the present application, the genetically modified immune cell can express the chimeric antigen receptor (CAR). For example, the genetically modified immune cell can comprise a vector capable of expressing the chimeric antigen receptor (CAR). The vector can comprise a nucleotide molecule encoding the chimeric antigen receptor (CAR). Alternatively, the vector can be selected from the group consisting of retroviral vectors, lentiviral vectors and/or transposon plasmids.

In the present application, the vector capable of expressing the low-density lipoprotein receptor-related protein or fragment thereof and the vector capable of expressing the chimeric antigen receptor (CAR) can be the same or different vectors, as long as the one or more vectors can express the low-density lipoprotein receptor-related protein or fragments thereof and the chimeric antigen receptor (CAR), so that the genetically modified immune cells have both the low-density lipoprotein receptor-related protein or fragment thereof and the chimeric antigen receptor (CAR).

For example, the vector capable of expressing the low-density lipoprotein receptor-related protein or fragment thereof and the vector capable of expressing the chimeric antigen receptor (CAR) can be the same vector. In this vector, the nucleotide molecule encoding the low-density lipoprotein receptor-related protein or fragment thereof and the nucleotide molecule encoding the chimeric antigen receptor (CAR) can be located in the same expression box. For example, the nucleotide molecule encoding the low-density lipoprotein receptor-related protein or a fragment thereof can be located at the 3'end of the nucleotide molecule encoding the chimeric antigen receptor (CAR).

In the present application, the nucleotide molecule encoding the low-density lipoprotein receptor-related protein or fragment thereof can be directly or indirectly linked to the nucleotide molecule encoding the chimeric antigen receptor (CAR). For example, the indirect linking can be a linking via a linker sequence. The 5'end of the linker sequence can be linked to the 3'end of the nucleotide molecule encoding the low-density lipoprotein receptor-related protein or fragment thereof, and the 3'end of the linker sequence can be linked to the 5'end of the nucleotide molecule encoding the chimeric antigen receptor (CAR). In the present application, the linker sequence can comprise the nucleic acid sequence set forth in any one of the following: SEQ ID NO: 19 and 29 or a nucleic acid sequence having at least 80% homology thereof.

In the present application, the low-density lipoprotein receptor-related protein or fragment thereof expressed by the genetically modified immune cell and the chimeric antigen receptor (CAR) can be two independent proteins. That is, the two do not have any interlinking relationship to form any form of di(poly)mer or protein complex. However, the low-density lipoprotein receptor-related protein or fragment thereof expressed by the genetically modified immune cell and the chimeric antigen receptor (CAR) can also be interlinked. For example, in some cases, the two proteins formed by translation are not completely cleaved, so that the low-density lipoprotein receptor-related protein or fragment thereof forms a complex with the chimeric antigen receptor.

Preparation Method

The present application provides a method for preparing a genetically modified immune cell, including a following step: up-regulating the expression of the low density lipoprotein receptor-associated protein or fragment thereof in the genetically modified immune cell.

The present application further provides a method for preparing the composition, including a following step: up-regulating the expression of the low density lipoprotein receptor-associated protein or fragment thereof in the genetically modified immune cell.

In the present application, the method can further comprise a following step of isolating and obtaining peripheral blood mononuclear cells PBMCs, CD3$^+$T lymphocyte, CD8$^+$T lymphocyte, CD4$^+$T lymphocyte or regulatory T cells.

In the present application, the method can comprise a following step: isolating and activating the genetically modified immune cell, wherein the activating comprises application of a T cell medium to the isolated genetically modified immune cell.

In the present application, the T cell medium can be selected from one or more of the following group: DMEM medium, 1640 medium, MEM medium, and X-VIVO medium.

In the present application, the method can further comprise a following step: adding one or more T cell stimulatory factors to the isolated peripheral blood mononuclear cells PBMC.

For example, the T cell stimulatory factors can be selected from the group consisting of B lymphocyte surface antigens antibody, TNF antibody, intracellular polyester, and antibiotics. Alternatively, the T cell stimulatory factors can be selected from the group consisting of CD3 antibody, CD28 antibody, 4-1BB antibody, CD80 antibody, CD86 antibody, PHA, PMA, and ionomycin.

In the present application, the T cell stimulatory factors can comprise CD3 antibody, and the CD3 antibody can be at a concentration of 1-10000 ng/mL. For example, the CD3 antibody can be at a concentration of 1-9000 ng/mL, 1-5000 ng/mL, 1-4000 ng/mL, 1-3000 ng/mL, 1-1000 ng/mL, 1-500 ng/mL, 1-400 ng/mL, 1-300 ng/mL, 1-200 ng/mL, 1-100 ng/mL, 1-50 ng/mL, 1-40 ng/mL, 1-30 ng/mL, 1-20 ng/mL, 1-10 ng/mL or 1-5 ng/mL. In the present application, the T cell stimulatory factors can comprise CD28 antibody, and the CD28 antibody can be at a concentration of 1-10000 ng/mL. For example, the CD28 antibody can be at a concentration of 1-9000 ng/mL, 1-5000 ng/mL, 1-4000 ng/mL, 1-3000 ng/mL, 1-1000 ng/mL, 1-500 ng/mL, 1-400 ng/mL, 1-300 ng/mL, 1-200 ng/mL, 1-100 ng/mL, 1-50 ng/mL, 1-40 ng/mL, 1-30 ng/mL, 1-20 ng/mL, 1-10 ng/mL or 1-5 ng/mL.

In the present application, the method can further comprise adding one or more cytokines into the isolated PBMC. In the present application, the cytokines can comprise interleukins. For example, the interleukins can comprise one or more selected from the group consisting of IL2, IL21, IL7, and IL15.

In the present application, the interleukins can comprise IL2, and the IL2 can be at a concentration of 0.1-10000 U/mL. For example, the IL2 can be at a concentration of 0.1-8000 U/mL, 0.1-6000 U/mL, 0.1-4000 U/mL, 0.1-2000 U/mL, 5-2000 U/mL, 5-1900 U/mL, 5-1800 U/mL, 5-1700 U/mL, 5-1600 U/mL, 5-1500 U/mL, 5-1400 U/mL, 5-1300 U/mL, 5-1200 U/mL, 5-1100 U/mL, 5-1000 U/mL, 5-900 U/mL, 5-800 U/mL, 5-700 U/mL, 5-600 U/mL, 5-500 U/mL, 5-400 U/mL, 5-300 U/mL, 5-200 U/mL, 5-500 U/mL, 5-400 U/mL, 5-300 U/mL, 5-200 U/mL, 5-100 U/mL, 5-50 U/mL, 5-40 U/mL, 5-30 U/mL, 5-20 U/mL or 5-10 U/mL.

In the present application, the interleukins can comprise IL21, and the IL21 can be at a concentration of 0.01-1000 ng/mL. For example, the IL21 can be at a concentration of 0.01-800 ng/mL, 0.01-600 ng/mL, 0.01-400 ng/mL, 0.01-200 ng/mL, 0.01-100 ng/mL, 0.1-100 ng/mL, 0.1-90 ng/mL, 0.1-80 ng/mL, 0.1-70 ng/mL, 0.1-60 ng/mL, 0.1-50 ng/mL, 0.1-40 ng/mL, 0.1-30 ng/mL, 0.1-20 ng/mL, 0.1-10 ng/mL or 0.1-5 ng/mL.

In the present application, the interleukins can comprise IL7, and the IL7 can be at a concentration of 0.01-1000 ng/mL. For example, the IL7 can be at a concentration of 0.01-800 ng/mL, 0.01-600 ng/mL, 0.01-400 ng/mL, 0.01-200 ng/mL, 0.01-100 ng/mL, 0.1-100 ng/mL, 0.1-90 ng/mL, 0.1-80 ng/mL, 0.1-70 ng/mL, 0.1-60 ng/mL, 0.1-50 ng/mL, 0.1-40 ng/mL, 0.1-30 ng/mL, 0.1-20 ng/mL, 0.1-10 ng/mL or 0.1-5 ng/mL.

In the present application, the interleukins can comprise IL15, and the IL15 can be at a concentration of 0.01-1000 ng/mL. For example, the IL15 can be at a concentration of 0.01-800 ng/mL, 0.01-600 ng/mL, 0.01-400 ng/mL, 0.01-200 ng/mL, 0.01-100 ng/mL, 0.1-100 ng/mL, 0.1-90 ng/mL, 0.1-80 ng/mL, 0.1-70 ng/mL, 0.1-60 ng/mL, 0.1-50 ng/mL, 0.1-40 ng/mL, 0.1-30 ng/mL, 0.1-20 ng/mL, 0.1-10 ng/mL or 0.1-5 ng/mL.

Promoting the Proliferation of Immune Cells, Promoting the Production of Memory Immune Cells, Inhibiting the Differentiation of Immune Cells, Enhancing the Release of Cytokines, and Enhancing the Killing Ability to the Tumor In one aspect, the present application provides a method for promoting the proliferation of immune cells, including a following step: upregulating the expression of the low density lipoprotein receptor-associated protein or fragment thereof in the immune cells.

In one aspect, the present application provides a method for promoting the production of memory immune cells, including the step of upregulating the expression of the low density lipoprotein receptor-associated protein or fragment thereof in the immune cells, thereby promoting the differentiation of the immune cells to the memory immune cells.

In one aspect, the present application provides a method for inhibiting the differentiation of immune cells, including the step of upregulating the expression of the low density lipoprotein receptor-associated protein or fragment thereof in the immune cells, thereby inhibiting the differentiation of the immune cells to the differentiated immune cells.

In one aspect, the present application provides a method for enhancing the release of cytokines from immune cells, including a following step: upregulating the expression of the low density lipoprotein receptor-associated protein or fragment thereof in the immune cells.

In the present application, the cytokines can comprise interleukin, interferon and/or tumor necrosis factor. In the present application, the cytokines can comprise IL-2, IL4, IL6, IL7, IL10, IL21, TNF-α and/or IFNγ.

In one aspect, the present application provides a method for enhancing the ability of immune cells to kill tumors, including a following step: upregulating the expression of the low density lipoprotein receptor-associated protein or fragment thereof in the immune cells.

In one aspect, the present application provides a method for preventing the tumor recurrence in a subject, including administering immune cells to a subject susceptible to a tumor, wherein the expression of the low density lipoprotein receptor-associated protein or fragment thereof is upregulated in the immune cells.

In one aspect, the present application provides a method for treating tumors in a subject in need thereof, including the step of administering immune cells to the subject, wherein the expression of the low density lipoprotein receptor-associated protein or fragment thereof is upregulated in the immune cells.

In the present application, the tumor can be selected from the group consisting of liver cancer, lung cancer, leukemia, and mesothelioma. In the present application, the method can comprise an in vivo method, and an in vitro method.

In the present application, the up-regulation of the expression can be that the expression of the low-density lipoprotein receptor-related protein or fragment thereof in the immune cells is significantly up-regulated (e.g., by 5% or more, 10% or more, 20% or more, 30% or more, 40% or more, 50% or more, 60% or more, 70% or more, 80% or more, 90% or more, 100% or more) as compared to the control immune cells, wherein the control immune cells are the corresponding immune cells in which the expression of the low-density lipoprotein receptor-related protein or fragment thereof is not substantially up-regulated.

In the present application, the promoting of the production of memory immune cells can be that the number of the memory immune cells produced by the immune cells is substantially up-regulated (e.g., by 5% or more, 10% or more, 20% or more, 30% or more, 40% or more, 50% or more, 60% or more, 70% or more, 80% or more, 90% or more, 100% or more) as compared to the control immune cells, wherein the control immune cells are the corresponding immune cells in which the expression of the low density lipoprotein receptor-associated protein or fragment thereof is not substantially up-regulated.

In the present application, the inhibiting of the differentiation of immune cells can be that the number of the differentiated immune cells produced by the immune cells are substantially down-regulated (e.g., by 5% or more, 10% or more, 20% or more, 30% or more, 40% or more, 50% or more, 60% or more, 70% or more, 80% or more, 90% or more, 100% or more) as compared to the number of the memory immune cells produced by the control immune cells, wherein the control immune cells are the corresponding immune cells in which the expression of the low density lipoprotein receptor-associated protein or fragment thereof is not substantially up-regulated.

In the present application, the enhancing of the release of cytokines from immune cells can be that the number of the cytokines released by the immune cells are substantially up-regulated (e.g., by 5% or more, 10% or more, 20% or more, 30% or more, 40% or more, 50% or more, 60% or more, 70% or more, 80% or more, 90% or more, 100% or more) as compared to the number of the cytokines released by the control immune cells, wherein the control immune cells are the corresponding immune cells in which the expression of the low density lipoprotein receptor-associated protein or fragment thereof is not substantially up-regulated.

In the present application, the enhancing of the killing ability of the immune cells can be that the ability of the immune cells to kill tumors are substantially increased (e.g., by 5% or more, 10% or more, 20% or more, 30% or more, 40% or more, 50% or more, 60% or more, 70% or more, 80% or more, 90% or more, 100% or more) as compared to the ability of the control immune cells to kill tumors, wherein the control immune cells are the corresponding immune cells in which the expression of the low density lipoprotein receptor-associated protein or fragment thereof is not substantially up-regulated.

In the present application, the prevention of the tumor recurrence in a subject can be that the ability of the immune cells for preventing the tumor recurrence in the subject is substantially increased (e.g., by 5% or more, 10% or more, 20% or more, 30% or more, 40% or more, 50% or more, 60% or more, 70% or more, 80% or more, 90% or more, 100% or more) as compared to the ability of the control immune cells for preventing the tumor recurrence, wherein the control immune cells are the corresponding immune cells in which the expression of the low density lipoprotein receptor-associated protein or fragment thereof is not substantially up-regulated.

In the present application, the treatment of a tumor in a subject in need thereof can be that the therapeutical effect of the immune cells for a tumor is substantially increased (e.g., by 5% or more, 10% or more, 20% or more, 30% or more, 40% or more, 50% or more, 60% or more, 70% or more, 80% or more, 90% or more, 100% or more) as compared to the therapeutical effect of the control immune cells for a tumor, wherein the control immune cells are the corresponding immune cells in which the expression of the low density lipoprotein receptor-associated protein or fragment thereof is not substantially up-regulated.

For example, the corresponding immune cells can comprise lymphocytes. In the present application, the corresponding immune cells can comprise T cells. In the present application, the T cells can comprise memory stem cell-like T cells (TSCM) and/or central memory T cells (TCM). In the present application, the TSCM can be $CCR7^+$ and/or $CD62L^+$. In the present application, the TSCM can further have one or more properties selected from the group consisting of: $CD45RA^+$ or $CD45RA^-$, $CD45RO^+$ or $CD45RO^-$, $CD27^+$, $CD28^+$, $CD127^+$, $CD122^+$, $CD3^+$, $CD4^+$, and $CD8^+$. In the present application, the corresponding immune cells can comprise genetically modified immune cells, and the genetically modified immune cells express chimeric antigen receptor (CAR). In the present application, the corresponding immune cells can comprise genetically modified T cells.

In the present application, the level of the low density lipoprotein receptor-associated protein or fragment thereof in the corresponding immune cells can be only the expression level of the expression of the low density lipoprotein receptor-associated protein or fragments thereof in a normal organism, or a substantially un-upregulated expression level as compared with the level of the low density lipoprotein receptor-associated protein or fragment thereof in a normal organism. For example, the substantially un-upregulated level can refer to an up-regulation of at most 4.5%, at most 4%, at most 3%, at most 2%, at most 1%, at most 0.5%, at most 0.3%, at most 0.1%, at most 0.01% or less. In the present application, the corresponding immune cells can be free of a vector including a nucleoside molecule encoding the low density lipoprotein receptor-associated protein or fragment thereof, and/or the corresponding immune cells can be free of a nucleoside molecule encoding the low density lipoprotein receptor-associated protein or fragment thereof.

In the present application, a method for measuring the expression level of the low density lipoprotein receptor-associated protein or fragments thereof and/or the cytokines can comprise quantitative PCR, western blot, and immuno-histochemistry.

In the present application, a method for measuring the memory immune cells and/or the differentiated immune cells can comprise flow cytometry cells, immunofluorescence, magnetic bead separation, ELISA, ELISPOT, and quantitative PCR.

In the present application, the evaluation of the therapeutic effect of tumors can utilize an index selected from the group consisting of tumor volume, overall survival (OS), overall remission (DOR), duration of stable disease, disease-free survival (DFS), progression-free survival (PFS), disease control rate (DCR), objective response rate (ORR)) and/or clinical benefit response ratio.

In the present application, the evaluation of the effect of preventing the tumor recurrence in a subject can utilize an index selected from the group consisting of the express level of tumor markers (e.g., tumor-related antigens, tumor-specific genes, and tumor suppressor genes), histological test results (e.g., epithelial hyperplasia, degree of polyp disappearance), imaging test results (e.g., molybdenum target test result) and/or express level of serum markers (e.g., serum free DNA, methylated DNA).

Composition and Use Thereof

The present application provides a composition including the genetically modified immune cell.

In the present application, the composition can further optionally comprise a pharmaceutically acceptable carrier. The pharmaceutically acceptable carrier can comprise buffers, antioxidants, preservatives, low molecular weight peptides, proteins, hydrophilic polymers, amino acids, sugars, chelating agents, counter ions, metal complexes and/or non-ionic surfactants, etc.

In the present application, the composition can be formulated for oral administration, intravenous administration, intramuscular administration, in situ administration at the tumor site, inhalation, rectal administration, vaginal administration, transdermal administration or administration by subcutaneous depot.

The composition can be used to inhibit tumor growth. For example, the composition of the present application can inhibit or delay the development or progression of the disease, reduce the size of the tumor (or even substantially eliminate the tumor), and/or alleviate and/or stabilize the disease state.

The composition of the present application can comprise a therapeutically effective amount of the antibody or the fragment for antigen-binding thereof. The therapeutically effective amount is a dose required to prevent and/or treat (at least partly treating) a disease or disorder (e.g., cancer) and/or any complications thereof in a subject having or at a risk of developing the disease or disorder.

The present application provides use of the genetically modified cells and/or the composition in manufacture of a drug for treating and/or preventing tumor.

In the present application, the tumor can be selected from the group consisting of liver cancer, lung cancer, leukemia, and mesothelioma.

Without being limited by any theory, the following embodiments are only to illustrate the working methods of the device, method, and system of the present application, and are not used to limit the scope of the present application invention.

EXAMPLES

Example 1

Construction of Lentiviral Vector

CAR-T takes targeting GPC3, CD19, Mesothelin (MSLN), HER2, BCMA as examples, fragments of the CAR structures are artificially synthesized and constructed into a lentiviral vector (LV100A, System Biosciences), followed by transfection in line with the instructions to obtain lentiviruses (as shown in FIG. 1), that is, GPC3-41BB, GPC3-41BB-L6, GPC3-41BB-TL6, GPC3-CD28, GPC3-CD28-L6, GPC3-CD28-TL6, GPC3-41BB-L5, GPC3-41BB-TL5, BCMA-41BB, BCMA-41BB-L6, BCMA-41BB-TL6, CD19-41BB, CD19-41BB-L6, CD19-41BB-TL6, MSLN-41BB, MSLN-41BB-L6, MSLN-41BB-TL6, HER2-41BB, HER2-41BB-L6, and HER2-41BB-TL6 lentiviruses, respectively.

GPC3-41BB is constructed by successively splicing a leader sequence, GPC3 ScFv, a CD8 hinge region, and a transmembrane region, 41BB, CD3zeta from 5'end to 3'end, of which the nucleotide sequences are as set forth in SEQ ID NO.30, SEQ ID NO.1, SEQ ID NO.11, SEQ ID NO.15, and SEQ ID NO.17.

GPC3-41BB-L6 is constructed by successively splicing a leader sequence, GPC3 ScFv, a CD8 hinge region, and a transmembrane region, 41BB, CD3zeta, 2A, L6 from Send to 3'end, of which the nucleotide sequences are as set forth in SEQ ID NO.30, SEQ ID NO.1, SEQ ID NO.11, SEQ ID NO.15, SEQ ID NO.17, SEQ ID NO.19, and SEQ ID NO.21.

GPC3-41BB-TL6 is constructed by successively splicing a leader sequence, GPC3 ScFv, a CD8 hinge region, and a transmembrane region, 41BB, CD3zeta, 2A, TL6 from 5'end to 3'end, of which the nucleotide sequences are as set forth in SEQ ID NO.30, SEQ ID NO.1, SEQ ID NO.11, SEQ ID NO.15, SEQ ID NO.17, SEQ ID NO.19, and SEQ ID NO.23.

GPC3-41BB-L5 is constructed by successively splicing a leader sequence, GPC3 ScFv, a CD8 hinge region, and a transmembrane region, 41BB, CD3zeta, 2A, L5 from 5'end to 3'end, of which the nucleotide sequences are as set forth in SEQ ID NO.30, SEQ ID NO.1, SEQ ID NO.11, SEQ ID NO.15, SEQ ID NO.17, SEQ ID NO.19, and SEQ ID NO.25.

GPC3-41BB-TL5 is constructed by successively splicing a leader sequence, GPC3 ScFv, a CD8 hinge region, and a transmembrane region, 41BB, CD3zeta, 2A, TL5 from 5'end to 3'end, of which the nucleotide sequences are as set forth in SEQ ID NO.30, SEQ ID NO.1, SEQ ID NO.11, SEQ ID NO.15, SEQ ID NO.17, SEQ ID NO.19, and SEQ ID NO.27.

GPC3-CD28 is constructed by successively splicing a leader sequence, GPC3 ScFv, a CD8 hinge region, and a transmembrane region, CD28, CD3zeta from 5'end to 3'end, of which the nucleotide sequences are as set forth in SEQ ID NO.30, SEQ ID NO.1, SEQ ID NO.11, SEQ ID NO.13, and SEQ ID NO.17.

GPC3-CD28-L6 is constructed by successively splicing a leader sequence, GPC3 ScFv, a CD8 hinge region, and a transmembrane region, CD28, CD3zeta, 2A, L6 from 5'end to 3'end, of which the nucleotide sequences are as set forth in SEQ ID NO.30, SEQ ID NO.1, SEQ ID NO.11, SEQ ID NO.13, SEQ ID NO.17, SEQ ID NO.19, and SEQ ID NO.21.

GPC3-CD28-TL6 is constructed by successively splicing a leader sequence, GPC3 ScFv, a CD8 hinge region, and a transmembrane region, CD28, CD3zeta, 2A, TL6 from 5'end to 3'end, of which the nucleotide sequences are as set forth in SEQ ID NO.30, SEQ ID NO.1, SEQ ID NO.11, SEQ ID NO.13, SEQ ID NO.17, SEQ ID NO.19, and SEQ ID NO.23.

BCMA-41BB is constructed by successively splicing a leader sequence, BCMAScFv, a CD8 hinge region, and a transmembrane region, 41BB, CD3zeta from 5'end to 3'end, of which the nucleotide sequences are as set forth in SEQ ID NO.30, SEQ ID NO.5, SEQ ID NO.11, SEQ ID NO.15, and SEQ ID NO.17.

BCMA-41BB-L6 is constructed by successively splicing a leader sequence, BCMAScFv, a CD8 hinge region, and a transmembrane region, 41BB, CD3zeta, 2A, L6 from 5'end to 3'end, of which the nucleotide sequences are as set forth in SEQ ID NO.30, SEQ ID NO.5, SEQ ID NO.11, SEQ ID NO.15, SEQ ID NO.17, SEQ ID NO.19, and SEQ ID NO.21.

BCMA-41BB-TL6 is constructed by successively splicing a leader sequence, BCMAScFv, a CD8 hinge region, and a transmembrane region, 41BB, CD3zeta, 2A, TL6 from 5'end to 3'end, of which the nucleotide sequences are as set forth in SEQ ID NO.30, SEQ ID NO.5, SEQ ID NO.11, SEQ ID NO.15, SEQ ID NO.17, SEQ ID NO.19, and SEQ ID NO.23.

CD19-41BB is constructed by successively splicing a leader sequence, CD19ScFv, a CD8 hinge region, and a transmembrane region, 41BB, CD3zeta from 5'end to 3'end, of which the nucleotide sequences are as set forth in SEQ ID NO.30, SEQ ID NO.3, SEQ ID NO.11, SEQ ID NO.15, and SEQ ID NO.17.

CD19-41BB-L6 is constructed by successively splicing a leader sequence, CD19ScFv, a CD8 hinge region, and a transmembrane region, 41BB, CD3zeta, 2A, L6 from 5'end to 3'end, of which the nucleotide sequences are as set forth in SEQ ID NO.30, SEQ ID NO.3, SEQ ID NO.11, SEQ ID NO.15, SEQ ID NO.17, SEQ ID NO.19, and SEQ ID NO.21.

CD19-41BB-TL6 is constructed by successively splicing a leader sequence, CD19ScFv, a CD8 hinge region, and a transmembrane region, 41BB, CD3zeta, 2A, TL6 from 5'end to 3'end, of which the nucleotide sequences are as set forth in SEQ ID NO.30, SEQ ID NO.3, SEQ ID NO. 11, SEQ ID NO.15, SEQ ID NO.17, SEQ ID NO.19, and SEQ ID NO.23.

MSLN-41BB is constructed by successively splicing a leader sequence, MSLNScFv, a CD8 hinge region, and a transmembrane region, 41BB, CD3zeta from 5'end to 3'end, of which the nucleotide sequences are as set forth in SEQ ID NO.30, SEQ ID NO.7, SEQ ID NO.11, SEQ ID NO.15, and SEQ ID NO.17.

MSLN-41BB-L6 is constructed by successively splicing a leader sequence, MSLNScFv, a CD8 hinge region, and a transmembrane region, 41BB, CD3zeta, 2A, L6 from 5'end to 3'end, of which the nucleotide sequences are as set forth in SEQ ID NO.30, SEQ ID NO.7, SEQ ID NO.11, SEQ ID NO.15, SEQ ID NO.17, SEQ ID NO.19, and SEQ ID NO.21.

MSLN-41BB-TL6 is constructed by successively splicing a leader sequence, MSLNScFv, a CD8 hinge region, and a transmembrane region, 41BB, CD3zeta, 2A, TL6 from 5'end to 3'end, of which the nucleotide sequences are as set forth in SEQ ID NO.30, SEQ ID NO.7, SEQ ID NO.11, SEQ ID NO.15, SEQ ID NO.17, SEQ ID NO.19, and SEQ ID NO.23.

HER2-41BB is constructed by successively splicing a leader sequence, HER2ScFv, a CD8 hinge region, and a transmembrane region, 41BB, CD3zeta from 5'end to 3'end, of which the nucleotide sequences are as set forth in SEQ ID NO.30, SEQ ID NO.9, SEQ ID NO.11, SEQ ID NO.15, and SEQ ID NO.17.

HER2-41BB-L6 is constructed by successively splicing a leader sequence, HER2ScFv, a CD8 hinge region, and a transmembrane region, 41BB, CD3zeta, 2A, L6 from 5'end to 3'end, of which the nucleotide sequences are as set forth in SEQ ID NO.30, SEQ ID NO.9, SEQ ID NO.11, SEQ ID NO.15, SEQ ID NO.17, SEQ ID NO.19, and SEQ ID NO.21.

HER2-41BB-TL6 is constructed by successively splicing a leader sequence, HER2 ScFv, a CD8 hinge region, and a transmembrane region, 41BB, CD3zeta, 2A, TL6 from 5'end to 3'end, of which the nucleotide sequences are as set forth in SEQ ID NO.30, SEQ ID NO.9, SEQ ID NO.11, SEQ ID NO.15, SEQ ID NO.17, SEQ ID NO.19, and SEQ ID NO.23.

Example 2

Infection of T Cells by Lentivirus

Fresh human peripheral blood was separated by ficoll separation solution to obtain more than $1\times10^7$ peripheral blood mononuclear lymphocytes (PBMC). The anti-human CD3 and anti-human CD28 antibodies were diluted with PBS to a final concentration of 1 µg/ml. Then, the diluted antibody mixture was added into the cell culture dish, spread evenly on the cell culture dish, and incubated at room temperature for 2 hours. After 2 hours, the antibody mixture was washed once with PBS. Subsequently, the separated PBMCs were re-suspended in a lymphocyte culture medium containing Xvivo15 medium, 5% FBS, 200 U/ml 1L2T or Xvivo15 medium, 5% FBS, 20 ng/ml IL21, 10 ng/ml IL7 to a final concentration of $1\times10^6$ cells/ml, and then added into a culture dish containing the antibody mixture and cultured at 37° C. and 5% $CO_2$ for 24 hours to activate T cells.

An amount of T cell culture solution was added synperonic F108 with a final concentration of 1 mg/ml. The mixture was mixed homogeneously, and heated to 37° C. in a water bath to prepare an uninfected reagent. Subsequently, cell culture dishes were prepared for experiments. First, 1 mg/ml anti-human CD3 antibody and 0.5 mg/ml anti-human CD28 antibody were diluted with a PBS buffer at a volume ratio of 1:1000 and mixed homogeneously, and then diluted with retronectin (1 mg/ml) reagent at a volume ratio of 1:40 and mixed homogeneously. The mixture was spread evenly in a cell culture dish and incubated at room temperature for 2 hours. After 2 hours, the mixture was washed with PBS, and the cell culture dish was done.

The activated T cells were diluted with the infection reagent, and the mixture was added into each lentivirus prepared in Example 1 at the ratio of MOI=3 and mixed homogeneously. Then, the mixture was spread evenly in the cell culture dish for lentivirus infection, so as to obtain the T cells expressing GPC3-41BB, GPC3-41BB-L6, GPC3-41BB-TL6, GPC3-CD28, GPC3-CD28-L6, GPC3-CD28-TL6, GPC3-41BB-L5, GPC3-41BB-TL5, BCMA-41BB, BCMA-41BB-L6, BCMA-41BB-TL6, CD19-41BB, CD19-41BB-L6, CD19-41BB-TL6, MSLN-41BB, MSLN-41BB-L6, MSLN-41BB-TL6, HER2-41BB, HER2-41BB-L6 and HER2-41BB-TL6, respectively. After infection, the infected cells were monitored for their densities which were maintained at $1\times10^6$ cells/ml. After 14 days, the number of cells could be expanded by 10-100 times.

Example 3

LRP6, LRP6 Truncated Protein, LRP5 or LRP5 Truncated Protein Promotes the Formation of Memory T Cells The GPC3-41BB, GPC3-41BB-L6, GPC3-41BB-TL6, GPC3-CD28, GPC3-CD28-L6, GPC3-CD28-TL6, GPC3-41BB-L5, GPC3-41BB-TL5, BCMA-41BB, BCMA-41BB-L6, BCMA-41BB-TL6, CD19-41BB, CD19-41BB-L6, CD19-41BB-TL6, MSLN-41BB, MSLN-41BB-L6, MSLN-41BB-TL6, HER2-41BB, HER2-41BB-L6 and HER2-41BB-TL6 T cells obtained in Example 2 were cultured in vitro in a cell incubator at 37° C. and 5% $CO_2$ for 9 days or 13 days in total.

The expression of CD3, CD8, CD45RO, CD45RA, CD62L, CCR7, CD95, CD122, CD127, CD27, CD28 proteins in T cells were detected by BD flow cytometry. Of those, the results of the measured protein expression are shown in FIG. 2.

The results show that in the T cells expressing GPC3-41BB-L6 or GPC3-41BB-TL6, the proportion of the memory stem cell-like T cells (TSCM) and the central memory T cells (TCM) in the total cells is substantially higher than those in the control group; in the T cells expressing GPC3-CD28-L6 or GPC3-CD28-TL6, the percent of TSCMs and TCMs in the total cells is substantially higher than those in the control group; in the T cells expressing GPC3-41BB-L5 or GPC3-41BB-TL5, the percent of TSCMs and TCMs in the total cells is substantially higher than those in the control group; in the T cells expressing BCMA-41BB-L6 or BCMA-41BB-TL6, the percent of TSCMs and TCMs in the total cells is substantially higher than those in the control group; in the T cells expressing CD19-41BB-L6 or CD19-41BB-TL6, the percent of TSCMs and TCMs in the total cells is substantially higher than those in the control group; in the T cells expressing MSLN-41BB-L6 or MSLN-41BB-TL6, the percent of TSCMs and TCMs in the total cells is substantially higher than those in the control group; and in the T cells expressing HER2-41BB-L6 or HER2-41BB-TL6, the percent of TSCMs and TCMs in the total cells is also substantially higher than those in the control group.

Example 4

LRP6 or Its Truncated Protein Inhibits the Differentiation of Treg Cells

Figure 3:
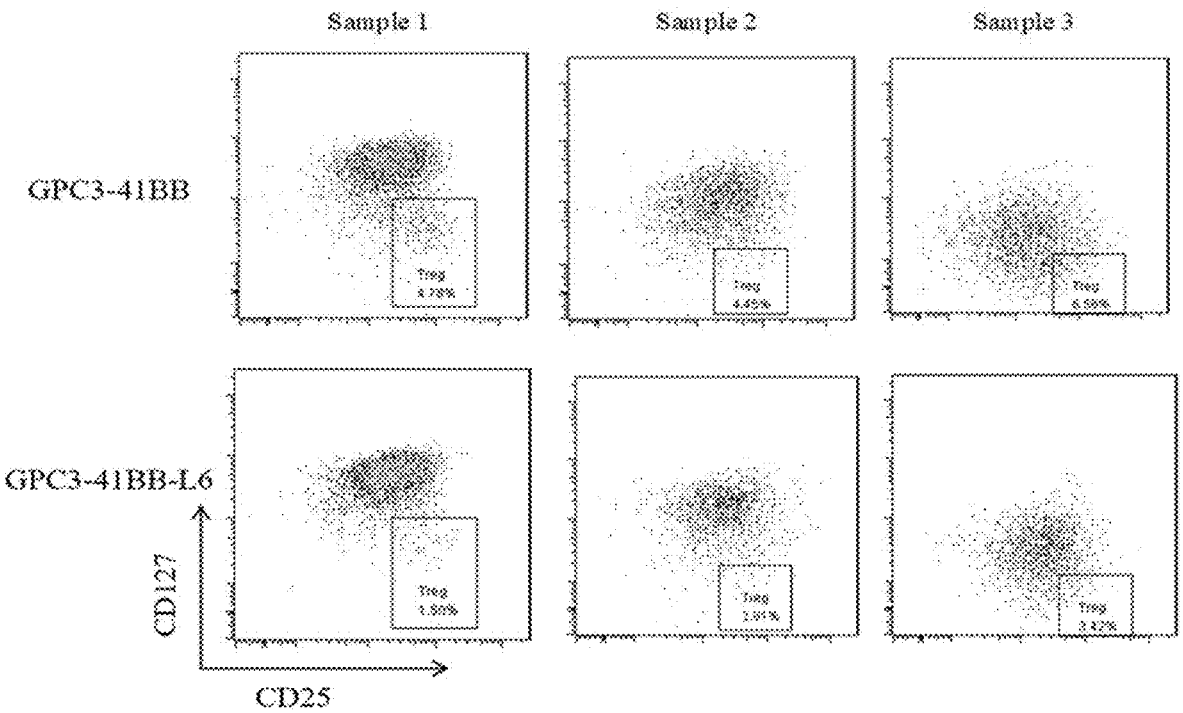
FIG. 3 shows a result of the genetically modified immune cell according to the present application for inhibiting the differentiation of immune cells.

The T cells expressing GPC3-41BB and GPC3-41BB-L6, respectively, as obtained in Example 2 were in vitro cultured in a cell incubator at 37° C., 5% $CO_2$ for 9 days or 12 days in total. The expression of the CD3, CD4, CD25, CD127, FoxP3 proteins in the T cells were detected by BD flow cytometry, and the measured results of the protein expression are shown in FIG. 3. The results show that in the T cells expressing GPC3-41BB-L6, the percent of the regulatory T cells (Treg) in the $CD4^+T$ cells is significantly lower than that in the control group expressing GPC3-41BB.

Example 5

Figure 4:
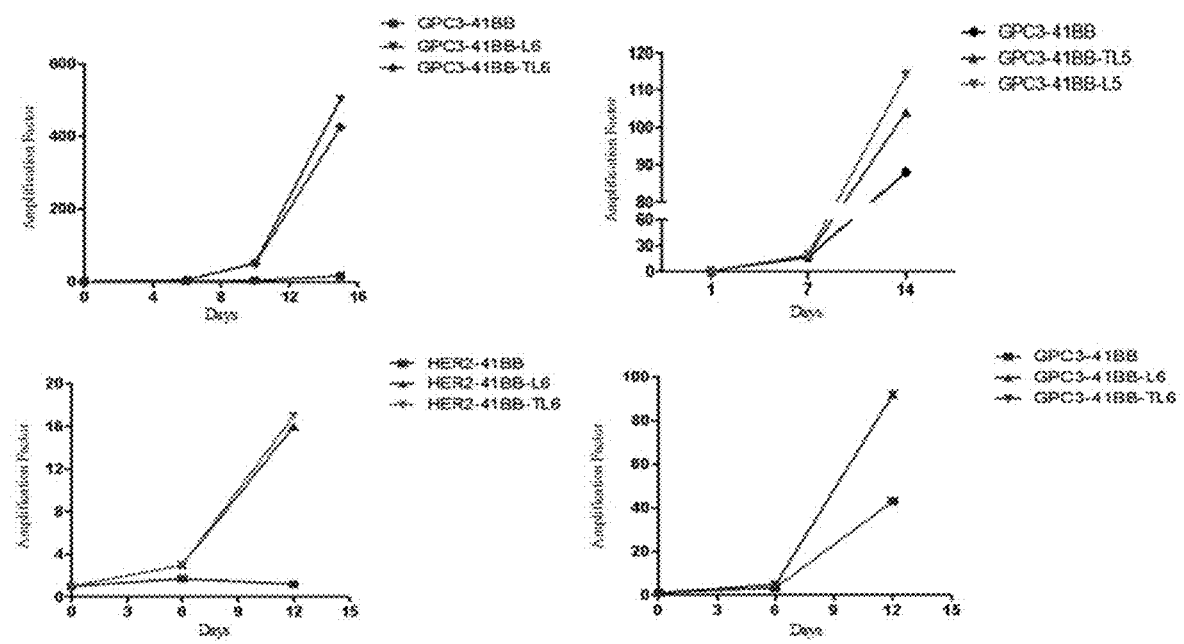
FIG. 4 shows a result of the low density lipoprotein receptor-associated protein or fragment thereof in the immune cells of the present application for promoting the proliferation of the immune cells of the present application.

LRP6, LRP6 Truncated Protein, LRP5 or LRP5 Truncated Protein Promotes the Amplification of Specific CAR-T Cells Induced by Tumor Antigen The T cells expressing GPC3-41BB, GPC3-41BB-L6 or GPC3-41BB-TL6 obtained in Example 2 and the radiated Huh7 or HepG2 cells (purchased from the cells library of the Chinese Academy of Sciences) were co-cultured at a ratio of 1:1 in an Xvivo15 medium, supplemented with the radiated Huh7 or HepG2 cells every 5 days for stimulation (3 times in total), and counted with trypan blue every time. The T cells expressing GPC3-41BB, GPC3-41BB-L5 or GPC3-41BB-TL5 and the radiated Huh7 or HepG2 cells (purchased from the cell library of the Chinese Academy of Sciences) were co-cultured with an Xvivo15 medium at a ratio of 1:1, supplemented with the radiated Huh7 or HepG2 cells every 5 days for stimulation (3 times in total), and counted with trypan blue every time. The T cells expressing HER2-41BB, HER2-41BB-L6 or HER2-41BB-TL6 and the radiated SKOV3 cells (purchased from the cells library of the Chinese Academy of Sciences) at a ratio of 1:1 were co-cultured with an Xvivo15 medium, and supplemented with the radiated SKOV3 every 5 days for stimulation (3 times in total), and counted with trypan blue every time. The cell proliferation in each group was shown in FIG. 4. The results show that the amplification factor of the T cells expressing GPC3-41BB-L6 or GPC3-41BB-TL6 T cells is much higher than that in the control group (T cells expressing GPC3-41BB); the amplification factor of the T cells expressing GPC3-41BB-L5 or GPC3-41BB-TL5 is much higher than that of the control group, and the amplification factor of the T cells expressing HER2-41BB-L6 or HER2-41BB-TL6 is also much higher than that of the control group (T cells expressing HER2-41BB).

Example 6

Figure 5:
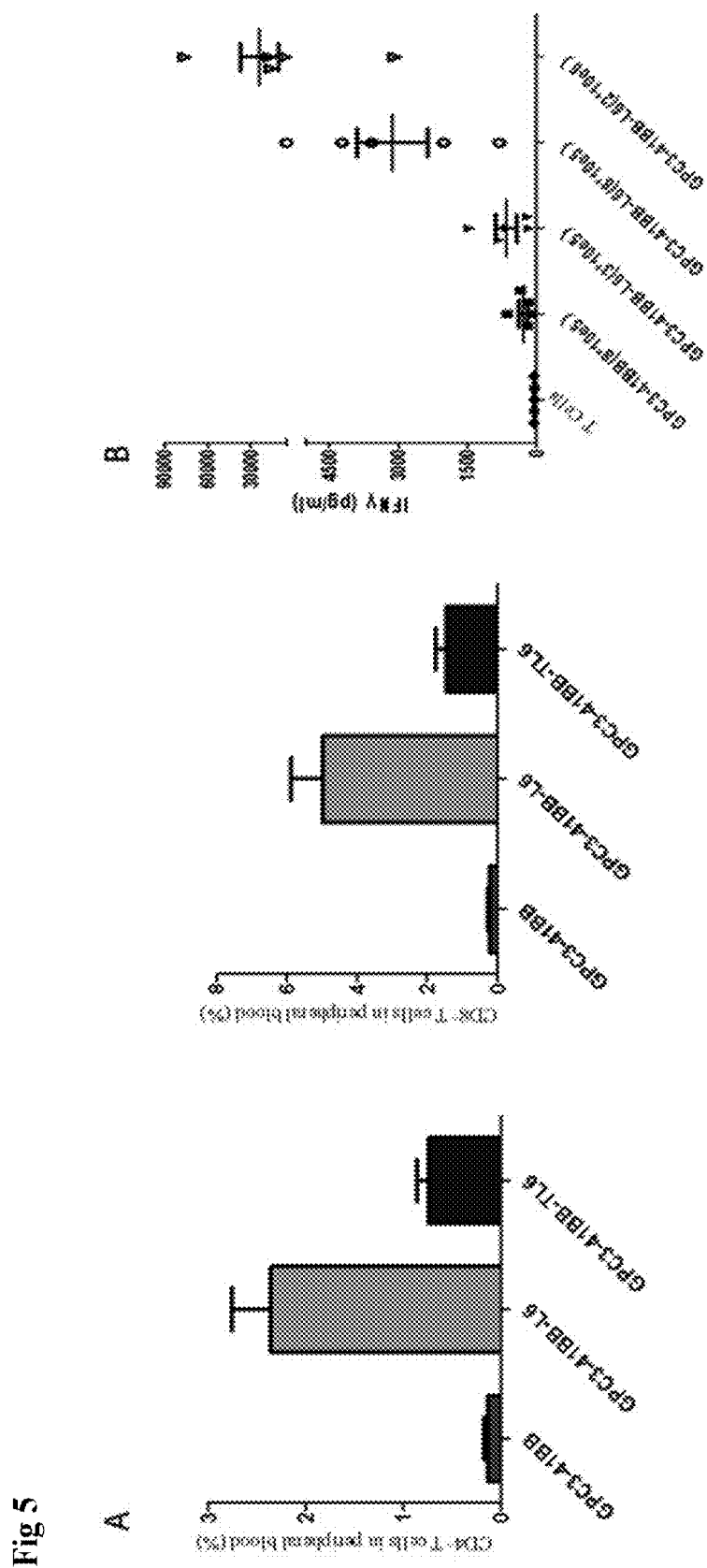
FIGS. 5A-5B show a result of the genetically modified immune cell according to the present application for enhancing the releasing of cytokines.

LRP6 or Its Truncated Protein Promotes the In Vivo Proliferation of CAR-T Cells and the Release of Cytokines Huh7 cells ($1\times10^7$ cells/mouse) were subcutaneously inoculated into NSG mice (purchased from Biocyto). After 14 days, the tumor volume of the mice was about 100 mm$^3$. At that time, the mice were divided into 4 groups, i.e., Group T cell, Group GPC3-41BB, Group GPC3-41BB-L6, and Group GPC3-41BB-TL6, and each group contained 6 mice. Then, they were injected through the tail vein with the cells (namely, each group was injected with unmodified T cells, T cells expressing GPC3-41BB, T cells expressing GPC3-41BB-L6, and T cells expressing GPC3-41BB-TL6 at a dose of $3\times10^6$ cells/mouse). On Day 8, a blood sample (50 μl) was taken from the tail of mice. The expression of human CD8 and CD4 proteins was detected by BD flow cytometry in each group. The results are shown in FIG. 5A. The results in FIG. 5A show that the proportion of the cells expressing CD8 and CD4 proteins in the total cells in Group GPC3-41BB-L6 or Group GPC3-41BB-TL6 is much higher than those in other control groups.

Huh7 cells ($1\times10^7$ cells/mouse) were subcutaneously inoculated into NSG mice (purchased from Biocyto). After 14 days, the tumor volume of the mice was about 100 mm$^3$. At that time, the mice were divided into 5 groups, that is, Group T cell, Group GPC3-41BB, and Group GPC3-41BB-L6, and each group contained 6 mice. Then, the mice were injected via the tail vein with T cells for Group T cell (namely, unmodified T cells at a dose of $2\times10^6$ cells/mouse), T cells expressing GPC3-41BB for Group GPC3-41BB (at a dose of $8\times10^5$ cells/mouse), and T cells expressing GPC3-41BB-L6 for Group GPC3-41BB-L6 (at a dose of $3\times10^5$ cells/mouse, $8\times10^5$ cells/mouse or $2\times10^6$ cells/mouse). On Day 8, a blood sample (50 μl) was taken from the tail of mice. The expression of human IL-2, IL4, IL6, IL10, TNF-α, and IFNγ cytokines was detected by BD flow cytometry in each group. The results in FIG. 5B show that the expression of IFNγ cytokines in Group GPC3-41BB-L6 is substantially higher than those in other control groups.

Example 7

LRP6 or Its Truncated Protein Enhances the Anti-Cancer Effect of CAR-T Cells

Huh7 cells ($1\times10^7$ cells/mouse) were subcutaneously inoculated into NSG mice (purchased from Biocyto). After 14 days, the tumor volume of the mice was about 100 mm$^3$. At that time, the mice were divided into 4 groups, that is, Group T cell, Group GPC3-41BB, and Group GPC3-41BB-L6, respectively, and each group contained 8 mice. Then, the mice were injected via the tail vein with T cells for Group T cells (i.e., unmodified T cells at a dose of $8\times10^5$ cells/mouse), T cells expressing GPC3-41BB for Group GPC3-41BB (at a dose of $8\times10^5$ cells/mouse), and T cells expressing GPC3-41BB-L6 for Group GPC3-41BB-L6 (at a dose of $3\times10^5$ cells/mouse or $8\times10^5$ cells/mouse).

Figure 6:
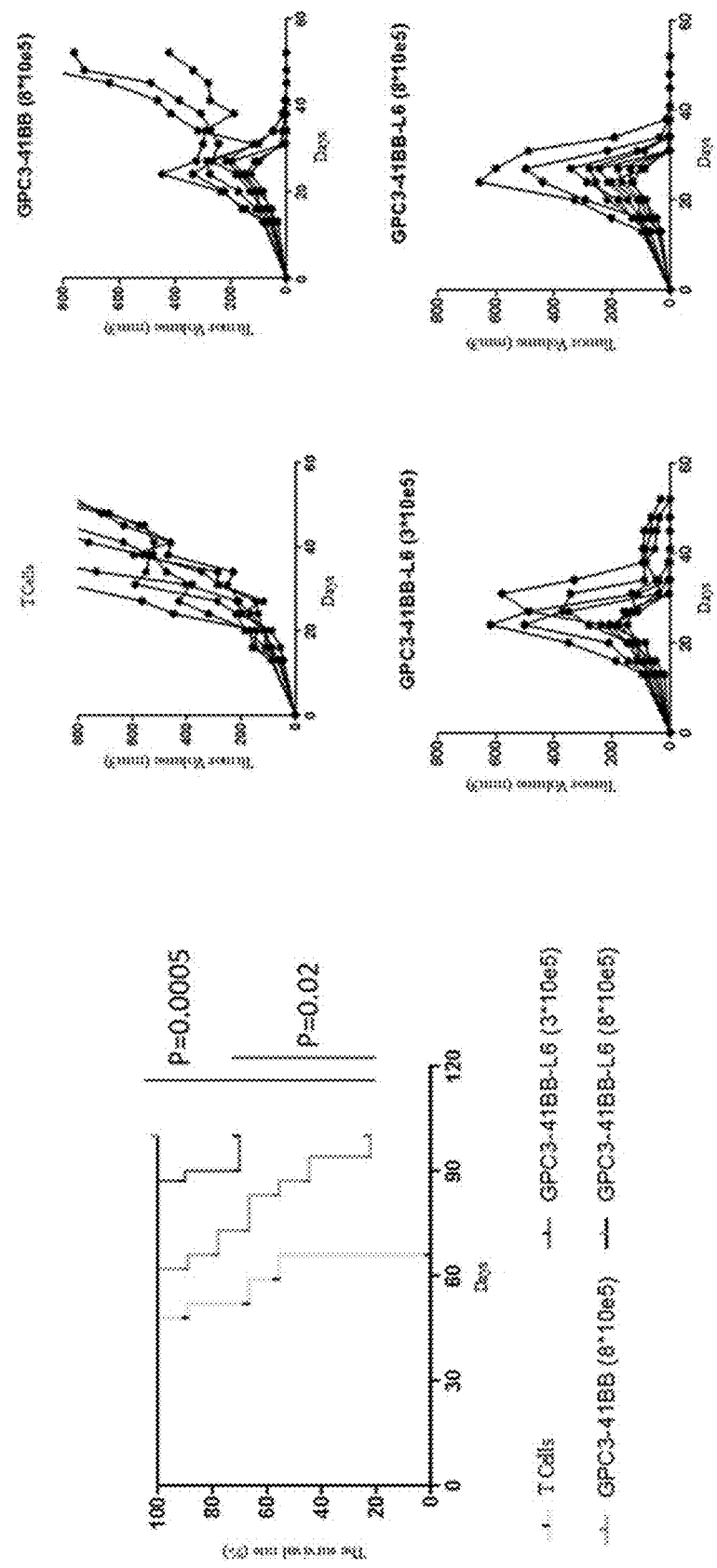
FIG. 6 shows an anti-tumor effect of the genetically modified immune cell according to the present application.

The tumor volume was measured on Monday and Thursday of each week, and the death of the mice was recorded. The results are shown in FIG. 6, and the results show that the tumor-suppressing effect and the survival rate of mice in Group GPC3-41BB-L6 are both significantly higher than those in other control groups, i.e., it is about 3 times that of the control group, Group GPC3-41BB.

Example 8

LRP6 or Its Truncated Protein Promotes the In Vivo Long-Term Survival of CAR-T Cells and Prevents the Recurrence of Tumor Huh7 cells ($1\times10^7$ cells/mouse) were subcutaneously inoculated into NSG mice (purchased from Biocyto). After 14 days, the tumor volume of the mice was about 100 mm$^3$. At that time, the mice were divided into 3 groups, that is, Group T cell, Group GPC3-41BB, and Group GPC3-41BB-L6, and each group contained 9 mice. Then, the mice were injected via the tail vein with T cells for Group T cells (at a dose of $2\times10^6$ cells/mouse), T cells expressing GPC3-41BB for Group GPC3-41BB (at a dose of $2\times10^6$ cells/mouse), and T cells expressing GPC3-41BB-L6 for Group GPC3-41BB-L6 (at a dose of $2\times10^6$ cells/mouse).

After the tumor disappeared for 85 days, the NSG mice were subcutaneously re-inoculated with Huh7 cells (at a dose of $3\times10^7$ cells/mouse). On Day 99, 50 μl of blood was sampled from the tail of the mouse, and detected the expression of human CD8, CD4, and CD3 proteins by BD flow cytometry in each group. On Day 120, the mouse bone marrow was sampled, and detected for the expression of human CD8, CD4, and CD3 proteins by BD flow cytometry in each group.

Figure 7:
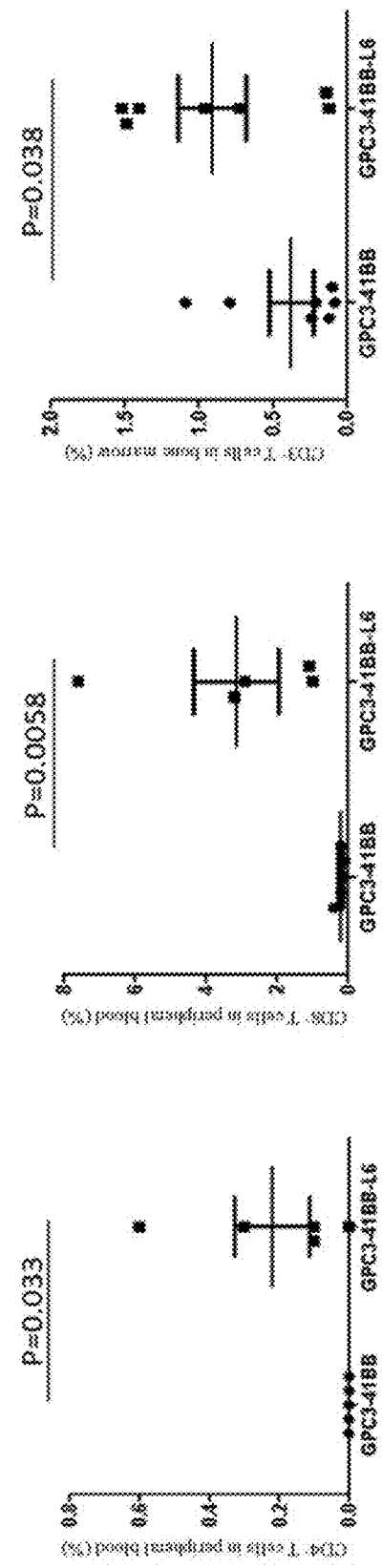
FIG. 7 shows an effect of the genetically modified immune cell according to the present application for preventing the recurrence of a tumor.

The results are shown in FIG. 7. The results show that the proportion of cells expressing CD8 or CD4 protein in the total cells in the peripheral blood and the proportion of cells expressing CD3 proteins in the total cells in the bone marrow of Group GPC3-41BB-L6 are both much higher GPC3-41BB Group, and the mice in Group GPC3-41BB-L6 cannot form any tumor even if they are inoculated again with tumor cells. It shows that LRP6 or its truncated protein promotes the long-term survival of CAR-T cells in the body and has the characteristics of preventing tumor recurrence.

The foregoing detailed description is provided by way of explanation and examples, and is not intended to limit the scope of the appended claims. At present, the various changes of the implementation methods listed in this article are readily apparent to those of ordinary skill in the art, and are encompassed within the scope of the accompanying claims and their equivalences.

We claim:

1. A genetically modified human immune cell, wherein the genetic modification up-regulates an expression of a low density lipoprotein receptor-associated protein or fragment thereof in the genetically modified immune cell, wherein the low density lipoprotein receptor-associated protein is low density lipoprotein receptor-associated protein 6 or the low density lipoprotein receptor-associated protein 5, wherein the low density lipoprotein receptor-associated protein or fragment thereof comprises an intracellular region of the low density lipoprotein receptor-associated protein, wherein the low density lipoprotein receptor-associated protein or fragment thereof comprises an amino acid sequence as set forth in any one of SEQ ID NO: 22, 24, 26, and 28, or an amino acid sequence having at least 80% homology thereof.

2. The genetically modified immune cell according to claim 1, which expresses a chimeric antigen receptor (CAR) or a T cell receptor (TCR).

3. The genetically modified immune cell according to claim 1, wherein the low density lipoprotein receptor-associated protein or fragment thereof is derived from a human.

4. The genetically modified immune cell according to claim 1, wherein the low density lipoprotein receptor-associated protein 6 or fragment thereof further comprises an transmembrane region of the low density lipoprotein receptor-associated protein 6.

5. The genetically modified immune cell according to claim 1, wherein the low density lipoprotein receptor-associated protein 5 or fragment thereof further comprises an transmembrane region of the low density lipoprotein receptor-associated protein 5.

6. A genetically modified human immune cell, wherein the genetic modification up-regulates an expression of a low density lipoprotein receptor-associated protein or fragment thereof in the genetically modified immune cell, wherein the low density lipoprotein receptor-associated protein is low density lipoprotein receptor-associated protein 6 or the low density lipoprotein receptor-associated protein 5, wherein the low density lipoprotein receptor-associated protein or fragment thereof comprises an intracellular region of the low density lipoprotein receptor-associated protein, wherein a nucleic acid molecule encoding the low density lipoprotein receptor-associated protein or fragment thereof comprises a nucleic acid sequence as set forth in any one of SEQ ID NO: 21, 23, 25, and 27.

7. A method for preparing the genetically modified immune cell of claim 1, comprising: up-regulating an expression of the low density lipoprotein receptor-associated protein or fragment thereof in the genetically modified immune cell.

8. The method according to claim 7, further comprising: introducing into the genetically modified immune cell a vector up-regulating the expression of the low density lipoprotein receptor-associated protein or fragment thereof.

9. The method according to claim 8, wherein the vector is at least one selected from the group consisting of a retroviral vector, a lentiviral vector, and a transposon plasmid.

* * * * *

SEQUENCE LISTING

<160> NUMBER OF SEQ ID NOS: 74

<210> SEQ ID NO 1
<211> LENGTH: 789
<212> TYPE: DNA
<213> ORGANISM: Artificial Sequence
<220> FEATURE:
<223> OTHER INFORMATION: GPC3 scFv nucleotide

<400> SEQUENCE: 1

```
atggctctgc ctgtgaccgc tctgctgctg cctctggctc tgctgctgca cgccgcaaga      60
cctgatgtcg tgatgaccca gtccccactg tccctgccag tgacaccagg agagcctgca     120
tccatctctt gccggagctc ccagtctctg gtgcacagca acggcaatac ctacctgcac     180
tggtatctgc agaagccagg ccagagcccc cagctgctga tctacaaggt gtccaaccgg     240
ttctctggag tgccagaccg gttcagcggc tccggctctg gcaccgattt cacactgaag     300
atcagcaggg tggaggcaga ggacgtgggc gtgtactatt gctcccagaa tacccacgtg     360
cccctacat ttggccaggg caccaagctg gagatcaagg gaggaggagg cagcggcgga      420
ggaggctccg gcggcggcgg ctctcaggtg cagctggtgc agtccggagc agaggtgaag     480
aagcctggag ccagcgtgaa ggtgtcctgt aaggcctctg gctacacctt cacagattat     540
gagatgcact gggtgcggca ggcacctgga cagggactgg agtggatggg cgccctggac     600
ccaaagaccg gcgatacagc ctactctcag aagtttaagg gcagggtgac cctgacagcc     660
gacgagagca cctccacagc ctatatggag ctgtctagcc tgcgcagcga ggataccgcc     720
gtgtactatt gcacccgctt ctacagttac acttattggg ggcagggcac tctggtcaca     780
gtctcttca                                                             789
```

<210> SEQ ID NO 2
<211> LENGTH: 263
<212> TYPE: PRT
<213> ORGANISM: Artificial Sequence
<220> FEATURE:
<223> OTHER INFORMATION: GPC3 scFv

<400> SEQUENCE: 2

Met Ala Leu Pro Val Thr Ala Leu Leu Leu Pro Leu Ala Leu Leu Leu
1               5                   10                  15

His Ala Ala Arg Pro Asp Val Val Met Thr Gln Ser Pro Leu Ser Leu
            20                  25                  30

Pro Val Thr Pro Gly Glu Pro Ala Ser Ile Ser Cys Arg Ser Ser Gln
        35                  40                  45

Ser Leu Val His Ser Asn Gly Asn Thr Tyr Leu His Trp Tyr Leu Gln
    50                  55                  60

Lys Pro Gly Gln Ser Pro Gln Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Ser Gln Asn Thr His Val Pro Pro Thr Phe Gly Gln Gly Thr
        115                 120                 125

Lys Leu Glu Ile Lys Gly Gly Gly Gly Ser Gly Gly Gly Gly Ser Gly
    130                 135                 140

Gly Gly Gly Ser Gln Val Gln Leu Val Gln Ser Gly Ala Glu Val Lys
145                 150                 155                 160

```
Lys Pro Gly Ala Ser Val Lys Val Ser Cys Lys Ala Ser Gly Tyr Thr
                165                 170                 175

Phe Thr Asp Tyr Glu Met His Trp Val Arg Gln Ala Pro Gly Gln Gly
            180                 185                 190

Leu Glu Trp Met Gly Ala Leu Asp Pro Lys Thr Gly Asp Thr Ala Tyr
        195                 200                 205

Ser Gln Lys Phe Lys Gly Arg Val Thr Leu Thr Ala Asp Glu Ser Thr
    210                 215                 220

Ser Thr Ala Tyr Met Glu Leu Ser Ser Leu Arg Ser Glu Asp Thr Ala
225                 230                 235                 240

Val Tyr Tyr Cys Thr Arg Phe Tyr Ser Tyr Thr Tyr Trp Gly Gln Gly
                245                 250                 255

Thr Leu Val Thr Val Ser Ser
            260
```

<210> SEQ ID NO 3
<211> LENGTH: 726
<212> TYPE: DNA
<213> ORGANISM: Artificial Sequence
<220> FEATURE:
<223> OTHER INFORMATION: CD19 scFv nucleotide

<400> SEQUENCE: 3

```
gacatccaga tgacacagac tacatcctcc ctgtctgcct ctctgggaga cagagtcacc    60
atcagttgca gggcaagtca ggacattagt aaatatttaa attggtatca gcagaaacca   120
gatggaactg ttaaactcct gatctaccat acatcaagat acactcagg agtcccatca    180
aggttcagtg gcagtgggtc tggaacagat tattctctca ccattagcaa cctggagcaa   240
gaagatattg ccacttactt ttgccaacag ggtaatacgc ttccgtacac gttcggaggg   300
gggaccaagc tggagatcac aggtggcggt ggctcgggcg gtggtgggtc gggtggcggc   360
ggatctgagg tgaaactgca ggagtcagga cctggcctgg tggcgccctc acagagcctg   420
tccgtcacat gcactgtctc aggggtctca ttacccgact atggtgtaag ctggattcgc   480
cagcctccac gaaagggtct ggagtggctg gagtaatat ggggtagtga aaccacatac    540
tataattcag ctctcaaatc cagactgacc atcatcaagg acaactccaa gagccaagtt   600
ttcttaaaaa tgaacagtct gcaaactgat gacacagcca tttactactg tgccaaacat   660
tattactacg gtggtagcta tgctatggac tactggggcc aaggaacctc agtcaccgtc   720
tcctca                                                              726
```

<210> SEQ ID NO 4
<211> LENGTH: 242
<212> TYPE: PRT
<213> ORGANISM: Artificial Sequence
<220> FEATURE:
<223> OTHER INFORMATION: CD19 scFv

<400> SEQUENCE: 4

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60
```

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
            85                  90                  95

Thr Phe Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
            195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 5
<211> LENGTH: 738
<212> TYPE: DNA
<213> ORGANISM: Artificial Sequence
<220> FEATURE:
<223> OTHER INFORMATION: BCMA scFv nucleotide

<400> SEQUENCE: 5

```
gacatcgtgc tgacccagag ccccgcttct ttagctgtgt ctttaggaga gagggccacc        60
atcaattgtc gtgcctccga gtccgtgtcc gtgattggcg cccatttaat ccactgtac       120
cagcagaaac ccggccagcc ccccaagctg ctgatctatt agccagcaa tctggagacc       180
ggcgtgcccg ccagatttag cggaagcggc tccggcaccg attttacttt aaccatttcc       240
tctttacaag ctgaggacgc cgccatctac tactgtttac agagcagaat ctttcctcgt       300
accttcggcc aaggtaccaa gctggaaatc aagggatcca ccagcggctc cggaaagccc       360
ggttccggag agggcagcac aaagggccaa gttcagctcg tgcagagcgg ctccgagctg       420
aagaagcccg cgcttccgt gaaggtgagc tgcaaggcca gcggatacac cttcaccgac       480
tactccatca actgggttcg tcaagctccc ggtcaaggtc tggagtggat gggctggatc       540
aacaccgaaa ccagagagcc cgcctatgcc tacgacttca gaggtcgttt cgtgttctct       600
ttagacacaa gcgtgagcac cgcctattta cagatcagct ctttaaaggc cgaggatacc       660
gccgtgtact actgcgctcg tgactacagc tacgccatgg actactgggg ccaaggtaca       720
ctggtgaccg tgtccagc                                                    738
```

<210> SEQ ID NO 6
<211> LENGTH: 246
<212> TYPE: PRT
<213> ORGANISM: Artificial Sequence
<220> FEATURE:
<223> OTHER INFORMATION: BCMA scFv

<400> SEQUENCE: 6

Asp Ile Val Leu Thr Gln Ser Pro Ala Ser Leu Ala Val Ser Leu Gly
1               5                   10                  15

Glu Arg Ala Thr Ile Asn Cys Arg Ala Ser Glu Ser Val Ser Val Ile
            20                  25                  30

Gly Ala His Leu Ile His Trp Tyr Gln Gln Lys Pro Gly Gln Pro Pro
        35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Ile Tyr Tyr Cys Leu Gln Ser Arg
                85                  90                  95

Ile Phe Pro Arg Thr Phe Gly Gln Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Val Gln Leu Val Gln Ser Gly Ser Glu Leu Lys Lys Pro Gly
    130                 135                 140

Ala Ser Val Lys Val Ser Cys Lys Ala Ser Gly Tyr Thr Phe Thr Asp
145                 150                 155                 160

Tyr Ser Ile Asn Trp Val Arg Gln Ala Pro Gly Gln Gly Leu Glu Trp
                165                 170                 175

Met Gly Trp Ile Asn Thr Glu Thr Arg Glu Pro Ala Tyr Ala Tyr Asp
            180                 185                 190

Phe Arg Gly Arg Phe Val Phe Ser Leu Asp Thr Ser Val Ser Thr Ala
        195                 200                 205

Tyr Leu Gln Ile Ser Ser Leu Lys Ala Glu Asp Thr Ala Val Tyr Tyr
    210                 215                 220

Cys Ala Arg Asp Tyr Ser Tyr Ala Met Asp Tyr Trp Gly Gln Gly Thr
225                 230                 235                 240

Leu Val Thr Val Ser Ser
                245

<210> SEQ ID NO 7
<211> LENGTH: 777
<212> TYPE: DNA
<213> ORGANISM: Artificial Sequence
<220> FEATURE:
<223> OTHER INFORMATION: MSLN scFv nucleotide

<400> SEQUENCE: 7
caggtgcagc tgcaacagag cggccctggc ctggtgacac cttcccagac cctcagcctc      60
acctgcgcca tctccggcga ttccgtgtcc agcaatagcg ccacctggaa ctggatcaga     120
cagagcccta gcagaggcct ggagtggctg gcaggaccta ttataggag caagtggtac      180 aacgactacg ccgtgtccgt caagtccaga atgagcatca ccccgacac cagcaagaat     240 cagttcagcc tgcagctgaa cagcgtgacc cccgaggaca cagccgtgta ttactgcgcc    300 agggcatga tgacctacta ctacggcatg gacgtgtggg gccaaggcac acagtgacc      360 gtgagcagcg gcattctggg cagcggagga ggcggatccg gcggcggagg cagcggagga    420
ggaggcagcc agcctgtgct gacccagtcc agctccctgt ccgcttcccc tggagcctcc    480
gcttccctga cctgcaccct gaggtccggc atcaatgtgg gcccctacag gatctactgg    540

```
tatcagcaga agcctggcag ccccccccag tacctgctga actacaagag cgacagcgac    600
aagcagcagg gcagcggagt gcctagcaga ttcagcggat ccaaggacgc ctccgccaat    660
gctggcgtgc tgctgatctc cggcctgaga agcgaggacg aagccgacta ctactgcatg    720
atctggcaca gcagcgctgc cgtgtttgga ggcggcaccc aactgacagt cctgtcc      777
```

<210> SEQ ID NO 8
<211> LENGTH: 259
<212> TYPE: PRT
<213> ORGANISM: Artificial Sequence
<220> FEATURE:
<223> OTHER INFORMATION: MSLN scFv

<400> SEQUENCE: 8

```
Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Gly Met Asp Val
            100                 105                 110

Trp Gly Gln Gly Thr Thr Val Thr Val Ser Ser Gly Ile Leu Gly Ser
        115                 120                 125

Gly Gly Gly Gly Ser Gly Gly Gly Ser Gly Gly Gly Ser Gln
    130                 135                 140

Pro Val Leu Thr Gln Ser Ser Leu Ser Ala Ser Pro Gly Ala Ser
145                 150                 155                 160

Ala Ser Leu Thr Cys Thr Leu Arg Ser Gly Ile Asn Val Gly Pro Tyr
                165                 170                 175

Arg Ile Tyr Trp Tyr Gln Gln Lys Pro Gly Ser Pro Pro Gln Tyr Leu
            180                 185                 190

Leu Asn Tyr Lys Ser Asp Ser Asp Lys Gln Gln Gly Ser Gly Val Pro
        195                 200                 205

Ser Arg Phe Ser Gly Ser Lys Asp Ala Ser Ala Asn Ala Gly Val Leu
    210                 215                 220

Leu Ile Ser Gly Leu Arg Ser Glu Asp Glu Ala Asp Tyr Tyr Cys Met
225                 230                 235                 240

Ile Trp His Ser Ser Ala Ala Val Phe Gly Gly Thr Gln Leu Thr
                245                 250                 255

Val Leu Ser
```

<210> SEQ ID NO 9
<211> LENGTH: 723
<212> TYPE: DNA
<213> ORGANISM: Artificial Sequence
<220> FEATURE:
<223> OTHER INFORMATION: HER2 scFv nucleotide

<400> SEQUENCE: 9

```
caggtccagc tgcagcagag cggacccgag ctcaagaagc ccggcgagac cgtgaagatc     60
```

```
agctgtaagg ccagcggcta cccctttacc aactatggaa tgaactgggt gaagcaagct    120
cccggccagg gcctgaagtg gatgggctgg atcaacacaa gcaccggaga agcaccttc    180 gctgacgact tcaagggcag atttgacttc tccctcgaga cctccgccaa caccgcctac    240
ctgcagatca caatctgaa gtccgaggac agcgctacct acttctgcgc cagatgggag    300
gtgtaccatg gctacgtccc ttattgggc caaggcacca ccgtgaccgt gagcagcgga    360
ggaggcggtt ctggaggcgg cggcagcggc ggcggcggca gcgacattca gctgacccag    420
tcccacaagt tcctgagcac ctccgtgggc gacagggtga gcattacctg caaggccagc    480
caggacgtgt acaatgccgt ggcctggtac agcagaagc ctggacagag ccccaagctg    540
ctgatctaca gcgcttcctc caggtacacc ggcgtccctt ccagatttac cggctccggc    600
tccggccccg acttcacctt caccatcagc tccgtgcagg ccgaagacct ggccgtgtac    660
ttctgccaac agcacttcag gaccccttc acctttggca gcggaaccaa gctggagatc    720
aaa                                                                   723

<210> SEQ ID NO 10
<211> LENGTH: 241
<212> TYPE: PRT
<213> ORGANISM: Artificial Sequence
<220> FEATURE:
<223> OTHER INFORMATION: HER2 scFv

<400> SEQUENCE: 10

Gln Val Gln Leu Gln Gln Ser Gly Pro Glu Leu Lys Lys Pro Gly Glu
1               5                   10                  15

Thr Val Lys Ile Ser Cys Lys Ala Ser Gly Tyr Pro Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Ser Thr Gly Glu Ser Thr Phe Ala Asp Asp Phe
    50                  55                  60

Lys Gly Arg Phe Asp Phe Ser Leu Glu Thr Ser Ala Asn Thr Ala Tyr
65                  70                  75                  80

Leu Gln Ile Asn Asn Leu Lys Ser Glu Asp Ser Ala Thr Tyr Phe Cys
                85                  90                  95

Ala Arg Trp Glu Val Tyr His Gly Tyr Val Pro Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Asp Ile Gln Leu Thr Gln Ser His Lys Phe
    130                 135                 140

Leu Ser Thr Ser Val Gly Asp Arg Val Ser Ile Thr Cys Lys Ala Ser
145                 150                 155                 160

Gln Asp Val Tyr Asn Ala Val Ala Trp Tyr Gln Gln Lys Pro Gly Gln
                165                 170                 175

Ser Pro Lys Leu Leu Ile Tyr Ser Ala Ser Ser Arg Tyr Thr Gly Val
            180                 185                 190

Pro Ser Arg Phe Thr Gly Ser Gly Ser Gly Pro Asp Phe Thr Phe Thr
        195                 200                 205

Ile Ser Ser Val Gln Ala Glu Asp Leu Ala Val Tyr Phe Cys Gln Gln
    210                 215                 220

His Phe Arg Thr Pro Phe Thr Phe Gly Ser Gly Thr Lys Leu Glu Ile
225                 230                 235                 240
```

Lys

<210> SEQ ID NO 11
<211> LENGTH: 207
<212> TYPE: DNA
<213> ORGANISM: Artificial Sequence
<220> FEATURE:
<223> OTHER INFORMATION: CD8 hinge region and transmembrane region nucleotide

<400> SEQUENCE: 11

```
accacgacgc cagcgccgcg accaccaaca ccggcgccca ccatcgcgtc gcagcccctg      60
tccctgcgcc cagaggcgtg ccggccagcg gcgggggggcg cagtgcacac gagggggctg    120
gacttcgcct gtgatatcta catctgggcg cccttggccg ggacttgtgg ggtccttctc    180
ctgtcactgg ttatcaccct ttactgc                                         207
```

<210> SEQ ID NO 12
<211> LENGTH: 69
<212> TYPE: PRT
<213> ORGANISM: Artificial Sequence
<220> FEATURE:
<223> OTHER INFORMATION: CD8 hinge region and transmembrane region

<400> SEQUENCE: 12

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 13
<211> LENGTH: 123
<212> TYPE: DNA
<213> ORGANISM: Artificial Sequence
<220> FEATURE:
<223> OTHER INFORMATION: CD28 intracellular domain nucleotide

<400> SEQUENCE: 13

```
aggagtaaga ggagcaggct cctgcacagt gactacatga acatgactcc cgccgcccc      60 gggcccaccc gcaagcatta ccagccctat gccccaccac gcgacttcgc agcctatcgc    120
tcc                                                                   123
```

<210> SEQ ID NO 14
<211> LENGTH: 41
<212> TYPE: PRT
<213> ORGANISM: Artificial Sequence
<220> FEATURE:
<223> OTHER INFORMATION: CD28 intracellular domain

<400> SEQUENCE: 14

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 15
<211> LENGTH: 126
<212> TYPE: DNA
<213> ORGANISM: Artificial Sequence
<220> FEATURE:
<223> OTHER INFORMATION: 41BB intracellular domain nucleotide

<400> SEQUENCE: 15
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 16
<211> LENGTH: 42
<212> TYPE: PRT
<213> ORGANISM: Artificial Sequence
<220> FEATURE:
<223> OTHER INFORMATION: 41BB intracellular domain

<400> SEQUENCE: 16

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 17
<211> LENGTH: 339
<212> TYPE: DNA
<213> ORGANISM: Artificial Sequence
<220> FEATURE:
<223> OTHER INFORMATION: CD3zeta nucleotide

<400> SEQUENCE: 17
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgctaa                          339

<210> SEQ ID NO 18
<211> LENGTH: 112
<212> TYPE: PRT
<213> ORGANISM: Artificial Sequence
<220> FEATURE:
<223> OTHER INFORMATION: CD3zeta

<400> SEQUENCE: 18

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

```
Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110
```

<210> SEQ ID NO 19
<211> LENGTH: 54
<212> TYPE: DNA
<213> ORGANISM: Artificial Sequence
<220> FEATURE:
<223> OTHER INFORMATION: 2A nucleotide

<400> SEQUENCE: 19

```
gagggcagag gaagtcttct aacatgcggt gacgtggagg agaatcccgg ccct      54
```

<210> SEQ ID NO 20
<211> LENGTH: 18
<212> TYPE: PRT
<213> ORGANISM: Artificial Sequence
<220> FEATURE:
<223> OTHER INFORMATION: 2A

<400> SEQUENCE: 20

```
Glu Gly Arg Gly Ser Leu Leu Thr Cys Gly Asp Val Glu Glu Asn Pro
 1               5                  10                  15

Gly Pro
```

<210> SEQ ID NO 21
<211> LENGTH: 1167
<212> TYPE: DNA
<213> ORGANISM: Artificial Sequence
<220> FEATURE:
<223> OTHER INFORMATION: L6 nucleotide

<400> SEQUENCE: 21

```
atgggggccg tcctgaggag cctcctggcc tgcagcttct gtgtgctcct gagagcggaa      60
cctccaacat gttctcctca gcagtttact tgtttcacgg gggaaattga ctgtatccct     120
gtggcttggc ggtgcgatgg gtttactgaa tgtgaagacc acagtgatga actcaattgt     180
cctgtatgct cagagtccca gttccagtgt gccagtgggc agtgtattga tggtgccctc     240
cgatgcaatg gagatgcaaa ctgccaggac aaatcagatg agaagaactg tgaagtgctt     300
tgtttaattg atcagttccg ctgtgccaat ggtcagtgca ttggaaagca agaagtgtgt     360
gatcataatg tggattgcag tgacaagtca gatgaactgg attgttatcc gactgaagaa     420
ccagcaccac aggccaccaa tacagttggt tctgttattg gcgtaattgt caccattttt     480
gtgtctggaa ctgtatactt tatctgccag aggatgttgt gtccacgtat gaagggagat     540
ggggaaacta tgactaatga ctatgtagtt catggaccag cttctgtgcc tcttggttat     600
gtgccacacc caagttcttt gtcaggatct cttccaggaa tgtctcgagg taaatcaatg     660
atcagctccc tcagtatcat gggggaagc agtggacccc ctatgaccg agcccatgtt     720 acaggagcat catcaagtag ttcttcaagc accaaaggca cttacttccc tgcaattttg     780
aaccctccac catccccagc cacagagcga tcacattaca ctatggaatt tggatattct     840
tcaaacagtc cttccactca taggtcatac agctacaggc catatagcta ccggcacttt     900
```

-continued

```
gcaccccca  ccacaccctg  cagcacagat  gtttgtgaca  gtgactatgc  tcctagtcgg     960
agaatgacct  cagtggcaac  agccaagggc  tataccagtg  acttgaacta  tgattcagaa    1020
cctgtgcccc  cacctcccac  accccgaagc  caatacttgt  cagcagagga  gaactatgaa    1080
agctgcccac  cttctccata  cagagagagg  agctattctc  atcacctcta  cccaccgcca    1140
ccctctccct  gtacagactc  ctcctga                                          1167
```

<210> SEQ ID NO 22
<211> LENGTH: 370
<212> TYPE: PRT
<213> ORGANISM: Artificial Sequence
<220> FEATURE:
<223> OTHER INFORMATION: L6

<400> SEQUENCE: 22

```
Gly Glu Pro Pro Thr Cys Ser Pro Gln Gln Phe Thr Cys Phe Thr Gly
1               5                   10                  15

Glu Ile Asp Cys Ile Pro Val Ala Trp Arg Cys Asp Gly Phe Thr Glu
            20                  25                  30

Cys Glu Asp His Ser Asp Glu Leu Asn Cys Pro Val Cys Ser Glu Ser
        35                  40                  45

Gln Phe Gln Cys Ala Ser Gly Gln Cys Ile Asp Gly Ala Leu Arg Cys
    50                  55                  60

Asn Gly Asp Ala Asn Cys Gln Asp Lys Ser Asp Glu Lys Asn Cys Glu
65                  70                  75                  80

Val Leu Cys Leu Ile Asp Gln Phe Arg Cys Ala Asn Gly Gln Cys Ile
                85                  90                  95

Gly Lys His Lys Lys Cys Asp His Asn Val Asp Cys Ser Asp Lys Ser
            100                 105                 110

Asp Glu Leu Asp Cys Tyr Pro Thr Glu Glu Pro Ala Pro Gln Ala Thr
        115                 120                 125

Asn Thr Val Gly Ser Val Ile Gly Val Ile Val Thr Ile Phe Val Ser
    130                 135                 140

Gly Thr Val Tyr Phe Ile Cys Gln Arg Met Leu Cys Pro Arg Met Lys
145                 150                 155                 160

Gly Asp Gly Glu Thr Met Thr Asn Asp Tyr Val Val His Gly Pro Ala
                165                 170                 175

Ser Val Pro Leu Gly Tyr Val Pro His Pro Ser Ser Leu Ser Gly Ser
            180                 185                 190

Leu Pro Gly Met Ser Arg Gly Lys Ser Met Ile Ser Ser Leu Ser Ile
        195                 200                 205

Met Gly Gly Ser Ser Gly Pro Pro Tyr Asp Arg Ala His Val Thr Gly
    210                 215                 220

Ala Ser Ser Ser Ser Ser Ser Thr Lys Gly Thr Tyr Phe Pro Ala
225                 230                 235                 240

Ile Leu Asn Pro Pro Ser Pro Ala Thr Glu Arg Ser His Tyr Thr
                245                 250                 255

Met Glu Phe Gly Tyr Ser Ser Asn Ser Pro Ser Thr His Arg Ser Tyr
            260                 265                 270

Ser Tyr Arg Pro Tyr Ser Tyr Arg His Phe Ala Pro Pro Thr Thr Pro
        275                 280                 285

Cys Ser Thr Asp Val Cys Asp Ser Asp Tyr Ala Pro Ser Arg Arg Met
    290                 295                 300

Thr Ser Val Ala Thr Ala Lys Gly Tyr Thr Ser Asp Leu Asn Tyr Asp
305                 310                 315                 320
```

```
Ser Glu Pro Val Pro Pro Pro Thr Pro Arg Ser Gln Tyr Leu Ser
            325                 330                 335

Ala Glu Glu Asn Tyr Glu Ser Cys Pro Pro Ser Pro Tyr Thr Glu Arg
        340                 345                 350

Ser Tyr Ser His His Leu Tyr Pro Pro Pro Ser Pro Cys Thr Asp
        355                 360                 365

Ser Ser
    370
```

<210> SEQ ID NO 23
<211> LENGTH: 804
<212> TYPE: DNA
<213> ORGANISM: Artificial Sequence
<220> FEATURE:
<223> OTHER INFORMATION: TL6 nucleotide

<400> SEQUENCE: 23

```
atggggccg tcctgaggag cctcctggcc tgcagcttct gtgtgctcct gagagcgcca      60
gcaccacagg ccaccaatac agttggttct gttattggcg taattgtcac cattttgtg    120
tctggaactg tatactttat ctgccagagg atgttgtgtc cacgtatgaa gggagatggg    180
gaaactatga ctaatgacta tgtagttcat ggaccagctt ctgtgcctct tggttatgtg    240
ccacacccaa gttctttgtc aggatctctt ccaggaatgt ctcgaggtaa atcaatgatc    300
agctccctca gtatcatggg gggaagcagt ggacccccct atgaccgagc ccatgttaca    360
ggagcatcat caagtagttc ttcaagcacc aaaggcactt acttccctgc aattttgaac    420
cctccaccat ccccagccac agagcgatca cattacacta tggaatttgg atattcttca    480
aacagtcctt ccactcatag gtcatacagc tacaggccat atagctaccg gcactttgca    540
cccccccacca caccctgcag cacagatgtt tgtgacagtg actatgctcc tagtcggaga    600
atgacctcag tggcaacagc caagggctat accagtgact tgaactatga ttcagaacct    660
gtgccccac tcccacacc ccgaagccaa tacttgtcag cagaggagaa ctatgaaagc    720
tgccccacctt ctccatacac agagaggagc tattctcatc acctctaccc accgccaccc    780
tctccctgta cagactcctc ctga                                           804
```

<210> SEQ ID NO 24
<211> LENGTH: 243
<212> TYPE: PRT
<213> ORGANISM: Artificial Sequence
<220> FEATURE:
<223> OTHER INFORMATION: TL6

<400> SEQUENCE: 24

```
Thr Asn Thr Val Gly Ser Val Ile Gly Val Ile Val Thr Ile Phe Val
1               5                   10                  15

Ser Gly Thr Val Tyr Phe Ile Cys Gln Arg Met Leu Cys Pro Arg Met
            20                  25                  30

Lys Gly Asp Gly Glu Thr Met Thr Asn Asp Tyr Val Val His Gly Pro
        35                  40                  45

Ala Ser Val Pro Leu Gly Tyr Val Pro His Pro Ser Ser Leu Ser Gly
    50                  55                  60

Ser Leu Pro Gly Met Ser Arg Gly Lys Ser Met Ile Ser Ser Leu Ser
65                  70                  75                  80

Ile Met Gly Gly Ser Ser Gly Pro Pro Tyr Asp Arg Ala His Val Thr
                85                  90                  95
```

```
Gly Ala Ser Ser Ser Ser Ser Ser Thr Lys Gly Thr Tyr Phe Pro
            100                 105                 110

Ala Ile Leu Asn Pro Pro Ser Pro Ala Thr Glu Arg Ser His Tyr
        115                 120                 125

Thr Met Glu Phe Gly Tyr Ser Ser Asn Ser Pro Ser Thr His Arg Ser
    130                 135                 140

Tyr Ser Tyr Arg Pro Tyr Ser Tyr Arg His Phe Ala Pro Pro Thr Thr
145                 150                 155                 160

Pro Cys Ser Thr Asp Val Cys Asp Ser Asp Tyr Ala Pro Ser Arg Arg
                165                 170                 175

Met Thr Ser Val Ala Thr Ala Lys Gly Tyr Thr Ser Asp Leu Asn Tyr
            180                 185                 190

Asp Ser Glu Pro Val Pro Pro Pro Thr Pro Arg Ser Gln Tyr Leu
            195                 200                 205

Ser Ala Glu Glu Asn Tyr Glu Ser Cys Pro Pro Ser Pro Tyr Thr Glu
        210                 215                 220

Arg Ser Tyr Ser His His Leu Tyr Pro Pro Pro Ser Pro Cys Thr
225                 230                 235                 240

Asp Ser Ser
```

<210> SEQ ID NO 25
<211> LENGTH: 1089
<212> TYPE: DNA
<213> ORGANISM: Artificial Sequence
<220> FEATURE:
<223> OTHER INFORMATION: L5 nucleotide

<400> SEQUENCE: 25

```
ggagagccgc ccacctgctc cccggaccag tttgcatgtg ccacagggga gatcgactgt    60
atccccgggg cctggcgctg tgacggcttt cccgagtgcg atgaccagag cgacgaggag   120
ggctgccccg tgtgctccgc cgcccagttc cctgcgcgc ggggtcagtg tgtggacctg    180
cgcctgcgct gcgacggcga ggcagactgt caggaccgct cagacgaggc ggactgtgac   240
gccatctgcc tgcccaacca gttccggtgt gcgagcggcc agtgtgtcct catcaaacag   300
cagtgcgact ccttccccga ctgtatcgac ggctccgacg agctcatgtg tgaaatcacc   360
aagccgccct cagacgacag cccggcccac agcagtgcca tcgggcccgt cattggcatc   420
atcctctctc tcttcgtcat gggtggtgtc tattttgtgt gccagcgcgt ggtgtgccag   480
cgctatgcgg gggccaacgg gcccttcccg cacgagtatg tcagcgggac cccgcacgtg   540
cccctcaatt tcatagcccc gggcggttcc agcatggcc ccttcacagg catcgcatgc    600
ggaaagtcca tgatgagctc cgtgagcctg atgggggggcc ggggcggggt gcccctctac   660
gaccggaacc acgtcacagg gcctcgtcc agcagctcgt ccagcacgaa ggccacgctg   720
tacccgccga tcctgaaccc gccgccctcc ccggccacgg acccctccct gtacaacatg   780
gacatgttct actcttcaaa cattccggcc actgcgagac cgtacaggcc ctacatcatt   840
cgaggaatgg cgccccgac gacgccctgc agcaccgacg tgtgtgacag cgactacagc   900
gccagccgct ggaaggccag caagtactac ctggatttga actcggactc agaccccctat   960
ccaccccac ccacgcccca cagccagtac ctgtcggcgg aggacagctg cccgccctcg   1020
cccgccaccg agaggagcta cttccatctc ttcccgcccc ctccgtcccc ctgcacggac   1080
tcatcctga                                                            1089
```

<210> SEQ ID NO 26

<211> LENGTH: 362
<212> TYPE: PRT
<213> ORGANISM: Artificial Sequence
<220> FEATURE:
<223> OTHER INFORMATION: L5

<400> SEQUENCE: 26

Gly Glu Pro Pro Thr Cys Ser Pro Asp Gln Phe Ala Cys Ala Thr Gly
1               5                   10                  15

Glu Ile Asp Cys Ile Pro Gly Ala Trp Arg Cys Asp Gly Phe Pro Glu
                20                  25                  30

Cys Asp Asp Gln Ser Asp Glu Glu Gly Cys Pro Val Cys Ser Ala Ala
            35                  40                  45

Gln Phe Pro Cys Ala Arg Gly Gln Cys Val Asp Leu Arg Leu Arg Cys
    50                  55                  60

Asp Gly Glu Ala Asp Cys Gln Asp Arg Ser Asp Glu Ala Asp Cys Asp
65                  70                  75                  80

Ala Ile Cys Leu Pro Asn Gln Phe Arg Cys Ala Ser Gly Gln Cys Val
                85                  90                  95

Leu Ile Lys Gln Gln Cys Asp Ser Phe Pro Asp Cys Ile Asp Gly Ser
                100                 105                 110

Asp Glu Leu Met Cys Glu Ile Thr Lys Pro Pro Ser Asp Ser Pro
            115                 120                 125

Ala His Ser Ser Ala Ile Gly Pro Val Ile Gly Ile Ile Leu Ser Leu
    130                 135                 140

Phe Val Met Gly Gly Val Tyr Phe Val Cys Gln Arg Val Val Cys Gln
145                 150                 155                 160

Arg Tyr Ala Gly Ala Asn Gly Pro Phe Pro His Glu Tyr Val Ser Gly
                165                 170                 175

Thr Pro His Val Pro Leu Asn Phe Ile Ala Pro Gly Gly Ser Gln His
            180                 185                 190

Gly Pro Phe Thr Gly Ile Ala Cys Gly Lys Ser Met Met Ser Ser Val
    195                 200                 205

Ser Leu Met Gly Gly Arg Gly Gly Val Pro Leu Tyr Asp Arg Asn His
210                 215                 220

Val Thr Gly Ala Ser Ser Ser Ser Ser Ser Thr Lys Ala Thr Leu
225                 230                 235                 240

Tyr Pro Pro Ile Leu Asn Pro Pro Ser Pro Ala Thr Asp Pro Ser
                245                 250                 255

Leu Tyr Asn Met Asp Met Phe Tyr Ser Ser Asn Ile Pro Ala Thr Ala
            260                 265                 270

Arg Pro Tyr Arg Pro Tyr Ile Ile Arg Gly Met Ala Pro Pro Thr Thr
    275                 280                 285

Pro Cys Ser Thr Asp Val Cys Asp Ser Asp Tyr Ser Ala Ser Arg Trp
    290                 295                 300

Lys Ala Ser Lys Tyr Tyr Leu Asp Leu Asn Ser Asp Ser Asp Pro Tyr
305                 310                 315                 320

Pro Pro Pro Pro Thr Pro His Ser Gln Tyr Leu Ser Ala Glu Asp Ser
                325                 330                 335

Cys Pro Pro Ser Pro Ala Thr Glu Arg Ser Tyr Phe His Leu Phe Pro
            340                 345                 350

Pro Pro Pro Ser Pro Cys Thr Asp Ser Ser
    355                 360

<210> SEQ ID NO 27

```
<211> LENGTH: 696
<212> TYPE: DNA
<213> ORGANISM: Artificial Sequence
<220> FEATURE:
<223> OTHER INFORMATION: TL5 nucleotide

<400> SEQUENCE: 27
agtgccatcg ggcccgtcat tggcatcatc ctctctctct tcgtcatggg tggtgtctat      60
tttgtgtgcc agcgcgtggt gtgccagcgc tatgcggggg ccaacgggcc cttcccgcac     120
gagtatgtca gcgggacccc gcacgtgccc ctcaatttca tagcccccggg cggttcccag     180
catggcccct tcacaggcat cgcatgcgga aagtccatga tgagctccgt gagcctgatg     240
ggggccggg gcggggtgcc cctctacgac cggaaccacg tcacagggc ctcgtccagc      300
agctcgtcca gcacgaaggc cacgctgtac ccgccgatcc tgaacccgcc gcctccccg      360
gccacggacc cctccctgta caacatggac atgttctact cttcaaacat tccggccact     420
gcgagaccgt acaggcccta catcattcga ggaatggcgc cccgacgac gccctgcagc      480
accgacgtgt gtgacagcga ctacagcgcc agccgctgga aggccagcaa gtactacctg     540
gatttgaact cggactcaga ccccctatcca ccccaccca cgcccacag ccagtacctg       600
tcggcggagg acagctgccc gccctcgccc gccaccgaga ggagctactt ccatctcttc     660
ccgcccccctc cgtccccctg cacggactca tcctga                               696

<210> SEQ ID NO 28
<211> LENGTH: 231
<212> TYPE: PRT
<213> ORGANISM: Artificial Sequence
<220> FEATURE:
<223> OTHER INFORMATION: TL5

<400> SEQUENCE: 28

Ser Ala Ile Gly Pro Val Ile Gly Ile Ile Leu Ser Leu Phe Val Met
1               5                  10                  15

Gly Gly Val Tyr Phe Val Cys Gln Arg Val Val Cys Gln Arg Tyr Ala
                20                  25                  30

Gly Ala Asn Gly Pro Phe Pro His Glu Tyr Val Ser Gly Thr Pro His
            35                  40                  45

Val Pro Leu Asn Phe Ile Ala Pro Gly Gly Ser Gln His Gly Pro Phe
        50                  55                  60

Thr Gly Ile Ala Cys Gly Lys Ser Met Met Ser Ser Val Ser Leu Met
65                  70                  75                  80

Gly Gly Arg Gly Gly Val Pro Leu Tyr Asp Arg Asn His Val Thr Gly
                85                  90                  95

Ala Ser Ser Ser Ser Ser Ser Thr Lys Ala Thr Leu Tyr Pro Pro
            100                 105                 110

Ile Leu Asn Pro Pro Ser Pro Ala Thr Asp Pro Ser Leu Tyr Asn
        115                 120                 125

Met Asp Met Phe Tyr Ser Ser Asn Ile Pro Ala Thr Ala Arg Pro Tyr
    130                 135                 140

Arg Pro Tyr Ile Ile Arg Gly Met Ala Pro Thr Thr Pro Cys Ser
145                 150                 155                 160

Thr Asp Val Cys Asp Ser Asp Tyr Ser Ala Ser Arg Trp Lys Ala Ser
                165                 170                 175

Lys Tyr Tyr Leu Asp Leu Asn Ser Asp Ser Asp Pro Tyr Pro Pro
            180                 185                 190

Pro Thr Pro His Ser Gln Tyr Leu Ser Ala Glu Asp Ser Cys Pro Pro
```

```
              195                 200                 205
Ser Pro Ala Thr Glu Arg Ser Tyr Phe His Leu Phe Pro Pro Pro
    210                 215                 220

Ser Pro Cys Thr Asp Ser Ser
225                 230

<210> SEQ ID NO 29
<211> LENGTH: 578
<212> TYPE: DNA
<213> ORGANISM: Artificial Sequence
<220> FEATURE:
<223> OTHER INFORMATION: IRES sequence

<400> SEQUENCE: 29
tccctccccc cccctaacg ttactggccg aagccgcttg gaataaggcc ggtgtgcgtt     60
tgtctatatg ttattttcca ccatattgcc gtctttggc aatgtgaggg cccggaaacc    120 tggcccctgtc ttcttgacga gcattcctag gggtctttcc cctctcgcca aggaatgca    180 aggtctgttg aatgtcgtga aggaagcagt tcctctggaa gcttcttgaa gacaaacaac    240
gtctgtagcg acccctttgca ggcagcggaa ccccccacct ggcgacaggt gcctctgcgg    300
ccaaaagcca cgtgtataag atacacctgc aaaggcggca caaccccagt gccacgttgt    360
gagttggata ttgtggaaa gagtcaaatg gctctcctca agcgtattca caagggggct    420
gaaggatgcc cagaaggtac cccattgtat gggatctgat ctggggcctc ggtgcacatg    480
ctttacatgt gtttagtcga ggttaaaaaa acgtctaggc cccccgaacc acggggacgt    540
ggttttcctt tgaaaaacac gatgataata tggccaca                             578

<210> SEQ ID NO 30
<211> LENGTH: 63
<212> TYPE: DNA
<213> ORGANISM: Artificial Sequence
<220> FEATURE:
<223> OTHER INFORMATION: Leading sequence nucleotide

<400> SEQUENCE: 30
atggctctgc ctgtgaccgc tctgctgctg cctctggctc tgctgctgca cgccgcaaga     60
cct                                                                    63

<210> SEQ ID NO 31
<211> LENGTH: 45
<212> TYPE: PRT
<213> ORGANISM: Artificial Sequence
<220> FEATURE:
<223> OTHER INFORMATION: CD8 hinge sequence

<400> SEQUENCE: 31

Thr Thr Thr Pro Ala Pro Arg Pro Pro Thr Pro Ala Pro Thr Ile Ala
1               5                  10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 32
<211> LENGTH: 135
<212> TYPE: DNA
<213> ORGANISM: Artificial Sequence
<220> FEATURE:
<223> OTHER INFORMATION: CD8 hinge sequence nucleotide
```

<400> SEQUENCE: 32
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgat                                                    135

<210> SEQ ID NO 33
<211> LENGTH: 24
<212> TYPE: PRT
<213> ORGANISM: Artificial Sequence
<220> FEATURE:
<223> OTHER INFORMATION: CD8 transmembrane sequence

<400> SEQUENCE: 33

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 34
<211> LENGTH: 72
<212> TYPE: DNA
<213> ORGANISM: Artificial Sequence
<220> FEATURE:
<223> OTHER INFORMATION: CD8 transmembrane sequence nucleotide

<400> SEQUENCE: 34
atctacatct gggcgccctt ggccgggact tgtgggtgtcc ttctcctgtc actggttatc    60 acccttact gc                                                         72

<210> SEQ ID NO 35
<211> LENGTH: 5
<212> TYPE: PRT
<213> ORGANISM: Artificial Sequence
<220> FEATURE:
<223> OTHER INFORMATION: GPC3 HCDR1

<400> SEQUENCE: 35

Asp Tyr Glu Met His
1               5

<210> SEQ ID NO 36
<211> LENGTH: 17
<212> TYPE: PRT
<213> ORGANISM: Artificial Sequence
<220> FEATURE:
<223> OTHER INFORMATION: GPC3 HCDR2

<400> SEQUENCE: 36

Ala Leu Asp Pro Lys Thr Gly Asp Thr Ala Tyr Ser Gln Lys Phe Lys
1               5                   10                  15

Gly

<210> SEQ ID NO 37
<211> LENGTH: 7
<212> TYPE: PRT
<213> ORGANISM: Artificial Sequence
<220> FEATURE:
<223> OTHER INFORMATION: GPC3 HCDR3

<400> SEQUENCE: 37

Phe Tyr Ser Tyr Thr Tyr Trp
1               5

<210> SEQ ID NO 38
<211> LENGTH: 16
<212> TYPE: PRT
<213> ORGANISM: Artificial Sequence
<220> FEATURE:
<223> OTHER INFORMATION: GPC3 LCDR1

<400> SEQUENCE: 38

```
Arg Ser Ser Gln Ser Leu Val His Ser Asn Gly Asn Thr Tyr Leu His
1               5                   10                  15
```

<210> SEQ ID NO 39
<211> LENGTH: 7
<212> TYPE: PRT
<213> ORGANISM: Artificial Sequence
<220> FEATURE:
<223> OTHER INFORMATION: GPC3 LCDR2

<400> SEQUENCE: 39

```
Lys Val Ser Asn Arg Phe Ser
1               5
```

<210> SEQ ID NO 40
<211> LENGTH: 9
<212> TYPE: PRT
<213> ORGANISM: Artificial Sequence
<220> FEATURE:
<223> OTHER INFORMATION: GPC3 LCDR3

<400> SEQUENCE: 40

```
Ser Gln Asn Thr His Val Pro Pro Thr
1               5
```

<210> SEQ ID NO 41
<211> LENGTH: 115
<212> TYPE: PRT
<213> ORGANISM: Artificial Sequence
<220> FEATURE:
<223> OTHER INFORMATION: GPC3 VH

<400> SEQUENCE: 41

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Phe Tyr Ser Tyr Thr Tyr Trp Gly Gln Gly Thr Leu Val Thr
                100                 105                 110

Val Ser Ser
        115
```

<210> SEQ ID NO 42
<211> LENGTH: 112
<212> TYPE: PRT
<213> ORGANISM: Artificial Sequence
<220> FEATURE:

<223> OTHER INFORMATION: GPC3 VL

<400> SEQUENCE: 42

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 43
<211> LENGTH: 7
<212> TYPE: PRT
<213> ORGANISM: Artificial Sequence
<220> FEATURE:
<223> OTHER INFORMATION: CD19 HCDR1

<400> SEQUENCE: 43

Leu Pro Asp Tyr Gly Val Ser
1               5

<210> SEQ ID NO 44
<211> LENGTH: 16
<212> TYPE: PRT
<213> ORGANISM: Artificial Sequence
<220> FEATURE:
<223> OTHER INFORMATION: CD19 HCDR2

<400> SEQUENCE: 44

Val Ile Trp Gly Ser Glu Thr Thr Tyr Tyr Asn Ser Ala Leu Lys Ser
1               5                   10                  15

<210> SEQ ID NO 45
<211> LENGTH: 13
<212> TYPE: PRT
<213> ORGANISM: Artificial Sequence
<220> FEATURE:
<223> OTHER INFORMATION: CD19 HCDR3

<400> SEQUENCE: 45

His Tyr Tyr Tyr Gly Gly Ser Tyr Ala Met Asp Tyr Trp
1               5                   10

<210> SEQ ID NO 46
<211> LENGTH: 11
<212> TYPE: PRT
<213> ORGANISM: Artificial Sequence
<220> FEATURE:
<223> OTHER INFORMATION: CD19 LCDR1

<400> SEQUENCE: 46

Arg Ala Ser Gln Asp Ile Ser Lys Tyr Leu Asn
1               5                   10

<210> SEQ ID NO 47

```
<211> LENGTH: 7
<212> TYPE: PRT
<213> ORGANISM: Artificial Sequence
<220> FEATURE:
<223> OTHER INFORMATION: CD19 LCDR2

<400> SEQUENCE: 47

His Thr Ser Arg Leu His Ser
1               5

<210> SEQ ID NO 48
<211> LENGTH: 9
<212> TYPE: PRT
<213> ORGANISM: Artificial Sequence
<220> FEATURE:
<223> OTHER INFORMATION: CD19 LCDR3

<400> SEQUENCE: 48

Gln Gln Gly Asn Thr Leu Pro Tyr Thr
1               5

<210> SEQ ID NO 49
<211> LENGTH: 119
<212> TYPE: PRT
<213> ORGANISM: Artificial Sequence
<220> FEATURE:
<223> OTHER INFORMATION: CD19 VH

<400> SEQUENCE: 49

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser
        115

<210> SEQ ID NO 50
<211> LENGTH: 107
<212> TYPE: PRT
<213> ORGANISM: Artificial Sequence
<220> FEATURE:
<223> OTHER INFORMATION: CD19 VL

<400> SEQUENCE: 50

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60
```

```
Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 51
<211> LENGTH: 5
<212> TYPE: PRT
<213> ORGANISM: Artificial Sequence
<220> FEATURE:
<223> OTHER INFORMATION: BCMA HCDR1

<400> SEQUENCE: 51

Asp Tyr Ser Ile Asn
1               5

<210> SEQ ID NO 52
<211> LENGTH: 17
<212> TYPE: PRT
<213> ORGANISM: Artificial Sequence
<220> FEATURE:
<223> OTHER INFORMATION: BCMA HCDR2

<400> SEQUENCE: 52

Trp Ile Asn Thr Glu Thr Arg Glu Pro Ala Tyr Ala Tyr Asp Phe Arg
1               5                   10                  15

Gly

<210> SEQ ID NO 53
<211> LENGTH: 9
<212> TYPE: PRT
<213> ORGANISM: Artificial Sequence
<220> FEATURE:
<223> OTHER INFORMATION: BCMA HCDR3

<400> SEQUENCE: 53

Asp Tyr Ser Tyr Ala Met Asp Tyr Trp
1               5

<210> SEQ ID NO 54
<211> LENGTH: 15
<212> TYPE: PRT
<213> ORGANISM: Artificial Sequence
<220> FEATURE:
<223> OTHER INFORMATION: BCMA LCDR1

<400> SEQUENCE: 54

Arg Ala Ser Glu Ser Val Ser Val Ile Gly Ala His Leu Ile His
1               5                   10                  15

<210> SEQ ID NO 55
<211> LENGTH: 7
<212> TYPE: PRT
<213> ORGANISM: Artificial Sequence
<220> FEATURE:
<223> OTHER INFORMATION: BCMA LCDR2

<400> SEQUENCE: 55

Leu Ala Ser Asn Leu Glu Thr
1               5

<210> SEQ ID NO 56
```

```
<211> LENGTH: 9
<212> TYPE: PRT
<213> ORGANISM: Artificial Sequence
<220> FEATURE:
<223> OTHER INFORMATION: BCMA LCDR3

<400> SEQUENCE: 56

Leu Gln Ser Arg Ile Phe Pro Arg Thr
1               5

<210> SEQ ID NO 57
<211> LENGTH: 117
<212> TYPE: PRT
<213> ORGANISM: Artificial Sequence
<220> FEATURE:
<223> OTHER INFORMATION: BCMA VH

<400> SEQUENCE: 57

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile Asn Trp Val Arg Gln Ala Pro Gly Gln Gly Leu Glu Trp Met
        35                  40                  45

Gly Trp Ile Asn Thr Glu Thr Arg Glu Pro Ala Tyr Ala Tyr Asp Phe
    50                  55                  60

Arg Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Ser Tyr Ala Met Asp Tyr Trp Gly Gln Gly Thr Leu
            100                 105                 110

Val Thr Val Ser Ser
        115

<210> SEQ ID NO 58
<211> LENGTH: 111
<212> TYPE: PRT
<213> ORGANISM: Artificial Sequence
<220> FEATURE:
<223> OTHER INFORMATION: BCMA VL

<400> SEQUENCE: 58

Asp Ile Val Leu Thr Gln Ser Pro Ala Ser Leu Ala Val Ser Leu Gly
1               5                   10                  15

Glu Arg Ala Thr Ile Asn Cys Arg Ala Ser Glu Ser Val Ser Val Ile
            20                  25                  30

Gly Ala His Leu Ile His Trp Tyr Gln Gln Lys Pro Gly Gln Pro Pro
        35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Ile Tyr Tyr Cys Leu Gln Ser Arg
                85                  90                  95

Ile Phe Pro Arg Thr Phe Gly Gln Gly Thr Lys Leu Glu Ile Lys
            100                 105                 110

<210> SEQ ID NO 59
<211> LENGTH: 7
```

```
<212> TYPE: PRT
<213> ORGANISM: Artificial Sequence
<220> FEATURE:
<223> OTHER INFORMATION: MSLN HCDR1

<400> SEQUENCE: 59

Ser Asn Ser Ala Thr Trp Asn
1               5

<210> SEQ ID NO 60
<211> LENGTH: 18
<212> TYPE: PRT
<213> ORGANISM: Artificial Sequence
<220> FEATURE:
<223> OTHER INFORMATION: MSLN HCDR2

<400> SEQUENCE: 60

Arg Thr Tyr Tyr Arg Ser Lys Trp Tyr Asn Asp Tyr Ala Val Ser Val
1               5                   10                  15

Lys Ser

<210> SEQ ID NO 61
<211> LENGTH: 12
<212> TYPE: PRT
<213> ORGANISM: Artificial Sequence
<220> FEATURE:
<223> OTHER INFORMATION: MSLN HCDR3

<400> SEQUENCE: 61

Gly Met Met Thr Tyr Tyr Tyr Gly Met Asp Val Trp
1               5                   10

<210> SEQ ID NO 62
<211> LENGTH: 14
<212> TYPE: PRT
<213> ORGANISM: Artificial Sequence
<220> FEATURE:
<223> OTHER INFORMATION: MSLN LCDR1

<400> SEQUENCE: 62

Thr Leu Arg Ser Gly Ile Asn Val Gly Pro Tyr Arg Ile Tyr
1               5                   10

<210> SEQ ID NO 63
<211> LENGTH: 11
<212> TYPE: PRT
<213> ORGANISM: Artificial Sequence
<220> FEATURE:
<223> OTHER INFORMATION: MSLN LCDR2

<400> SEQUENCE: 63

Tyr Lys Ser Asp Ser Asp Lys Gln Gln Gly Ser
1               5                   10

<210> SEQ ID NO 64
<211> LENGTH: 9
<212> TYPE: PRT
<213> ORGANISM: Artificial Sequence
<220> FEATURE:
<223> OTHER INFORMATION: MSLN LCDR3

<400> SEQUENCE: 64

Met Ile Trp His Ser Ser Ala Ala Val
1               5

<210> SEQ ID NO 65
```

<211> LENGTH: 123
<212> TYPE: PRT
<213> ORGANISM: Artificial Sequence
<220> FEATURE:
<223> OTHER INFORMATION: MSLN VH

<400> SEQUENCE: 65

Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Gly Met Asp Val
            100                 105                 110

Trp Gly Gln Gly Thr Thr Val Thr Val Ser Ser
        115                 120

<210> SEQ ID NO 66
<211> LENGTH: 116
<212> TYPE: PRT
<213> ORGANISM: Artificial Sequence
<220> FEATURE:
<223> OTHER INFORMATION: MSLN VL

<400> SEQUENCE: 66

Gln Pro Val Leu Thr Gln Ser Ser Ser Leu Ser Ala Ser Pro Gly Ala
1               5                   10                  15

Ser Ala Ser Leu Thr Cys Thr Leu Arg Ser Gly Ile Asn Val Gly Pro
            20                  25                  30

Tyr Arg Ile Tyr Trp Tyr Gln Gln Lys Pro Gly Ser Pro Pro Gln Tyr
        35                  40                  45

Leu Leu Asn Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Val
65                  70                  75                  80

Leu Leu Ile Ser Gly Leu Arg Ser Glu Asp Glu Ala Asp Tyr Tyr Cys
                85                  90                  95

Met Ile Trp His Ser Ser Ala Ala Val Phe Gly Gly Gly Thr Gln Leu
            100                 105                 110

Thr Val Leu Ser
        115

<210> SEQ ID NO 67
<211> LENGTH: 5
<212> TYPE: PRT
<213> ORGANISM: Artificial Sequence
<220> FEATURE:
<223> OTHER INFORMATION: HER2 HCDR1

<400> SEQUENCE: 67

Asn Tyr Gly Met Asn
1               5

```
<210> SEQ ID NO 68
<211> LENGTH: 17
<212> TYPE: PRT
<213> ORGANISM: Artificial Sequence
<220> FEATURE:
<223> OTHER INFORMATION: HER2 HCDR2

<400> SEQUENCE: 68

Trp Ile Asn Thr Ser Thr Gly Glu Ser Thr Phe Ala Asp Asp Phe Lys
1               5                   10                  15
Gly

<210> SEQ ID NO 69
<211> LENGTH: 11
<212> TYPE: PRT
<213> ORGANISM: Artificial Sequence
<220> FEATURE:
<223> OTHER INFORMATION: HER2 HCDR3

<400> SEQUENCE: 69

Trp Glu Val Tyr His Gly Tyr Val Pro Tyr Trp
1               5                   10

<210> SEQ ID NO 70
<211> LENGTH: 11
<212> TYPE: PRT
<213> ORGANISM: Artificial Sequence
<220> FEATURE:
<223> OTHER INFORMATION: HER2 LCDR1

<400> SEQUENCE: 70

Lys Ala Ser Gln Asp Val Tyr Asn Ala Val Ala
1               5                   10

<210> SEQ ID NO 71
<211> LENGTH: 7
<212> TYPE: PRT
<213> ORGANISM: Artificial Sequence
<220> FEATURE:
<223> OTHER INFORMATION: HER2 LCDR2

<400> SEQUENCE: 71

Ser Ala Ser Ser Arg Tyr Thr
1               5

<210> SEQ ID NO 72
<211> LENGTH: 9
<212> TYPE: PRT
<213> ORGANISM: Artificial Sequence
<220> FEATURE:
<223> OTHER INFORMATION: HER2 LCDR3

<400> SEQUENCE: 72

Gln Gln His Phe Arg Thr Pro Phe Thr
1               5

<210> SEQ ID NO 73
<211> LENGTH: 119
<212> TYPE: PRT
<213> ORGANISM: Artificial Sequence
<220> FEATURE:
<223> OTHER INFORMATION: HER2 VH

<400> SEQUENCE: 73

Gln Val Gln Leu Gln Gln Ser Gly Pro Glu Leu Lys Lys Pro Gly Glu
1               5                   10                  15
```

```
Thr Val Lys Ile Ser Cys Lys Ala Ser Gly Tyr Pro Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Ser Thr Gly Glu Ser Thr Phe Ala Asp Asp Phe
    50                  55                  60

Lys Gly Arg Phe Asp Phe Ser Leu Glu Thr Ser Ala Asn Thr Ala Tyr
65                  70                  75                  80

Leu Gln Ile Asn Asn Leu Lys Ser Glu Asp Ser Ala Thr Tyr Phe Cys
                85                  90                  95

Ala Arg Trp Glu Val Tyr His Gly Tyr Val Pro Tyr Trp Gly Gln Gly
            100                 105                 110

Thr Thr Val Thr Val Ser Ser
            115

<210> SEQ ID NO 74
<211> LENGTH: 107
<212> TYPE: PRT
<213> ORGANISM: Artificial Sequence
<220> FEATURE:
<223> OTHER INFORMATION: HER2 VL

<400> SEQUENCE: 74

Asp Ile Gln Leu Thr Gln Ser His Lys Phe Leu Ser Thr Ser Val Gly
1               5                   10                  15

Asp Arg Val Ser Ile Thr Cys Lys Ala Ser Gln Asp Val Tyr Asn Ala
            20                  25                  30

Val Ala Trp Tyr Gln Gln Lys Pro Gly Gln Ser Pro Lys Leu Leu Ile
        35                  40                  45

Tyr Ser Ala Ser Ser Arg Tyr Thr Gly Val Pro Ser Arg Phe Thr Gly
    50                  55                  60

Ser Gly Ser Gly Pro Asp Phe Thr Phe Thr Ile Ser Ser Val Gln Ala
65                  70                  75                  80

Glu Asp Leu Ala Val Tyr Phe Cys Gln Gln His Phe Arg Thr Pro Phe
                85                  90                  95

Thr Phe Gly Ser Gly Thr Lys Leu Glu Ile Lys
            100                 105
```